(12) United States Patent
Li et al.

(10) Patent No.: US 11,578,128 B2
(45) Date of Patent: Feb. 14, 2023

(54) ANTI-CTLA4 AND ANTI-PD-1 BIFUNCTIONAL ANTIBODY, PHARMACEUTICAL COMPOSITION THEREOF AND USE THEREOF

(71) Applicant: AKESO PHARMACEUTICALS, INC., Guangdong (CN)

(72) Inventors: Baiyong Li, Guangdong (CN); Yu Xia, Guangdong (CN); Zhongmin Maxwell Wang, Guangdong (CN); Peng Zhang, Guangdong (CN)

(73) Assignee: AKESO PHARMACEUTICALS, INC., Guangzhou (CN)

(*) Notice: Subject to any disclaimer, the term of this patent is extended or adjusted under 35 U.S.C. 154(b) by 426 days.

(21) Appl. No.: 16/327,076

(22) PCT Filed: Aug. 22, 2017

(86) PCT No.: PCT/CN2017/098466
§ 371 (c)(1),
(2) Date: Feb. 21, 2019

(87) PCT Pub. No.: WO2018/036473
PCT Pub. Date: Mar. 1, 2018

(65) Prior Publication Data
US 2019/0185569 A1 Jun. 20, 2019

(30) Foreign Application Priority Data
Aug. 23, 2016 (CN) .......................... 201610705624.2

(51) Int. Cl.
| C07K 16/28 | (2006.01) |
| A61K 39/395 | (2006.01) |
| G01N 33/577 | (2006.01) |
| A61P 35/00 | (2006.01) |
| G01N 33/68 | (2006.01) |
| C12N 15/62 | (2006.01) |
| A61P 7/06 | (2006.01) |
| C07K 16/46 | (2006.01) |
| A61P 35/02 | (2006.01) |
| A61K 39/00 | (2006.01) |

(52) U.S. Cl.
CPC ........ *C07K 16/2818* (2013.01); *A61K 39/395* (2013.01); *A61P 7/06* (2018.01); *A61P 35/00* (2018.01); *A61P 35/02* (2018.01); *C07K 16/46* (2013.01); *C07K 16/468* (2013.01); *C12N 15/62* (2013.01); *G01N 33/577* (2013.01); *G01N 33/68* (2013.01); *A61K 2039/505* (2013.01); *C07K 2317/24* (2013.01); *C07K 2317/31* (2013.01); *C07K 2317/622* (2013.01); *C07K 2317/76* (2013.01); *C07K 2317/92* (2013.01); *G01N 2333/70521* (2013.01)

(58) Field of Classification Search
CPC combination set(s) only.
See application file for complete search history.

(56) References Cited

U.S. PATENT DOCUMENTS

| 10,066,013 B2 | 9/2018 | Chen et al. |
| 2017/0216433 A1* | 8/2017 | Li ..................... A61K 39/39541 |
| 2019/0161548 A1* | 5/2019 | Johnson ................. A61P 35/00 |
| 2019/0177414 A1 | 6/2019 | Li et al. |
| 2019/0321466 A1 | 10/2019 | Li et al. |

FOREIGN PATENT DOCUMENTS

| CN | 1753912 B | 3/2006 |
| CN | 104974253 A | 10/2015 |
| CN | 104987421 A | 10/2015 |
| CN | 105175544 | * 12/2015 |
| CN | 105175544 A | 12/2015 |
| CN | 105175545 A | 12/2015 |
| CN | 105754990 A | 7/2016 |
| CN | 106967172 A | 7/2017 |
| CN | 106977602 A | 7/2017 |
| WO | WO 2009/134776 A2 | 11/2009 |
| WO | WO 2009/134776 A3 | 11/2009 |
| WO | WO 10/036959 A2 | 4/2010 |
| WO | WO 11/113019 A2 | 9/2011 |
| WO | WO 2012/120125 A1 | 9/2012 |
| WO | WO 12/145493 A1 | 10/2012 |
| WO | WO 2012135408 | 10/2012 |
| WO | WO 14/022758 A1 | 2/2014 |
| WO | WO 2014/209804 A1 | 12/2014 |
| WO | WO 2015/085847 A1 | 6/2015 |
| WO | WO 2015/101587 A1 | 7/2015 |

(Continued)

OTHER PUBLICATIONS

Okawa et al (Intern Med 58: 699-702, 2019) (IDS).*
Tanios (Blood (2018) 132 (Supplement 1): 2324) (IDS).*
CN105175544, Hu et al, published Dec. 2015, English Translation.*
Orcutt et al., "A modular IgG-scFv bispecific antibody topology," Protein Engineering, Design & Selection : PEDS APR 23(4):221-228 (2010).
Brahmer et al., "Nivolumab: targeting PD-1 to bolster antitumor immunity," Future Oncology 11(9):1307-1326 (2015).
McDermott et al., "Pembrolizumab: PD-1 inhibition as a therapeutic strategy in cancer," Drugs of Today 51(1):7-20 (2015).

(Continued)

*Primary Examiner* — Laura B Goddard
(74) *Attorney, Agent, or Firm* — Cooley LLP

(57) ABSTRACT

An anti-CTLA4 (cytotoxic T lymphocyte associated antigen 4) and anti-PD-1 (programmed cell death 1) bifunctional antibody. a pharmaceutical composition thereof and use thereof. Particularly, the anti-CLTA4 and anti-PD-1 bifunctional antibody comprises a first protein functional domain that targets PD-1 and a second protein functional domain that targets CTLA-4. The bifunctional antibody can bind to CTLA-4 and PD-1 specifically, relieve immunosuppression of CTLA4 and PD-1 on an organism specifically, activate T lymphocytes, and thus has good application prospects.

29 Claims, 31 Drawing Sheets

Specification includes a Sequence Listing.

(56) References Cited

FOREIGN PATENT DOCUMENTS

| WO | WO 2015/112800 A1 |   | 7/2015 |
|----|-------------------|---|--------|
| WO | WO 2016/015675    | * | 2/2016 |
| WO | WO 2016/015675 A1 |   | 2/2016 |
| WO | WO 2016/180034 A1 |   | 11/2016 |
| WO | WO 2017/106061 A1 |   | 6/2017 |
| WO | WO 2017/128534 A1 |   | 8/2017 |
| WO | WO 2018/036472 A1 |   | 3/2018 |
| WO | WO 2018/036473 A1 |   | 3/2018 |

OTHER PUBLICATIONS

Anonymous: "Study of REGN2810 (Anti-PD-1) in Patients With Advanced Malignancies—Full Text View—ClinicalTrials.gov", Mar. 9, 2015, Retrieved from the Internet: URL:https://clinicaltrials.gov/ct2/show/NCT02383212 [retrieved on Mar. 5, 2020], 8 pages.

Okawa et al., "Pembrolizmab-Induce Autoimmune Hemolytic Anemia and Hemophagocytic Lymphohistiocytosis in Non-Small Cell Lung Cancer," Intern Med 58:699-72 (2019).

Tanios et al., Auotimmune Hemolytic Anemia and Checkpoint Inhibitors: 68 Cases from the FDA Databaes and Critical Review, Blood 132(1):2324, pp. 1-6 (2018).

Altshuler et al, Production of recombinant antibodies and methods for increasing their affinity, Advances in biological chemistry 50:229-250 (2010).

Hoogenboom, H., Selecting and screening recombinant antibody libraries, Nature Biotechnology 23(9):1105-1116 (2005).

International Search Report based on International Patent Application No. PCT/CN2017/098466, dated Nov. 14, 2017, 12 pages includes English translation.

International Search Authority Written Opinion based on International Patent Application No. PCT/CN2017/098466, dated Nov. 14, 2017, 5 pages (Non-English).

English Translation of International Search Authority Written Opinion based on International Patent Application No. PCT/CN2017/098466, dated Nov. 14, 2017, 6 pages.

International Search Report based on International Patent Application No. PCT/CN2017/098465 dated Oct. 31, 2017, 12 pages including English translation.

International Search Authority Written Opinion based on International Patent Application No. PCT/CN2017/098465, dated Oct. 27, 2017, 5 pages (Non-English).

English Translation of International Search Authority Written Opinion based on International patent Application No. PCT/CN2017/098465, dated Oct. 27, 2017, 6 pages.

Chan et al., "Abstract 5021: Regulatory T-Cells and Effects of Anti-CTLA4 and anti-PD1 Therapy in a Transgenic Murine Model of Neuroblastoma," Proceedings: AACR Annual Meeting 2014; Apr. 5-9, 2014; San Diego, CA, 4 pages, retrieved May 22, 2019 at http://cancerres.aacrjournals.org/content/74/19_Supplement/5021.

Blatter et al., "Abstract 736: Combining PD1- and CTLA4-inhibiting antibodies with cisplatin or PARP inhibition in an attempt to eradicate BRCA1-deficient mouse mammary tumors," Cancer Research , AACR 106th Annual Meeting 2015; Apr. 18-22, 2015; Philadelphia, PA, 4 pages retrieved May 22, 2019 at http://cancerres.aacrjournals.org/content/75/15_Supplement/736.

Miao et al., "Role of Programmed Death-I PD-1 in Patients with Aplastic Anemia," Jiangsu Medical Journal, pp. 626-627 (2009).

* cited by examiner

Log (concentration)

Log (concentration)

ANTI-CTLA4 AND ANTI-PD-1 BIFUNCTIONAL ANTIBODY, PHARMACEUTICAL COMPOSITION THEREOF AND USE THEREOF

CROSS-REFERENCE TO RELATED APPLICATIONS

This application is a U.S. National Phase of PCT/CN2017/098466, filed Aug. 22, 2017, which claims priority to Chinese Application No. 201610705624.2, filed Aug. 23, 2016, each of which is hereby incorporated by reference.

TECHNICAL FIELD

The present invention belongs to the field of tumor therapy and molecular immunology. The present invention relates to anti-CTLA4 and anti-PD-1 bispecific antibodies, and their pharmaceutical compositions and methods of use. Specifically, the present invention relates to monoclonal antibodies against CTLA4 and PD-1 proteins.

TECHNICAL BACKGROUND

Cytotoxic T lymphocyte associated antigen 4 (CTLA4) closely relates to CD28 in gene structure, chromosomal localization, homology of sequences and gene expression, and both of them are receptors of costimulatory molecule B7, and mainly expresses on the cell surface of activated T cells. Interaction of CTLA4 and B7 inhibits the activation of T cells in mice and human, and negatively regulates the activation of T cells.

Anti-CTLA4 antibody or CTLA4 ligand can prevent CTLA4 from binding to its natural ligand, thereby block the negative signal transduction in T cells induced by CTLA4, and enhance the response of T cells to various antigens, which has been confirmed by both in vivo and in vitro studies. Currently, clinical trials of anti-CTLA4 antibodies treating prostate cancer, bladder cancer, colorectal cancer, gastrointestinal cancer, liver cancer, and malignant melanoma, etc. are ongoing (Grosso J F., Jure-Kunkel M N., CTLA-4 blockade in tumor models: an overview of preclinical and translational research. Cancer Immun. 2013; 13:5. Epub 2013 Jan. 22).

Interleukin 2 (IL-2) produced by T cells is a cytokine regulating proliferation of certain subgroups of T cells, and a crucial factor regulating immune responses, promoting the proliferation of activated B cells and participating in antibody responses, hematopoiesis and tumor surveillance. Recombinant human IL-2 has been approved by the U. S. FDA for the treatment of malignant tumors (including melanoma, renal tumors, etc.) while undergoing clinical studies to treat chronic viral infections (Chavez, A. R., et al., Pharmacologic administration of interleukin-2. Ann N Y Acad Sci, 2009. 1182: p. 14-27). In in vitro experiments, anti-CTLA4 antibodies can specifically remove the immunosuppression of CTLA4, activate T cells, and induce the generation of IL-2, displaying promising prospects in therapies for neoplastic and parasitic diseases.

As crucial factors on T cell functions, CTLA4 and anti-CTLA4 antibodies have particular therapeutic effects via intervening immune microenvironment, displaying high efficacy and supplementing traditional medicine, thereby crafting new opportunities in therapies. The therapeutic effects of CTLA4 and anti-CTLA4 antibodies are investigated in various pre-clinical and clinical studies, such as inhibition of airway hyper-responsiveness in asthma animal models, prevention of the development of rheumatic diseases, and induction of immune tolerance in allogeneic transplantation, etc. Meanwhile, although no adverse effects have been found in short-term clinical trials, we should note the potential impacts of long-term usage of drugs targeting CTLA4, such as anti-CTLA4 antibody, might provoke auto-immune diseases due to over-blockage on CTLA4-B7 signal pathway. Since antibodies can bind specifically to its antigen and induce target cell lysis or block pathological progress, drug development of antibodies especially humanized antibodies is very important in treating malignant tumors or auto-immune diseases.

The transmembrane receptor PD-1 (programmed cell death 1, also known as PD-1) is a member of the CD28 gene family, expresses in activated T cells, B cells and myeloid cells. Receptors of PD-1, PDL1 and PDL2, belong to the B7 superfamily; wherein PDL1 is broadly expressed in a variety of cells including T cells, B cells, endothelial cells and epithelial cells, while PDL2 is only expressed in antigen presenting cells such as dendritic cells and macrophages.

T cells play an important role in clearing viral infections, but T cell antivirus responses are often associated with immunopathogenesis. Although negative regulation of T cell activation mediated by PD-1 is critical in reducing tissue damage caused by infection, blocking or inhibiting the PD-1 pathway might lead to autoimmune diseases, for example, PD-1 gene knockout mice showed more effective clearance of pancreatic virus infection, but led to more severe liver damage (Iasi et al., 2003, j. Exp. J Med, 198, 39-50). In addition, tumors with high PD-1 expression often develop into cancers that are difficult to detect (Hamanishi et al., 2007, Proc. Natl. Acad. Sci. USA 104:3360-5). An established method to regulate PD-1 expression is through injection of antibodies in vivo.

Due to the broad antitumor prospects and astounding efficacy of PD-1 antibodies, it is generally believed that antibodies against PD-1 pathways will lead to breakthroughs in the treatment of a variety of tumors: non-small cell lung cancer, renal cell carcinoma, ovarian cancer, melanoma (Homet M. B., Parisi G., et al., Anti-PD-1 Therapy in Melanoma. Semin Oncol. 2015 June; 42(3):466-473), leukemia and anemia (Held S A, Heine A, et al., Advances in immunotherapy of chronic myeloid leukemia CML. Curr Cancer Drug Targets. 2013 September; 13(7):768-74). Ever since the revelation of the unprecedented clinical efficacy data at the annual meetings of American Association for Cancer Research (AACR) and American Society of Clinical Oncology (ASCO) in 2012 and 2013, PD-1 antibodies have become the hottest new drugs in R&D in the global pharmaceutical industry.

Interferon gamma (IFN-γ) is produced naturally mainly by natural killer (NK) cells, natural killer T (NKT) cells, or by effector T cells consisting of CD4$^+$ Th1 cells and CD8$^+$ cytotoxic T lymphocytes (CTL) after being stimulated by specific antigens. As an important innate immune and acquired immune cytokine, IFN-γ plays an import role in antagonizing or inhibiting viral, some bacterial and protozoon infections. In the meantime, IFN-γ can activate macrophages and induce the expression of type 2 major histocompatibility complex (MHC) to activate immune responses to control the progression of tumors (Schoenborn J R, Wilson C B. Regulation of Interferon-gamma Durin g Innate and Adaptive Immune Responses. Advances in Immunology 2007; 96: 41-101).

Monoclonal antibodies (mAbs) targeting a single antigen have been used to treat cancers, inflammation, infectious diseases, etc. However, the cause and in vivo factors of many diseases are complicated, including up- or down-regulations of different proteins, cytokines or receptors in different signaling pathways, either inhibiting or promoting biological functions. Therefore, simultaneously blocking different targets can improve treatment efficacy, which can be achieved by combinations of drugs with different targets or by one drug with multiple targets, such as multispecific antibodies.

Bispecific antibody, also called bi-functional antibody targeting two different antigens at the same time, can be produced by immune sorting purification, as well as advantageous recombinant technologies with flexibilities in binding site optimization, format of synthesis, and production output. At present, there have been more than 45 forms of bispecific antibodies (Müller D, Kontermann R E. Bispecific antibodies for cancer immunotherapy: Current perspectives. BioDrugs 2010; 24:89-98). The IgG-scFv structure, named after Morrison, has been used in many bispecific antibodies, (1997 Coloma M J, Morrison S L. The Design and production of will be tetravalent bispecific antibodies. Nat Biotechnol. Nature Biotechnology, 1997; 15, 15, 9-163). Bispecific antibody with IgG-scFv structure has been proven as an ideal form of bispecific antibody with advantages in antibody engineering, expression and purification due to its similarity to the natural IgG format (Miller B R, Demarest S J, et al., Stability engineering of scFvs for the development of bispecific and multivalent antibodies. Protein Eng Des Sel 2010; 23:549-57; Fitzgerald J, Lugovskoy A. Rational engineering of antibody therapeutics targeting multiple oncogene pathways. MAbs 2011; 3:299-309).

However, bispecific antibodies have been developed mostly against antigens on the surface of two different cells, not against two different antigens on the same cell. Thus, a bispecific antibody drug against both PD-1 and CTLA4 needs to be developed.

SUMMARY OF THE INVENTION

Through profound research and creative work, by immunizing mice with recombinant PD-1 or CTLA4 expressed in mammalian cells as antigen, the inventors obtained hybridoma cells via fusion of mouse splenocytes and myeloma cells. After screening a large number of samples, the inventors obtained the following hybridoma cell lines respectively:

Hybridoma cell line LT002 (CTLA4-4G10), which was preserved in China Center for Type Culture Collection (CCTCC) on Jun. 16, 2015, with the CCTCC Deposit Accession NO: C201587;

and hybridoma cell line LT003 (PD-1-14C12), which was preserved in China Center for Type Culture Collection (CCTCC) on Jun. 16, 2015, with the CCTCC Deposit Accession NO: C2015105.

The inventors surprisingly found that:

Hybridoma cell line LT002 is capable of secreting a specific monoclonal antibody (named 4G10) that binds specifically to CTLA4, and the monoclonal antibody can effectively block the interaction of CTLA4 to B7.

Hybridoma cell line LT003 is capable of secreting a specific monoclonal antibody (named 14C12) that specifically binds to PD-1, and the monoclonal antibody can effectively block the interaction of PD-1 to PDL1.

Furthermore, the inventors generated humanized antibodies against CTLA4 (named 4G10H1L1, 4G10H3L3, 4G10H4L3 and 8D2H14L2, respectively) and humanized antibodies against PD-1 (named 14C12H1L1) in a creative way.

Furthermore, the inventors created a series of new humanized bispecific antibodies (named BiAb001 BiAb002 BiAb003, BiAb004, BiAb007 and BiAb010, respectively) via recombining the two kinds of humanized antibodies, which can bind both CTLA4 and PD-1, and block interactions of CTLA4 with B7, and PD-1 with PDL1. The bispecific antibodies can effectively bind and activate human T cells, induce lymphocytes to secrete IFN-γ and IL-2, with the potential to be prepared into drugs for prevention and treatment of cancers, such as lung cancer, melanoma, renal cancer, ovarian cancer and leukemia.

The following are provided by the present invention:

The present invention relates to a bispecific antibody thereof, wherein, the first protein functional area targets PD-1, and the second protein functional area targets CTLA4, In one embodiment of the invention, the said bispecific antibody, wherein the said first and second protein functional areas are connected directly or via connecting fragments; Preferably, the connecting fragments are (GGGGS)n, and n is a positive integer, such as 1, 2, 3, 4, 5 or 6.

In one embodiment of the invention, the said bispecific antibody, wherein, the said first and second protein functional areas are respectively immunoglobulins or their antigen-binding fragments, such as half antibody, Fab, F(ab')2 or single-chain antibody.

Preferably, the said first protein functional area is an immunoglobulin, and the said second protein functional area is a single-chain antibody;

or,

Preferably, the said first protein functional area is a single-chain antibody, and the said second protein functional area is an immunoglobulin.

In one embodiment of the invention, the said bispecific antibody, wherein, the quantity of the first protein functional area or the second protein functional area is one, two, or more, independently.

In one embodiment of the invention, the said bispecific antibody, wherein, the said immunoglobulin is IgG, IgA, IgD, IgE or IgM; Preferably IgG, such as IgG1, IgG2, IgG3, or IgG4.

In one embodiment of the invention, the said bispecific antibody, wherein, the said single-chain antibody is attached at the c-terminal of the heavy chain of the immunoglobulin. Since one immunoglobulin consists of two heavy chains, thus one immunoglobulin molecule is linked to two single-chain antibody molecules. Preferably, the two said single-chain antibody molecules are the same.

In one embodiment of the invention, the said bispecific antibody, wherein, the heavy chain variable region of the said immunoglobulin comprises CDRs with the amino acid sequences of SEQ ID NO: 29-31, and the light chain variable region of the said immunoglobulin comprises CDRs with the amino acid sequences of SEQ ID NO: 32-34;

And/or, the heavy chain variable region of the said single-chain antibody comprises CDRs with the amino acid sequences of SEQ ID NO: 35-37, or SEQ ID NO: 35, SEQ ID NO: 41 and SEQ ID NO: 37, or SEQ ID NO: 42-44; and the light chain variable region of the said single-chain antibody comprises CDRs with the amino acid sequences of SEQ ID NO: 38-40, or SEQ ID NO: 45-47.

In one embodiment of the invention, the said bispecific antibody, wherein, the heavy chain variable region of the said immunoglobulin comprises CDRs with the amino acid sequences of SEQ ID NO: 35-37, or SEQ ID NO: 35, SEQ ID NO: 41 and SEQ ID NO: 37, or SEQ ID NO: 42-44; and the light chain variable region of the said immunoglobulin comprises CDRs with the amino acid sequences of SEQ ID NO: 38-40, or SEQ ID NO: 45-47;

and/or, the heavy chain variable region of the said single-chain antibody comprises CDRs with the amino acid sequences of SEQ ID NO: 29-31; and the light chain variable region of the said single-chain antibody comprises CDRs with the amino acid sequences of SEQ ID NO: 32-34.

In one embodiment of the invention, the said bispecific antibody, wherein, the amino acid sequence of the heavy chain variable region of the said immunoglobulin is selected from SEQ ID NO. 16 or SEQ ID NO. 20; the amino acid sequence of the light chain variable region of the said immunoglobulin is selected from SEQ ID NO: 18 or SEQ ID NO: 22;

And/or, the amino acid sequence of the heavy chain variable region of the said single-chain antibody is selected from SEQ ID NO: 2, SEQ ID NO: 6, SEQ ID NO: 10, SEQ ID NO: 14 or SEQ ID NO: 25; the amino acid sequence of the light chain variable region of the said single chain antibody is selected from SEQ ID NO: 4, SEQ ID NO: 8, SEQ ID NO: 12 or SEQ ID NO: 27.

In one embodiment of the invention, the said bispecific antibody, wherein, the amino acid sequence of the heavy chain variable region of the said immunoglobulin is selected from SEQ ID NO: 2, SEQ ID NO: 6, SEQ ID NO: 10, SEQ ID NO: 14 or SEQ ID NO: 25; the amino acid sequence of the light chain variable region of the single-chain antibody is selected from SEQ ID NO: 4, SEQ ID NO:8, SEQ ID NO:12 or SEQ ID NO:27;

and/or,

The amino acid sequence of the heavy chain variable region of the said single-chain antibody is selected from SEQ ID NO: 16 or SEQ ID NO: 20; the amino acid sequence of the light chain variable region of the said immunoglobulin is selected from SEQ ID NO: 18 or SEQ ID NO: 22.

In one embodiment of the invention, the said bispecific antibody, wherein, the said immunoglobulin contains non-CDR regions from species other than mouse, for example, from human.

In one embodiment of the invention, the constant region of the said immunoglobulin is humanized. For example, the constant region of the heavy chain is Ig gamma-1 chain C region, ACCESSION: P01857; the constant region of light chain is Ig kappa chain C region, ACCESSION: P01834.

In one embodiment of the invention, the said bispecific antibody, wherein, the said bispecific antibody binds to CTLA4 protein and/or PD-1 protein with a $K_D$ less than approximately $10^{-5}$ M, such as less than approximately $10^{-6}$ M, $10^{-7}$ M, $10^{-8}$ M, $10^{-9}$ M or $10^{-10}$ M or less.

The present invention also relates to a bispecific antibody, whose heavy chain variable region comprises CDRs with amino acid sequences of SEQ ID NO: 29-31, SEQ ID NO: 35-37, or SEQ ID NO: 35, SEQ ID NO: 41, and SEQ ID NO: 37, or SEQ ID NO: 42-44;

and, of SEQ ID NO: 32-34, or SEQ ID NO: 38-40, or SEQ ID NO: 45-47;

And light chain variable region comprises CDRs with amino acid sequences of SEQ ID NO: 32-34, or SEQ ID NO: 38-40, or SEQ ID NO: 45-47;

Preferably, the CDRs in the light chain variable region and the heavy chain variable region are not the same.

The present invention relates to an isolated nucleic acid molecule comprising a nucleotide sequence capable of encoding the heavy chain variable region of the antibody, wherein, the heavy chain variable region of the said antibody comprises CDRs with amino acid sequences selected from SEQ ID NO: 29-31, SEQ ID NO: 35-37, or SEQ ID NO: 35, SEQ ID NO: 41, and SEQ ID NO: 37, or SEQ ID NO: 42-44;

and, selected from SEQ ID NO: 32-34, or SEQ ID NO: 38-40, or SEQ ID NO: 45-47.

The present invention also relates to an isolated nucleic acid molecule comprising a nucleotide sequence capable of encoding the light chain variable region of the antibody, wherein, the light chain variable region of the said antibody comprises CDRs with amino acid sequences selected from SEQ ID NO: 32-34, or SEQ ID NO: 38-40, or SEQ ID NO: 45-47.

The present invention relates to a vector comprising the isolated nucleic acid molecule described in the present invention.

The present invention relates to a host cell comprising the isolated nucleic acid molecule described in the present invention, or the vector described in the present invention.

The present invention relates to a method for preparing the bispecific antibodies described in the present invention, by culturing the host cells in the present invention under appropriate conditions, and recovering the said bispecific antibodies from the cell culture.

The present invention relates to conjugates, including the bispecific antibodies described in the present invention and a conjugating partner as a detectable marker.

Specifically, the said conjugating partners are radioactive isotopes, fluorescein, luminescent materials, colorful substances, or enzymes.

The present invention relates to reagent kits, consisting of the bispecific antibodies or the conjugates described in the invention Specifically, the reagent kits may contain a secondary antibody, which specifically recognizes the said bispecific antibody; optionally, such secondary antibody may contain detectable markers such as radioactive isotopes, fluorescein, luminescent materials, colorful substances, or enzymes.

The present invention relates to usage of the said bispecific antibodies described in the present invention to prepare reagent kits for detection of the existence or the levels of CTLA4 and/or PD-1 in samples.

The present invention relates to a pharmaceutical composition comprising the said bispecific antibodies or the conjugates described in the invention. Optionally, it may also comprise a pharmaceutically acceptable carrier or excipient.

The present invention relates to use of the bispecific antibodies or conjugates described in the invention for producing drugs that are used for prevention and/or treatment of tumors or anemia, or for diagnosis of tumors or anemia; specifically, the said tumors may be melanoma, renal cancer, prostate cancer, bladder cancer, colorectal cancer, gastrointestinal cancer, liver cancer, non-small cell lung cancer, ovarian cancer and leukemia.

The present inventors have found through animal experiments that, bispecific antibody BiAb004 described in the invention can effectively inhibit the growth of MC38 tumor cells inoculated subcutaneously in right side of PD-1 HuGEMM mice, which the growth of tumor volume in PD-1 HuGEMM tumor-bearing mice is significantly inhibited.

The present invention relates to the use of the bispecific antibodies or the conjugates described in the present invention, to prepare drugs with the following purposes:

Testing CTLA4 level in samples,
Blocking CTLA4 binding to B7,
Regulating (e.g. down-regulating) CTLA4 activity or CTLA4 levels,
Removing immunosuppression of CTLA4,
Activating T lymphocytes, or
Increasing the secretion of IL-2 in T lymphocytes;
And/or,
Blocking PD-1 binding to PDL1,
Regulating (e.g. down-regulating) PD-1 activity or PD-1 levels,
Removing immunosuppression of PD-1, or
Increasing the secretion of IFN-γ in T lymphocytes.

The present invention relates to an in vivo or in vitro method to apply to cells or subjects in need with an effective dose of the bispecific antibodies or the conjugates described in the present invention, and the said method is selected from the following:

Testing CTLA4 level in samples,
Blocking CTLA4 binding to B7,
Regulating (e.g. down-regulating) CTLA4 activity or CTLA4 levels,
Removing immunosuppression of CTLA4,
Activating T lymphocytes, or
Increasing the secretion of IL-2 in T lymphocytes;
And/or,
Blocking PD-1 binding to PDL1,
Regulating (e.g. down-regulating) PD-1 activity or PD-1 levels,
Removing immunosuppression of PD-1, or
Increasing the secretion of IFN-γ in T lymphocytes.

In in vitro experiments in the present invention, the anti-CTLA4 antibodies, the anti-PD-1 antibodies, and the anti-CTLA4-anti-PD-1 bispecific antibodies described in the present invention all can induce the secretion of IFN-γ, and activate the immune response.

The present invention relates to a method for the prevention and/or treatment of tumors or anemia, or for diagnosis of tumors or anemia, including procedures to apply to subjects in need with an effective dose of the bispecific antibodies or the conjugates described in the present invention; specifically, the said tumors may be melanoma, renal cancer, prostate cancer, bladder cancer, colorectal cancer, gastrointestinal cancer, liver cancer, non-small cell lung cancer, ovarian cancer or leukemia.

The use of bispecific antibodies or conjugates thereof described in the present invention for the prevention and/or treatment of tumors or anemia, or for diagnosis of tumors or anemia; specifically, the said tumors may be melanoma, renal cancer, prostate cancer, bladder cancer, colorectal cancer, gastrointestinal cancer, liver cancer, non-small cell lung cancer, ovarian cancer or leukemia.

Use of bispecific antibodies or the conjugates thereof described in the present invention, with the following purposes:

Blocking CTLA4 binding to B7,
Regulating (e.g. down-regulating) CTLA4 activity or CTLA4 levels,
Removing immunosuppression of CTLA4,
Activating T lymphocytes, or
Increasing the secretion of IL-2 in T lymphocytes;
And/or,
Blocking PD-1 binding to PDL1,
Regulating (e.g. down-regulating) PD-1 activity or PD-1 levels,
Removing immunosuppression of PD-1, or
Increasing the secretion of IFN-γ in T lymphocytes.

Antibody drugs, especially monoclonal antibodies (MAB), have shown good efficacy in the treatment of a variety of diseases. The traditional methods to obtain therapeutic antibodies are to immunize animals with antigens to generate antigen-specific antibodies, or to improve low affinity antibodies by affinity maturation. However, these methods are time- and effort-consuming, and often may not target the specific epitopes on the antigen.

The variable regions of light and heavy chains of antibodies determine binding of an antibody to its antigen; a variable region of each chain contains three highly variable regions, which are called complementarity determining region (CDR) (the CDRs of a heavy chain (H) consist of HCDR1, HCDR2 and HCDR3; the CDRs of a light chain (L) consist of LCDR1, LCDR2 and LCDR3; named by Kabat et al (Sequences of Proteins of Immunological Interest, Fifth Edition (1991), 1-3, NIH Publication 91-3242, Bethesda Md.)).

Use conventional techniques known by those of ordinary skill in the art, for example, to analyze amino acid sequences of CDRs in the monoclonal antibodies listed in (1)-(13) through VBASE2 database, and the results are as follows:

(1) 14C12

The amino acid sequence of the heavy chain variable region is shown in SEQ ID NO: 16, and the amino acid sequence of the light chain variable region is shown in SEQ ID NO: 18.

The amino acid sequences of three CDRs of the heavy chain variable region are as follows:

```
                                    (SEQ ID NO: 29)
           HCDR1: GFAFSSYD (SEQ ID NO: 30)
           HCDR2: ISGGGRYT (SEQ ID NO: 31)
           HCDR3: ANRYGEAWFAY
```

The amino acid sequences of three CDRs of the light chain variable region are as follows:

```
                                    (SEQ ID NO: 32)
           LCDR1: QDINTY (SEQ ID NO: 33)
           LCDR2: RAN (SEQ ID NO: 34)
           LCDR3: LQYDEFPLT
```

(2) 14C12H1L1

The amino acid sequence of the heavy chain variable region is shown in SEQ ID NO: 20, and the amino acid sequence of the light chain variable region is shown in SEQ ID NO: 22.

The amino acid sequences of three CDRs of the heavy chain variable region are the same as those of 14C12.

The amino acid sequences of three CDRs of the light chain variable region are the same as those of 14C12.

(3) 4G10

The amino acid sequence of the heavy chain variable region is shown in SEQ ID NO: 2, and the amino acid sequence of the light chain variable region is shown in SEQ ID NO: 4.

The amino acid sequences of three CDRs of the heavy chain variable region are as follows:

HCDR1: GYSFTGYT (SEQ ID NO: 35)

HCDR2: INPYNNIT (SEQ ID NO: 36)

HCDR3: ARLDYRSY (SEQ ID NO: 37)

The amino acid sequences of three CDRs of the light chain variable region are as follows:

LCDR1: TGAVTTSNF (SEQ ID NO: 38)

LCDR2: GTN (SEQ ID NO: 39)

LCDR3: ALWYSNHWV (SEQ ID NO: 40)

(4) 4G10H1L1

The amino acid sequence of the heavy chain variable region is shown in SEQ ID NO: 6, and the amino acid sequence of the light chain variable region is shown in SEQ ID NO: 8.

The amino acid sequences of three CDRs of the heavy chain variable region are the same as those of 4G10.

The amino acid sequences of three CDRs of the light chain variable region are the same as those of 4G10.

(5) 4G10H3L3

The amino acid sequence of the heavy chain variable region is shown in SEQ ID NO: 10, and the amino acid sequence of the light chain variable region is shown in SEQ ID NO: 12.

The amino acid sequences of three CDRs of the heavy chain variable region are the same as those of 4G10.

The amino acid sequences of three CDRs of the light chain variable region are the same as those of 4G10.

(6) 4G10H4L3

The amino acid sequence of the heavy chain variable region is shown in SEQ ID NO: 14, and the amino acid sequence of the light chain variable region is shown in SEQ ID NO: 12.

The amino acid sequences of three CDRs of the heavy chain variable region are as follows:

HCDR1: GYSFTGYT (SEQ ID NO: 35)

HCDR2: INPYNDIT (SEQ ID NO: 41)

HCDR3: ARLDYRSY (SEQ ID NO: 37)

The amino acid sequences of three CDRs of the light chain variable region are the same as those of 4G10.

(7) 8D2H14L2

The amino acid sequence of the heavy chain variable region is shown in SEQ ID NO: 25, and the amino acid sequence of the light chain variable region is shown in SEQ ID NO: 27.

The amino acid sequences of three CDRs of the heavy chain variable region are as follows:

HCDR1: GFTFSDNW (SEQ ID NO: 42)

HCDR2: IRNKPYNYET (SEQ ID NO: 43)

HCDR3: TAQFAY (SEQ ID NO: 44)

The amino acid sequences of three CDRs of the light chain variable region are as follows:

LCDR1: ENIYGG (SEQ ID NO: 45)

LCDR2: GAT (SEQ ID NO: 46)

LCDR3: QNVLRSPFTF (SEQ ID NO: 47)

(8) BiAb001

The amino acid sequences of nine CDRs of the heavy chain variable regions are as follows

HCDR1: GFAFSSYD (SEQ ID NO: 29)

HCDR2: ISGGGRYT (SEQ ID NO: 30)

HCDR3: ANRYGEAWFAY (SEQ ID NO: 31)

HCDR4: GYSFTGYT (SEQ ID NO: 35)

HCDR5: INPYNNIT (SEQ ID NO: 36)

HCDR6: ARLDYRSY (SEQ ID NO: 37)

HCDR7: TGAVTTSNF (SEQ ID NO: 38)

HCDR8: GTN (SEQ ID NO: 39)

HCDR9: ALWYSNHWV (SEQ ID NO: 40)

The amino acid sequences of three CDRs of the light chain variable region are as follows:

LCDR1: QDINTY (SEQ ID NO: 32)

LCDR2: RAN (SEQ ID NO: 33)

LCDR3: LQYDEFPLT (SEQ ID NO: 34)

(9) BiAb002

The amino acid sequences of nine CDRs of the heavy chain variable regions are the same as those of BiAb001.

The amino acid sequences of three CDRs of the light chain variable region are the same as those of BiAb001.

(10) BiAb003

The amino acid sequences of nine CDRs of the heavy chain variable regions are the same as those of BiAb001.

The amino acid sequences of three CDRs of the light chain variable region are the same as those of BiAb001.

(11) BiAb004

The amino acid sequences of nine CDRs of the heavy chain variable regions are the same as those of BiAb001.

The amino acid sequences of three CDRs of the light chain variable region are the same as those of BiAb001.

(12) BiAb007

The amino acid sequences of nine CDRs of the heavy chain variable regions are as follows:

```
HCDR1: GFAFSSYD        (SEQ ID NO: 29)

HCDR2: ISGGGRYT        (SEQ ID NO: 30)

HCDR3: ANRYGEAWFAY     (SEQ ID NO: 31)

HCDR4: GYSFTGYT        (SEQ ID NO: 35)

HCDR5: INPYNDIT        (SEQ ID NO: 41)

HCDR6: ARLDYRSY        (SEQ ID NO: 37)

HCDR7: TGAVTTSNF       (SEQ ID NO: 38)

HCDR8: GTN             (SEQ ID NO: 39)

HCDR9: ALWYSNHWV       (SEQ ID NO: 40)
```

The amino acid sequences of three CDRs of the light chain variable region are the same as those of BiAb001.

(13) BiAb010

The amino acid sequences of nine CDRs of the heavy chain variable regions are as follows:

```
HCDR1: GFAFSSYD        (SEQ ID NO: 29)

HCDR2: ISGGGRYT        (SEQ ID NO: 30)

HCDR3: ANRYGEAWFAY     (SEQ ID NO: 31)

HCDR4: GFTFSDNW        (SEQ ID NO: 42)

HCDR5: IRNKPYNYET      (SEQ ID NO: 43)

HCDR6: TAQFAY          (SEQ ID NO: 44)

HCDR7: ENIYGG          (SEQ ID NO: 45)

HCDR8: GAT             (SEQ ID NO: 46)

HCDR9: QNVLRSPFTF      (SEQ ID NO: 47)
```

The amino acid sequences of three CDRs of the light chain variable region are the same as those of BiAb001.

Unless otherwise defined herein, scientific and technical terms used in connection with the present invention shall have the meanings that are commonly understood by those of ordinary skill in the art. Furthermore, laboratory techniques of cell and tissue culture, molecular genetics, oligo- or polynucleotide chemistry, and immunology described herein are those well-known and commonly used in the art. Meanwhile, to better understand the present invention, the following terms, unless otherwise indicated, shall be understood to have the following meanings:

As used herein, the term "amino acid sequence of CTLA4 (Cytotoxic T-Lymphocyte Antigen 4)" refers to not only the full-length CTLA4 protein, but also, the extracellular fragment of CTLA4 (CTLA4ECD), or fragments containing CTLA4ECD, or fusion proteins of CTLA4ECD, such as fragments of fusions with mouse or human IgG Fc fragments (mFc or hFc). However, understood by those of ordinary skill in the art, the amino acid sequence of CTLA4 protein can have natural or artificial mutations or variation (including but not limited to substitutions, deletions, and/or additions), not affecting its biological functions. Thus, in the present invention, the term "CTLA4 protein" also includes these amino acid sequences containing natural or artificial variants. Additionally, when referring to sequence fragments of CTLA4 protein, the sequence fragments containing natural or artificial variants are also included.

As used herein, the term "amino acid sequence of PD-1 (Programmed cell death protein 1, NCBI GenBank: 005018 NM)" refers to not only the full-length PD-1 protein, but also, the extracellular fragment of PD-1, PD-1ECD), or fragments containing PD-1ECD, or fusion proteins of PD-1ECD, such as fragments of fusions with mouse or human IgG Fc fragments (mFc or hFc). However, understood by those of ordinary skill in the art, the amino acid sequence of PD-1 protein can have natural or artificial mutations or variation (including but not limited to substitutions, deletions, and/or additions), not affecting its biological functions. Thus, in the present invention, the term "PD-1 protein" also includes these amino acid sequences containing natural or artificial variants. Additionally, when referring to sequence fragments of PD-1 protein, the sequences fragments containing natural or artificial variants are also included.

As used in this invention, if not specifically stated, B7 protein described herein is B7-1 and/or B7-2 protein whose amino acid sequences are well known in the prior art, which can be referenced from the existing literature or sequences disclosed in GenBank. For example, B7-1 (CD80, NCBI Gene ID: 941) and B7-2 (CD86, NCBI Gene ID: 942).

As used herein, the term "$EC_{50}$" refers to the concentration of 50% of maximal effect.

As used herein, the term "antibody" refers to an immunoglobulin molecule normally composed of two pairs of peptides (each pair with a "light" (L) chain and a "heavy" (H) chain). In general, the heavy chain can be comprehended as the polypeptide chain with a higher molecular weight, while the light chain refers to the polypeptide chain with a lower molecular weight. The light chains of an antibody are classified as either κ or λ light chains, while the heavy chains of an antibody are classified as μ, δ, γ, α or ε heavy chains, which define the antibody isotypes as IgM, IgD, IgG, IgA, and IgE, respectively.

Within a light and a heavy chain, the variable region and the constant region are connected through a "J" region consisting of about 12 or more amino acids, and a heavy chain also contains a "D" region consisting of about three or more amino acids. A heavy chain consists of a heavy chain variable region ($V_H$) and a heavy chain constant region ($C_H$). A heavy chain constant region consists of three structural domains ($C_H1$, $C_H2$, and $C_H3$). A light chain consists of a light chain variable region ($V_L$) and a light chain constant region ($C_L$). The constant region of a light chain consists of a structural domain $C_L$. The constant region of an antibody mediates the binding of an immunoglobulin to host tissues or factors, including various immune cells (e.g. effector cells) and the complement component 1q (C1q) of the classical complement system. $V_H$ and $V_L$ regions can further be subdivided into regions with high variability (known as complementarity determining region (CDR)), separated by relatively conservative regions called framework region (FR). Each $V_H$ and $V_L$ comprises three CDRs and four FRs in the order of FR1, CDR1, FR2, CDR2, FR3, CDR3, and FR4 from the amino terminus to the carboxyl terminus. The variable regions ($V_H$ and $V_L$) of each heavy/light chain form the antibody binding sites respectively. Distribution of amino acids to the regions or domains follows the definitions by Kabat Sequences of Proteins of Immunological Interest (National Institutes of Health, Bethesda, Md.) (1987 and 1991), or Chothia & Lesk (1987) j. Mol. Biol. 196:901-917; Chothia et al. (1989) Nature 342:878-883. In particular, heavy chains can also contain more than three CDRs, such as 6, 9, or 12. For example, in the case of the bispecific antibodies in the present invention, the heavy chain can be a heavy chain of an IgG antibody with a scFv of another antibody connected to its C terminus, thus this heavy chain contains 9 CDRs. The term "antibody" is not restricted by any particular method of making antibodies. For example, it includes, in particular, recombinant antibodies, monoclonal antibodies or polyclonal antibodies. Antibodies can be of different isoforms, such as IgG (for example, IgG1, IgG2, IgG3 or IgG4 subtypes), IgA1, IgA2, IgD, IgE or IgM antibodies.

As used herein, the term "antigen-binding fragments" refers to polypeptides containing fragments of a full-length antibody, maintaining the ability to bind specifically to the same antigen, and/or to compete with the full length antibody against the antigen, which is also called "the antigen binding portion". See Fundamental Immunology, Ch. 7 (Paul, W., 2nd edition, Raven Press, N.Y. (1989)), including the entire article and references in this invention for all purposes. Antigen-binding fragments can be produced by recombinant DNA techniques or by cleaving intact antibodies with proteolytic enzymes or chemicals. In some cases, the antigen-binding fragments include Fab, Fab', F(ab')2, Fd, Fv, dAb and CDR fragments, single-chain antibodies (e.g. scFV), chimeric antibodies, diabody, and polypeptide which includes at least a portion of the antibody which is sufficient to confer a specific antigen binding capacity.

As used herein the term "Fd fragment" refers to an antibody fragment composed of $V_H$ and $C_H1$ domains. The term "Fv fragment" refers to an antibody fragment composed of the $V_L$ and $V_H$ domains from a single arm of the antibody. The term "dAb fragment" refers to an antibody fragment composed of a $V_H$ domain (Ward et al., Nature 341:544 546 (1989)). The term "Fab fragment" refers to an antibody fragment composed of $V_L$, $V_H$, $C_L$ and $C_H1$ domains. The term "F(ab')2 fragment" refers to an antibody fragment containing two Fab fragments connected by a disulfide bridge in the hinge region.

In some cases, the antigen-binding fragments of an antibody are single-chain antibodies (e.g. scFv), a single polypeptide chain composed of $V_L$ and $V_H$ domains linked together (see, for example, Bird et al., Science 242: 423-426 (1988) and Huston et al., Proc. Natl. Acad. Sci. USA 85: 5879-5883 (1988)). Such scFv molecules may have a common structure: NH2-$V_L$-linker-$V_H$-COOH or NH2-$V_H$-linker-$V_L$-COOH. The appropriate linker may be a repeat of GGGGS or its variants, for example, amino acid sequence of (GGGGS)4 or its variants (Holliger et al., (1993), Proc. Natl. Acad. Sci. USA 90: 6444-6448). Other applicable linkers had been described by Alfthan, et al., (1995), Protein Eng. 8: 725-731, Choi, et al., (2001) Eur. J. Immunol. 31: 94-106, Hu, et al., (1996), Cancer Res. 56: 3055-3061, Kipriyanov et al., (1999), J. Mol. Biol. 293: 41-56 and Roovers, et al., (2001) Cancer Immunol.

In some cases, the antigen binding fragment is a diabody, namely, a dimeric antibody, whose $V_H$ and $V_L$ domains are lined on a single polypeptide chain, while because of the the too short linker to allow pairing between the two domains of on same chain, thus the domains are forced to pair with complementary domains on another chain to generate two antigen binding sites (see, for example, Holliger P. et al., Proc. Natl. Acad. Sci. USA 90: 6444-6448 (1993), and Poljak R. J. et al., Structure 2: 1121-1123 (1994)).

Using conventional techniques known by those of ordinary skill in the art (such as recombinant DNA technology or enzymatic/chemical cleavage), an antigen binding fragment (such as the antibody fragments described above) may be obtained from a given antibody, and screened for specificity in the same manner as for the full antibody.

In the present invention, unless specified otherwise, the term "antibody" refers to not only the intact antibody, but also the antigen binding fragments of the antibody.

As used in this invention, the terms "mAb" and "monoclonal antibodies" refers to an antibody or a fragment of an antibody that is derived from a group of highly homologous antibodies, i.e. from a group of identical antibody molecules, except for mutations that may arise spontaneously. Monoclonal antibody has high specificity against a single epitope on the antigen. Polyclonal antibodies are different from monoclonal antibodies, containing at least 2 or more different antibodies, which usually recognize different epitopes on the antigen. Monoclonal antibodies can be obtained with hybridoma technology reported originally by Kohler et al., (Nature, 256: 495, (1975)), as well as recombinant DNA Technology (see U.S. Pat. No. 4,816,567).

As used in this invention, the term "chimeric antibody" refers to an antibody in which parts of the light chain and/or heavy chain are from one antibody (can be from a particular species or belong to a specific antibody class or subclass), and the other parts of the light chain and/or heavy chain are from another antibody (can be from the same or different species or belong to the same or different antibodies classes or subclass). Nevertheless, it retains antigen binding activity (U.S.P. to Cabilly et al., U.S. Pat. No. 4,816,567; Morrison et al., Proc. Natl. Acad. Sci. USA, 81:6851 6855 (1984)).

As used in this invention, the term "humanized antibody" refers to an antibody or its fragments, derived from a human immunoglobulin (receptor antibody), whose CDRs or parts of CDRs are replaced by CDRs from a non-human antibody (donor antibody), where the donor antibody may be a non-human antibody (for example, from mice, rats, or rabbits) with predictable specificity, binding affinity, and reactivity. In addition, to further improve or optimize the performance of the antibody, some amino acid residues in framework regions (FR) of the receptor antibody can also be replaced by the corresponding amino acid residues of non-human species, or replaced by the corresponding amino acid residues of other antibodies. For more details on humanized antibodies, see for example Jones, et al., Nature, 321: 522-525 (1986); Reichmann et al., Nature, 332: 323-329 (1988); Presta, Curr. Op. Struct. Biol., 2: 593-596 (1992); and Clark, Immunol. Today, 21: 397-402 (2000).

As used in this invention, the term "Epitope" refers to a site on the antigen that the immunoglobulin or antibody can specifically bind to. "Epitope" is also known as the "antigenic determinant" in this field. Epitope or antigenic determinants usually consist of chemically active surface groups of molecules, such as amino acids, carbohydrates or glycoside chains, and usually have specific three dimensional structures, as well as specific charge characteristics. For example, epitopes typically consist of at least 3, 4, 5, 6, 7, 8, 9, 10, 11, 12, 13, 14 or 15 consecutive or non-consecutive amino acids in a unique spatial conformation, which can be "linear" or "conformational". See, for example, Epitope Mapping Protocols in Methods in Molecular Biology, volume 66, G. E. Morris, Ed. (1996). In a linear epitope, the interacting points between the protein and interacting molecule (e.g., antibodies) exist linearly along the primary amino acid sequence; while in a conformational epitope, the interacting points are separated along the primary amino acid sequence.

As used in this invention, the term "isolate" or "isolated" refers to obtained by artificial means in the natural state. If there is an "isolated" substance or component in nature, it may be due to the change in its natural environment, or isolated from the natural environment, or both. For example, polynucleotide or polypeptide in a natural existence in a living animal will be called "isolated" if it was separated with high purity in the same natural state. The term "isolate" or "isolated" does not exclude existence of artificial or synthetic material, or other impurities that does not affect the activity.

As used in this invention, the term "E. coli expression system" refers to the expression system composed of Escherichia coli (strain) and vector, where E. coli (strain) is commercially available, including but not limited to: GI698, ER2566, BL21 (DE3), B834 (DE3), and BLR (DE3).

As used in this invention, the term "vector" refers to a nucleic acid delivery vehicle that can be inserted with a polynucleotide. The vector that can have the protein that is encoded by the inserted polynucleotide expressed is called an expression vector. Vectors can be inserted into the host cell by transformation, transduction, or transfection, so that the genetic substances carried by the vector can be expressed in the host cell. Vectors are well known to the technical personnel in the field, including but not limited to: plasmid; phasmid; cosmid; artificial chromosome such as yeast artificial chromosome (YAC), bacterial artificial chromosome (BAC), or P1 derived artificial chromosome (PAC); phage such as λ phage or M13 phage and animal viruses etc. Animal viruses may include but not limited to, reverse transcriptase virus (including lentivirus), adenovirus, adeno-associated virus, herpes virus (e. g. herpes simplex virus), chicken pox virus, baculovirus, papilloma virus, and papova virus (such as SV40). A vector can contain multiple components that control expression, including but not limited to, promoter, transcription initiation factor, enhancer, selection element, and reporter gene. In addition, the vector may also contain replication initiation site.

As used in this invention, the term "host cell" refers to cells that can import vectors, including but not limited to, prokaryotic cells such as E. coli and Bacillus subtilis, fungal cells such as yeast and Aspergillus, insect cells such as S2 drosophila cells and Sf9, or animal cells such as fibroblast cells, CHO cells, COS cells, NSO cells, HeLa cells, BHK cells, HEK293 cells or human cells.

As used in this invention, "Homologous" refers to the sequence similarity or sequence identity between two polypeptides or between two nucleic acid molecules. When a position in the two compared sequences is occupied by the same base or amino acid, e.g., if a position in two DNA molecules is occupied by adenine, then the molecules are homologous at that position. The "percent homology" of two sequences is calculated by the function of the numbers of matched positions of the two sequences divided by the total numbers of positions that are compared multiplied by 100. For example, if 6 out of 10 positions of two sequences are matched, thus the homology of the two sequences is 60%. For example, homology of DNA sequences CTGACT and CAGGTT is 50% (3 out of 6 positions are matched). Generally, a comparison is made when two sequences are aligned to give maximum identity. Such alignment can be simply generated using computer programs, for instance, the ALIGN program (DNAstar, Inc.), implemented by the method of Needleman et al. (1970) J. Mol. Biol. 48: 443-453. Or, using the algorithm proposed by E. Meyers and W. Miller (Comput. Appl Biosci., 4:11-17 (1988)) that has been integrated into ALIGN program (version 2.0), in which the percent homology of two sequences is calculated by using PAM120 residue weight table, a gap length penalty of 12 and gap penalty of 4. In addition, GAP program that has been integrated into the GCG software package (available on www.gcg.com) implemented with algorithm of Needleman and Wunsch (J Mol Biol. 4-453 (1970)), Blossum 62 matrix, PAM250 matrix as well as 16, 14, 12, 10, 8, 6 or 4 GAP weight and 1, 2, 3, 4, 5 or 6 length weight can be used to measure the percent homology of two amino acid sequences.

As used in this invention, the term "specific binding" refers to non-randomly binding between two molecules, i.e., interaction between antibodies and antigen. In some embodiments, the antibody specifically binding to the antigen (or antibody with specificity to an antigen) refers that the antibody binds the antigen with an affinity ($K_D$) smaller approximately than $10^{-5}$ M, such as smaller than $10^{-6}$ M, $10^{-7}$ M, $10^{-8}$ M, $10^{-9}$ M, $10^{-10}$ M or even less. In some embodiments of the invention, the term "target(ed)" refers to specific binding.

As used in this invention, the term "$K_D$" refers to the dissociation equilibrium constant for specific antibody-antigen interactions, to describe the binding affinity between antibodies and antigens. The smaller the equilibrium dissociation constant is, the tighter the antibody binds antigen, the higher the affinity between the antibody and the antigen is. Generally, antibodies bind antigens with a dissociation equilibrium constant ($K_D$) less than approximately $10^{-5}$ M, in particular, less than approximately $10^{-6}$ M, $10^{-7}$ M, $10^{-8}$ M, $10^{-9}$ M, or $10^{-10}$ M, or less, for example, as measured with a BIACORE instrument by surface plasmon resonance (SPR).

As used in this invention, the terms "monoclonal antibodies" and "mAb" have the same meaning and are used interchangeably; the terms "polyclonal antibodies" and "PcAb" have the same meaning and are used interchangeably; the terms "polypeptide" and "protein" have the same meaning and are used interchangeably. Also in the present invention, amino acids are usually represented by single letter or three letter abbreviations known in the field. For example, alanine can be represented by A or Ala.

As used in this invention, the terms "hybridoma" and "hybridoma cell line" are used interchangeably, and when the terms "hybridoma" and "hybridoma cell line" are used, they also include subclones and progenies of the hybridoma cell line. For example, when referring to the hybridoma cell lines LT002 or LT003, it also refers to the subclones and progenies of the hybridoma cell lines LT002 or LT003.

As used in this invention, the term "pharmaceutically acceptable carrier and/or excipient" refers to a carrier and/or excipient that is compatible with the subject and active ingredients in pharmacology and/or physiology and is known to this field (e.g. Remington's Pharmaceutical Sciences. Edited by Gennaro A R, 19th ed. Pennsylvania: Mack Publishing Company, 1995), including but not limited to: pH regulator, surfactant, adjuvant, and ionic strength enhancer. For example, pH regulators include but not limited to phosphate buffers; Surfactants include but not limited to cations, anions or non-ionic surfactants such as Tween 80; Ionic strength enhancers include but not limited to sodium chloride.

As used in this invention, the term "adjuvant" refers to a nonspecific immune booster that, when delivered into the body together or beforehand with an antigen enhances or changes the body's immune response to the antigen. There are many kinds of adjuvants, including but not limited to aluminum adjuvants (such as aluminum hydroxide), freund's adjuvants (such as complete and incomplete freund's adjuvants), *Corynebacterium parvum*, lipopolysaccharides, cytokines, etc. Freund's adjuvant is currently the most commonly used adjuvant in animal experiments. Aluminum hydroxide adjuvant is used mostly in clinical trials.

As used in this invention, the term "effective dose" refers to the quantity that is sufficient to partially or completely achieve the desired effect. For example, effective prevention dose (e.g., diseases associated with CTLA4 binding to B7 or hyperactivity of CTLA4, such as tumors) is defined as the amount of a therapeutic sufficient to prevent, stop, or delay the diseases (e.g., diseases associated with hyperactivity of CTLA4 binding to B7 or diseases associated with hyperactivity of CTLA4, such as tumors); effective treatment dose is the amount of a therapeutic to cure, or at least partially stop, the disease and its complications in sick patients. Determination of such an effective dose is entirely within the scope of the capabilities of the technical personnel in the field. For example, the effective treatment dose will depend on the severity of the disease, the overall state of the patient's own immune system, the general background of patients such as age, weight and sex, administration of drugs, and other treatments at the same time.

Effects of the Invention

The monoclonal antibodies in the present invention, 4G10H1L1 and 4G10H3L3, are capable of binding to CTLA4 specifically, effectively blocking the interaction of CLTA4 and B7, and removing the immunosuppression of CLTA4 specifically to activate T lymphocytes.

The monoclonal antibody 14C12H1L1 is capable of binding to CTLA4 specifically, effectively blocking the interaction of CTLA4 and B7, and removing the immunosuppression of CTLA4 specifically to activate T lymphocytes.

The bispecific antibodies of the present invention have the potential to be prepared for drugs for the prevention and/or treatment of tumors, such as melanoma, renal cancer, prostate cancer, bladder cancer, colorectal cancer, gastrointestinal cancer, liver cancer, non-small cell lung cancer, ovarian cancer and leukemia.

DESCRIPTION OF THE DEPOSITED BIOLOGICAL MATERIALS

Figure 1:
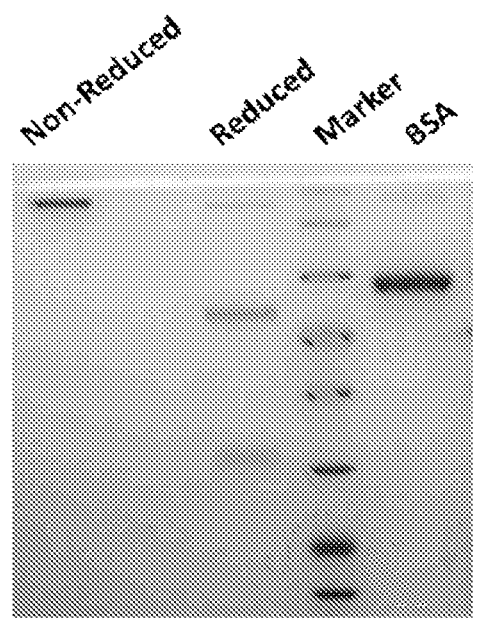
FIG. 1 SDS-PAGE Results of Monoclonal Antibody 4G10. From left to right: 1 μg antibody in non-reduced loading buffer; 1 μg antibody in reduced loading buffer; 5 μL Marker; 1 μg BSA.

LT002 (CTLA4-4G10), a hybridoma cell line, was preserved in China Center for Type Culture Collection (CCTCC) on Jun. 16, 2015. Deposit Accession NO.: C201587, Depository address: Wuhan university, Wuhan, China, zip code: 430072.

LT003 (PD-1-14C12), a hybridoma cell line, was preserved in China Center for Type Culture Collection (CCTCC) on Jun. 16, 2015. Deposit Accession NO.: C2015105, Depository address: Wuhan university, Wuhan, China, zip code: 430072.

DETAILED DESCRIPTION OF THE INVENTION

The invention will now be described in detail. As will be appreciated by one skilled in the art, the following examples are only used for the description of the invention, and not to be deemed to limit the scope of the invention. The cases without the specific descriptions of techniques or conditions were carried out in accordance with the literature in the field (e.g., Guide to Molecular Cloning, written by J Sambrook, et al, translated by Peitang Huang, et al, third Edition, Science Press) or in accordance with the product instruction manual. The reagents or instruments with no specified manufacturer were all conventional products available commercially.

In the embodiments of the present invention, the T cells used were from Akeso Biopharma, Inc., the BALB/C mice were purchased from the Guangdong Medical Laboratory Animal Center. The PD-1 HuGEMM mice used were from Nanjing Galaxy Biopharma Co., Ltd.; MC38 cells were from Shanghai Fudan IBS Cell Center.

Example 1: Preparation of Anti-CTLA4 Antibody 4G10

1. Establishment of Hybridoma Cell Line LT002

Using CTLA4-mFc (a fusion protein of human CTLA4 protein (GenbankID: NP 005205.2) extracellular region and mouse IgG1Fc protein) as the antigen, the hybridoma cells were obtained by fusing the splenocytes of immunized BALB/C mice (purchased from Guangdong Medical Laboratory Animal Center) and mouse myeloma cells with currently established method (for example, Stewart, S. J., "Monoclonal Antibody Production", in Basic Methods in antibody Production and Characterization, Eds. G. C. Howard and D. R. Bethell, Boca Raton: CRC Press, 2000).

The CTLA4 protein was generated by digesting the fusion protein CTLA4-mFc with TEV protease, and further purified by purification column. Microplate was coated with CTLA4 as the antigen, and the above hybridoma cells were screened by indirect ELISA to select those secreting new antibodies specifically binding to CTLA4. The hybridoma cells screened via indirect ELISA were further screened by competitive ELISA against ligand B7-1 (CD80, NCBI Gene ID:

941) and B7-2 (CD86, NCBI Gene ID: 942) to select those secreting monoclonal antibodies that competitively bind to CTLA4, and then a stable hybridoma cell line was obtained by limited dilution method. This hybridoma cell line was named LT002 (CTLA4-4G10), and its secreted monoclonal antibody is named 4G10.

LT002 (CTLA4-4G10), the hybridoma cell line, was preserved in China Center for Type Culture Collection (CCTCC) on Jun. 16, 2015. Deposit Accession NO.: C201587, Depository address: Wuhan university, Wuhan, China, postcode: 430072.

2. Preparation of Anti-CTLA4 Antibody 4G10

The LT002 cells in the present invention were cultured using IMDM medium containing 10% low IgG fetal bovine serum (IMDM medium containing 1% streptomycin, cultured in cell incubator with 5% $CO_2$, 37° C.), and then the cell culture supernatant was harvested and purified by high-speed centrifugation after 7 days culture, filtration through microporous membrane, and HiTrap protein A HP column to get the antibody 4G10. The purified 4G10 were identified on SDS-PAGE electrophoresis, and the result was shown in FIG. 1.

Example 2: Sequence Analysis of Anti-CTLA4 Antibody 4G10

Sequence Analysis of Antibody 4G10 mRNA was extracted from the hybridoma cell line LT002 prepared in Example 1 above according to the manual of the cell/bacterial total RNA extraction reagent kit (Tiangen, Product No DP430).

cDNA was synthesized using Invitrogen SuperScript® III First-Strand Synthesis System for RT-PCR, and amplified by PCR.

TA cloning was directly carried out on the PCR amplified product according to the instructions of pEASY-T1 Cloning Kit (Transgen CT101).

The products of TA cloning were directly sequenced, and the sequencing results were as follows:

Nucleic Acid Sequence of Heavy Chain Variable Region: (372 bp)

(SEQ ID NO: 1)
CAGGTCAAGCTGCAGGAGTCTGGACCTGAGCTGGTGAAGCCTGGAGCTTC

AATGAAGATATCCTGCAAGGCTTCTGGTTACTCATTCACTGGCTACACCA

TGAACTGGGTGAAGCAGAGCCATGGAAAGAACCTTGAATGGATTGGACTT

ATTAATCCTTACAATAATATTACTAACTACAACCAGAAGTTCATGGGCAA

GGCCACATTTACTGTAGACAAGTCATCCAGCACAGCCTACATGGAACTCC

TCAGACTGACATCTGAAGACTCTGGAGTCTATTTCTGTGCAAGACTCGAC

TATAGGTCTTATTGGGGCCAAGGGACTCTGGTCACTGTCTCTGCAGCCAA

AACGACACCCCCATCTGTCTAT

Encoded Amino Acid Sequence: (124 aa)

(SEQ ID NO: 2)
QVKLQESGPELVKPGASMKISCKASGYSFTGYTMNWVKQSHGKNLEWIGL

INPYNNITNYNQKFMGKATFTVDKSSSTAYMELLRLTSEDSGVYFCARLD

YRSYWGQGTLVTVSAAKTTPPSVY

Nucleic Acid Sequence of the Light Chain Variable Region: (378 bp)

(SEQ ID NO: 3)
CAGGCTGTTGTGACTCAGGAATCTGCACTCACCACATCACCTGGTGAAAC

AGTCACACTCACTTGTCGCTCAAGTACTGGGGCTGTTACAACTAGTAACT

TTGCCAACTGGGTCCAAGAAAAACCAGATCATTTATTCACTAGTCTAATA

GGTGGTACCAACAACCGAGCTCCAGGTGTTCCTGCCAGATTCTCAGGCTC

CCTGATTGGAGACAAGGCTGCCCTCACCATCACAGGGGCACAGACTGAGG

ATGAGGCAATATATTTCTGTGCTCTATGGTACAGCAACCATTGGGTGTTC

GGTGGAGGAACCAAACTGACTGTCCTAGGCCAGCCCAAGTCTTCGCCATC

AGTCACCCTGTTTCAAGGGCAATTCTGC

Encoded Amino Acid Sequence: (126 aa)

(SEQ ID NO: 4)
QAVVTQESALTTSPGETVTLTCRSSTGAVTTSNFANWVQEKPDHLFTSLI

GGTNNRAPGVPARFSGSLIGDKAALTITGAQTEDEAIYFCALWYSNHWVF

GGGTKLTVLGQPKSSPSVTLFQGQFC

Example 3: Design and Preparation of Humanized Antibodies 4G10H1L1, 4G10H3L3 and 4G10H4L3 Against CTLA4

1. Design of Light and Heavy Chain Sequences of Anti-CTLA4 Humanized Antibodies 4G10H1L1, 4G10H3L3 and 4G10H4L3

Based on the three-dimensional crystal structure of CTLA4 protein (Nat. Struct. Biol., (1997) 4 p. 527) and the amino acid sequence of antibody 4G10 obtained in the Example 2, antibody in silico modeling was performed and mutations of amino acids from mouse-like to human-like were engineered to obtain the amino acid sequences of variable regions of antibody 4G10H1L1, 4G10H3L3 and 4G10H4L3 (the constant region of heavy chain was Ig gamma-1 chain C region, ACCESSION: P01857 and the constant region of light chain was Ig kappa chain C region, ACCESSION: P01834)

The designed sequences of variable regions are as follows (1) The Heavy Chain and Light Chain Sequences of the Humanized Monoclonal Antibody 4G10H1L1

Nucleic Acid Sequence of the Heavy Chain Variable Region: (345 bp)

(SEQ ID NO: 5)
CAGGTGCAGCTGGTGGAGTCTGGGGCCGAGCTGGTGAAGCCCGGCGCCTC

CATGAAGATCTCTTGCAAGGCCAGCGGATACAGTTTCACTGGCTATACCA

TGAACTGGGTCAAACAGGCTCCAGGACAGGGACTGGAGTGGATCGGCTG

ATTAATCCTTACAACAACATCACCAACTACAACCAGAAGTTCATGGGAAA

AGCAACCTTTACAGTGGACAAGAGCATTTCCACAGCCTACATGGAACTGA

GCCGGCTGACTTCAGACGATAGCGGGGTCTATTTTTGTGCAAGGCTGGAT

TATCGCTCTTACTGGGGGCAGGGAACTCTGGTCACTGTCTCCGCT

Encoded Amino Acid Sequence: (115 aa)

(SEQ ID NO: 6)
QVQLVESGAELVKPGASMKISCKASGYSFTGYTMNWVKQAPGQGLEWIGL

INPYNNITNYNQKFMGKATFTVDKSISTAYMELSRLTSDDSGVYFCARLD

YRSYWGQGTLVTVSA

Nucleic Acid Sequence of the Light Chain Variable Region: (327 bp)

(SEQ ID NO: 7)
CAGGCTGTCGTCACTCAGGAACCTTCACTGACTGTGAGCCCAGGAGGAAC

TGTCACCCTGACATGCGGAAGCTCCACCGGAGCAGTGACCACATCCAACT

TCGCCAATTGGGTCCAGGAAAAGCCAGGCCAGGCATTTCGATCCCTGATC

GGAGGCACAAACAATCGGGCTTCTTGGGTGCCCGCAAGATTCTCAGGAAG

CCTGCTGGGGGAAAAGCCGCTCTGACCATTAGTGGCGCTCAGCCTGAGG

ACGAAGCCGAGTACTTCTGCGCTCTGTGGTATAGCAACCACTGGGTGTTT

GGCGGGGAACAAAGCTGACTGTGCTG

Encoded Amino Acid Sequence: (109 aa)

(SEQ ID NO: 8)
QAVVTQEPSLTVSPGGTVTLTCGSSTGAVTTSNFANWVQEKPGQAFRSLI

GGTNNRASWVPARFSGSLLGGKAALTISGAQPEDEAEYFCALWYSNHWVF

GGGTKLTVL (2) The Heavy Chain and Light Chain Sequences of the Humanized Monoclonal Antibody 4G10H3L3
Nucleic Acid Sequence of the Heavy Chain Variable Region: (345 bp)

(SEQ ID NO: 9)
CAGGTGCAGCTGGTCGAGTCTGGGGCCGAAGTGAAGAAACCCGGCGCCTC

AGTGAAGGTCAGCTGCAAGGCCAGCGGGTACAGTTTCACTGGATATACCA

TGAACTGGGTCCGACAGGCCCCTGGCCAGGGGCTGGAGTGGATCGGCCTG

ATTAACCCTTACAACAACATCACTAACTACGCACAGAAGTTCCAGGGGAG

AGTGACCTTTACAGTGGACACCAGCATTTCCACAGCCTACATGGAACTGT

CCCGGCTGAGATCTGACGATACAGGCGTGTACTTCTGCGCTAGGCTGGAT

TACCGCAGCTATTGGGGACAGGGCACACTGGTGACTGTCAGCGCA

Encoded Amino Acid Sequence: (115 aa)

(SEQ ID NO: 10)
QVQLVESGAEVKKPGASVKVSCKASGYSFTGYTMNWVRQAPGQGLEWIGL

INPYNNITNYAQKFQGRVTFTVDTSISTAYMELSRLSDDTGVYFCARLD

YRSYWGQGTLVTVSA

Nucleic Acid Sequence of the Light Chain Variable Region: (327 bp)

(SEQ ID NO: 11)
CAGGCTGTCGTCACTCAGGAACCTTCACTGACCGTGTCTCCTGGCGGGAC

TGTCACCCTGACATGCGGCAGCTCCACAGGGGCCGTGACCACAAGTAACT

TCCCAAATTGGGTCCAGCAGAAGCCAGGACAGGCTCCCCGGAGTCTGATC

GGAGGCACCAACAACAAGGCCAGCTGGACACCCGCACGGTTCAGCGGCAG

CCTGCTGGGCGGCAAGGCCGCTCTGACAATTAGCGGAGCCCAGCCTGAGG

ACGAAGCCGAGTACTATTGCGCTCTGTGGTACTCCAACCACTGGGTGTTC

GGCGGCGGCACCAAGCTGACTGTGCTG

Encoded Amino Acid Sequence: (109 aa)

(SEQ ID NO: 12)
QAVVTQEPSLTVSPGGTVTLTCGSSTGAVTTSNFPNWVQQKPGQAPRSLI

GGTNNKASWTPARFSGSLLGGKAALTISGAQPEDEAEYYCALWYSNHWVF

GGGTKLTVL (3) The Heavy and Light Chain Sequences of the Humanized Monoclonal Antibody 4G10H4L3
Nucleic Acid Sequence of the Heavy Chain Variable Region: (345 bp)

(SEQ ID NO: 13)
CAGGTGCAGCTGGTCGAGTCTGGGGCCGAAGTGAAGAAACCCGGCGCCTC

AGTGAAGGTCAGCTGCAAGGCCAGCGGGTACAGTTTCACTGGATATACCA

TGAACTGGGTCCGACAGGCCCCTGGCCAGGGGCTGGAGTGGATCGGCCTG

ATTAACCCTTACAACGACATCACTAACTACGCACAGAAGTTCCAGGGGAG

AGTGACCTTTACAGTGGACACCAGCATTTCCACAGCCTACATGGAACTGT

CCCGGCTGAGATCTGACGATACAGGCGTGTACTTCTGCGCTAGGCTGGAT

TACCGCAGCTATTGGGGACAGGGCACACTGGTGACTGTCAGCGCA

Encoded Amino Acid Sequence: (115 aa)

(SEQ ID NO: 14)
QVQLVESGAEVKKPGASVKVSCKASGYSFTGYTMNWVRQAPGQGLEWIGL

INPYNDITNYAQKFQGRVTFTVDTSISTAYMELSRLRSDDTGVYFCARLD

YRSYWGQGTLVTVSA

The nucleic acid and encoded amino acid sequences of the light chain variable region are the same as those of 4G10H3L3.

2. Preparation of Humanized Antibodies 4G10H1L1, 4G10H3L3 and 4G10H4L3

The constant region of heavy chain was Ig gamma-1 chain C region, ACCESSION: P01857. The constant region of light chain was Ig kappa chain C region, ACCESSION: P01834.

Figure 2:
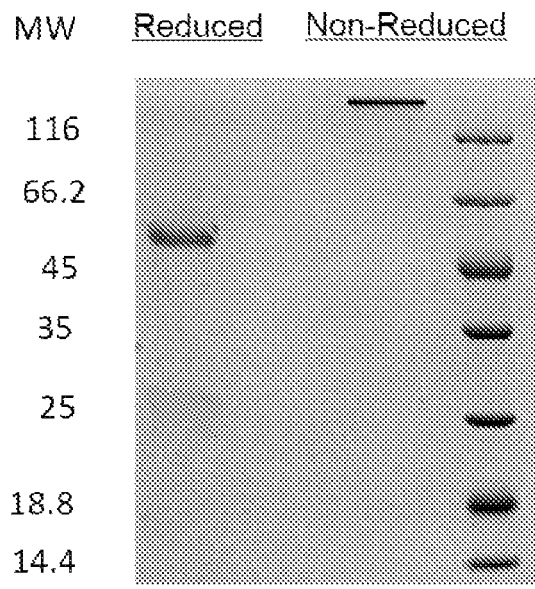
FIG. 2 SDS-PAGE Results of Monoclonal Antibody 4G10H1L1. From left to right: 1 μg antibody in non-reduced loading buffer; 1 μg antibody in reduced loading buffer; 5 μL Marker.
Figure 3:
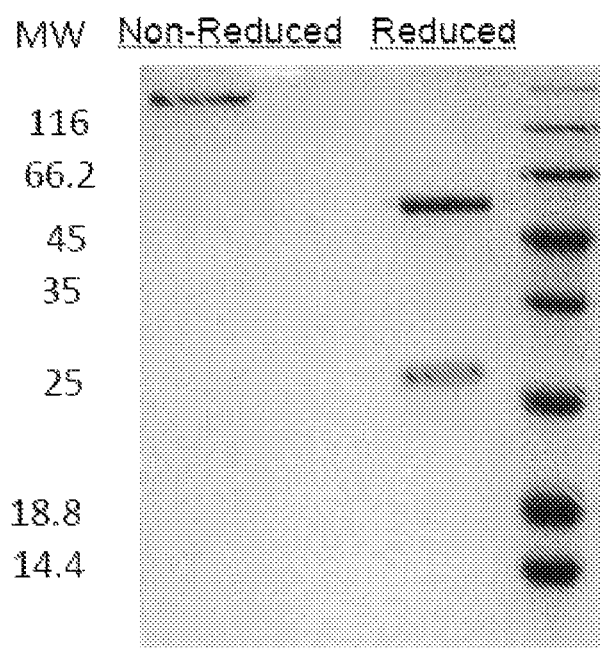
FIG. 3 SDS-PAGE Results of Monoclonal Antibody 4G10H3L3. From left to right: 1 μg antibody in reduced loading buffer; 5 μL Marker.

The heavy chain cDNAs and light chain cDNAs of 4G10H1L1, 4G10H3L3, 4G10H4L3 were separately cloned into pUC57simple vectors to obtain pUC57simple-4G10H1 and pUC57simple-4G10L1, pUC57simple-4G10H3 and pUC57simple-4G10L3, and pUC57simple-4G10H4 and pUC57simple-4G10L3, respectively. They were subcloned into pcDNA3.1 vectors. The recombinant plasmids were transfected into 293F cells and the culture medium was harvested and purified to obtain humanized antibodies 4G10H1L1, 4G10H3L3 and 4G10H4L3. The purified 4G10H1L1 and 4G10H3L3 were identified by SDS-PAGE electrophoresis, and the result was shown in FIG. 2 and FIG. 3 respectively.

Example 4: Preparation of Anti-PD-1 Antibody 14C12

1. Establishment of Hybridoma Cell Line LT003

Using PD-1-mFc as the antigen, the hybridoma cells were obtained by fusing the splenocytes of immunized BALB/C mice (purchased from Guangdong Medical Laboratory Animal Center) and mice myeloma cells with currently established method (for example, Stewart, S. J., "Monoclonal Antibody Production", in Basic Methods in antibody Production and Characterization, Eds. G. C. Howard and D. R. Bethell, Boca Raton: CRC Press, 2000).

Microplate was coated with PD-1-mFc as the antigen, and indirect ELISA was used to screen those hybridoma cells secreting new antibodies specifically binding to PD-1.

The hybridoma cells were further screened by competitive ELISA to select those secreting antibodies that competitively bind to PD-1 against ligand PDL1-hFc (PDL1 Genbank ID:NP_054862.1), and then a stable hybridoma cell line LT003(PD-1-14C12) was obtained by limited dilution method, and its secreted monoclonal antibody is named 14C12.

LT003 (PD-1-14C12), a hybridoma cell line, was deposited in China Center for Type Culture Collection (CCTCC) on Jun. 16, 2015. Deposit Accession NO.: C2015105, depository address: Wuhan university, Wuhan, China, zip code: 430072.

2. Preparation of Anti-PD-1 Antibody 14C12

The LT003 cells in the present invention were cultured using IMDM medium containing 10% low IgG fetal bovine serum (IMDM medium containing 1% streptomycin, cultured in cell incubator with 5% CO$_2$, 37° C. incubator), and after 7 days culture the cell culture supernatant was harvested and purified to get the antibody 14C12.

Example 5: Acquisition of the Sequence of Antibody 14C12

Acquisition of the Sequence of Antibody 14C12 mRNA was extracted from the hybridoma cell line LT003 prepared in Example 4 above according to the manual of the cell/bacterial total RNA extraction reagent kit (Tiangen, Product No. DP430).

cDNA was synthesized using Invitrogen SuperScript® III First-Strand Synthesis System for RT-PCR, and amplified by PCR.

TA cloning was directly carried out on the PCR amplified product according to the instructions of pEASY-T1 Cloning Kit (Transgen CT101).

The products of TA cloning were directly sequenced, and the sequencing results were as follows:

Nucleic Acid Sequence of Heavy Chain Variable Region: (354 bp)

(SEQ ID NO: 15)
GAGGTCAAACTGGTGGAGAGCGGCGGCGGGCTGGTGAAGCCCGGCGGGTC

ACTGAAACTGAGCTGCGCCGCTTCCGGCTTCGCCTTTAGCTCCTACGACA

TGTCATGGGTGAGGCAGACCCCTGAGAAGCGCCTGGAATGGGTCGCTACT

ATCAGCGGAGGCGGGCGATACACCTACTATCCTGACTCTGTCAAAGGGAG

-continued
ATTCACAATTAGTCGGGATAACGCCAGAAATACTCTGTATCTGCAGATGT

CTAGTCTGCGGTCCGAGGATACAGCTCTGTACTATTGTGCAAACCGGTAC

GGCGAAGCATGGTTTGCCTATTGGGGACAGGGCACCCTGGTGACAGTCTC

TGCC

Encoded Amino Acid Sequence: (118 aa)

(SEQ ID NO: 16)
EVKLVESGGGLVKPGGSLKLSCAASGFAFSSYDMSWVRQTPEKRLEWVAT

ISGGGRYTYYPDSVKGRFTISRDNARNTLYLQMSSLRSEDTALYYCANRY

GEAWFAYWGQGTLVTVSA

Nucleic Acid Sequence of the Light Chain Variable Region: (318 bp)

(SEQ ID NO: 17)
GACATTAAGATGACACAGTCCCCTTCCTCAATGTACGCTAGCCTGGGCGA

GCGAGTGACCTTCACATGCAAAGCATCCCAGGACATCAACACATACCTGT

CTTGGTTTCAGCAGAAGCCAGGCAAAAGCCCCAAGACCCTGATCTACCGG

GCCAATAGACTGGTGGACGGGGTCCCCAGCAGATTCTCCGGATCTGGCAG

TGGGCAGGATTACTCCCTGACCATCAGCTCCCTGGAGTATGAAGACATGG

GCATCTACTATTGCCTGCAGTATGATGAGTTCCCTCTGACCTTTGGAGCA

GGCACAAAACTGGAACTG

Encoded Amino Acid Sequence: (106 aa)

(SEQ ID NO: 18)
DIKMTQSPSSMYASLGERVTFTCKASQDINTYLSWFQQKPGKSPKTLIYR

ANRLVDGVPSRFSGSGSGQDYSLTISSLEYEDMGIYYCLQYDEFPLTFGA

GTKLEL

Example 6: Design, Preparation and Assay of Humanized Antibody 14C12H1L1 Against PD-1

1. Design of the Light and Heavy Chain Sequences of the Humanized Antibody 14C12H1L1

Based on the three-dimensional crystal structure of PD-1 protein (Shinohara T, et al., Structure and chromosomal localization of the human PD-1 gene (PDCD1). Genomics 1995, 23 (3): 704-6) and the amino acids sequence of antibody 14C12 obtained in the Example 5, antibody in silico modeling was performed and mutations of amino acids from mouse-like to human-like were engineered to obtain the amino acid sequences of variable regions of antibody 14C12H1L1.

The designed sequences of variable regions are as follows:

Nucleic Acid Sequence of the Heavy Chain Variable Region: (354 bp)

(SEQ ID NO: 19)
GAAGTGCAGCTGGTCGAGTCTGGGGGAGGGCTGGTGCAGCCCGGCGGGTC

ACTGCGACTGAGCTGCGCAGCTTCCGGATTCGCCTTTAGCTCCTACGACA

TGTCCTGGGTGCGACAGGCACCAGGAAAGGGACTGGATTGGGTCGCTACT

-continued

ATCTCAGGAGGCGGGAGATACACCTACTATCCTGACAGCGTCAAGGGCCG

GTTCACAATCTCTAGAGATAACAGTAAGAACAATCTGTATCTGCAGATGA

ACAGCCTGAGGGCTGAGGACACCGCACTGTACTATTGTGCCAACCGCTAC

GGGGAAGCATGGTTTGCCTATTGGGGGCAGGGAACCCTGGTGACAGTCTC

TAGT

Encoded Amino Acid Sequence: (118 aa)

(SEQ ID NO: 20)
EVQLVESGGGLVQPGGSLRLSCAASGFAFSSYDMSWVRQAPGKGLDWVAT

ISGGGRYTYYPDSVKGRFTISRDNSKNNLYLQMNSLRAEDTALYYCANRY

GEAWFAYWGQGTLVTVSS

Nucleic Acid Sequence of the Light Chain Variable Region: (321 bp)

(SEQ ID NO: 21)
GACATTCAGATGACTCAGAGCCCCTCCTCCATGTCCGCCTCTGTGGGCGA

CAGGGTCACCTTCACATGCCGCGCTAGTCAGGATATCAACACCTACCTGA

GCTGGTTTCAGCAGAAGCCAGGGAAAAGCCCCAAGACACTGATCTACCGG

GCTAATAGACTGGTGTCTGGAGTCCCAAGTCGGTTCAGTGGCTCAGGAG

CGGACAGGACTACACTCTGACCATCAGCTCCCTGCAGCCTGAGGACATGG

CAACCTACTATTGCCTGCAGTATGATGAGTTCCCACTGACCTTTGGCGCC

GGGACAAAACTGGAGCTGAAG

Encoded Amino Acid Sequence: (107 aa)

(SEQ ID NO: 22)
DIQMTQSPSSMSASVGDRVTFTCRASQDINTYLSWFQQKPGKSPKTLIYR

ANRLVSGVPSRFSGSGSGQDYTLTISSLQPEDMATYYCLQYDEFPLTFGA

GTKLELK

2. Preparation and SDS-PAGE Electrophoresis of Humanized Antibody 14C12H1L1

The constant region of heavy chain is Ig gamma-1 chain C region, ACCESSION: P01857; and the constant region of light chain is Ig kappa chain C region, ACCESSION: P01834.

Figure 4:
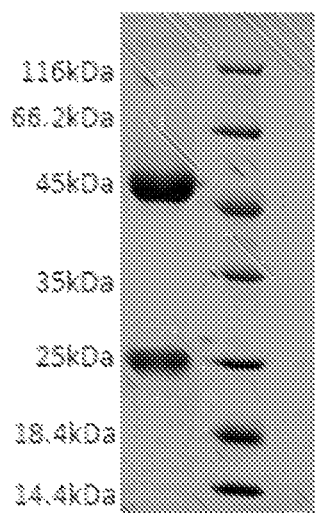
FIG. 4 SDS-PAGE Results of Monoclonal Antibody 14C12H1L1. From left to right: 1 μg antibody in non-reduced loading buffer; 1 μg antibody in reduced loading buffer; 5 μL Marker; 1 μg BSA.

The heavy chain cDNA and light chain cDNA of 14C12H1L1 were separately cloned into pcDNA3.1 vector to obtain the recombinant expression plasmids. The recombinant plasmids were transfected into 293F cells. The 293F cell culture medium was purified and tested. As shown in FIG. 4, the reduced target protein appeared at approximately 24.5 kD and 49 kD, while the non-reduced target protein appeared at approximately 147 kD.

Example 7: Sequence Design, Expression and Assay of Heavy Chains and Light Chains of Bispecific Antibody BiAb001, BiAb002, BiAb003, BiAb004, BiAb007 and BiAb010

1. Sequence Design

Bispecific antibody BiAb001, BiAb002, BiAb003, BiAb004, BiAb007 and BiAb010 in the present invention all belong to Morrison design (IgG-scFv), in which each heavy chain of an IgG antibody are connected with a scFv fragment of another antibody. The configurations of the heavy chains and light chains are shown in Table 1 below.

TABLE 1

The configurations of BiAb001, BiAb002, BiAb003, BiAb004, BiAb007 and BiAb010 heavy chains and light chains

| Bispecific Antibody | Heavy chains | | | Light chains |
|---|---|---|---|---|
| | IgG | Linker fragment | scFv | |
| BiAb001 | 14C12H1 | Linker 1 | 4G10H1v-Linker 2-4G10L1v | 14C12L1 |
| BiAb002 | 14C12H1 | Linker 2 | 4G10H1v-Linker 2-4G10L1v | 14C12L1 |
| BiAb003 | 14C12H1 | Linker 1 | 4G10H3v-Linker 2-4G10L3v | 14C12L1 |
| BiAb004 | 14C12H1 | Linker 2 | 4G10H3v-Linker 2-4G10L3v | 14C12L1 |
| BiAb007 | 14C12H1 | Linker 2 | 4G10H4v-Linker 2-4G10L3v | 14C12L1 |
| BiAb010 | 14C12H1 | Linker 2 | 8D2H14v-Linker 2-8D2L2v | 14C12L1 |

In Table 1:

(1) The antibody sequences marked with subscript "V" refer to the variable region of heavy chains or light chains. Those with no subscript "V" are full-length heavy chains or light chains with constant region. These variable regions or full-length sequences of amino acids and their coding nucleic acid sequences embody the corresponding sequences recorded in the examples above.

(2) Linker 1 Amino Acid Sequence is (GGGGS)3 (SEQ ID NO: 23)

Linker 2 amino acid sequence is (GGGGS)4 (SEQ ID NO: 24)

(3) Amino Acid Sequence of the Heavy Chain Variable Region of 8D2H14L2 (8D2H14v):

(SEQ ID NO: 25)
EVQLVESGGGLVQPGGSSRLSCAASGFTFSDNWMNWVRQAPGKGLEWLAQ

IRNKPYNYETYYSASVKGRFTISRDDSKNSVYLQMNSLKTEDTGVYYCTA

QFAYWGQGTLVTVSS

Encoded Nucleic Acid Sequence of 8D2H14v:

(SEQ ID NO: 26)
GAGGTGCAGCTGGTCGAATCTGGAGGAGGACTGGTGCAGCCTGGAGGAAG

CTCCCGGCTGTCATGTGCCGCTAGCGGCTTCACCTTTTCCGACAACTGGA

TGAATTGGGTGCGACAGGCACCAGGCAAAGGACTGGAGTGGCTGGCTCAG

ATCCGGAACAAGCCCTACAATTATGAAACATACTATAGCGCCTCCGTGAA

AGGCCGGTTCACTATTAGTAGAGACGATTCTAAGAACAGCGTGTACCTGC

AGATGAATAGCCTGAAGACAGAGGATACTGGCGTCTACTATTGCACAGCA

CAGTTTGCCTATTGGGGACAGGGCACCCTGGTGACAGTCTCTAGT (4) Amino Acid Sequence of the Light Chain Variable Region of 8D2H14L2 (8D2L2v):

(SEQ ID NO: 27)
DIQMTQSPSSLSASVGDRVTITCRTSENIYGGLNWYQRKPGKSPKLLIYG

ATNLASGVSSRFSGSGSGTDYTLTISSLQPEDVATYYCQNVLRSPFTFGS

GTKLEIK

Encoded Nucleic Acid Sequence of 8D2L2v:

(SEQ ID NO: 28)
GACATCCAGATGACTCAGAGCCCCTCAAGCCTGTCTGCAAGTGTGGGCGA

TAGGGTCACCATCACATGTCGCACCTCCGAAAACATCTACGGGGACTGA

ATTGGTATCAGCGCAAGCCCGGCAAATCCCCTAAGCTGCTGATCTACGGC

GCTACCAACCTGGCATCTGGGGTGTCCTCTCGATTTTCAGGGAGCGGCAG

CGGCACCGACTATACTCTGACCATTAGTTCACTGCAGCCTGAGGATGTGG

CCACATACTATTGCCAGAATGTCCTGAGATCACCATTCACTTTTGGGAGC

GGAACCAAACTGGAAATTAAG

2. Expression and Purification of Antibody BiAb001 cDNAs of heavy chain and light chain of BiAb001 were separately cloned into pUC57simple vectors (provided by GenScript) to obtain plasmids pUC57simple-BiAb001H and pUC57simple-BiAb001L, respectively.

pUC57simple-BiAb001H and pUC57simple-BiAb001L were individually digested with enzymes (HindIII&EcoRI), and genes of heavy chain and light chain recovered via electrophoresis were sub-cloned into pcDNA3.1 vector, respectively. The recombinant plasmids were extracted and co-transfected into 293F cells. After 7 days culture, the culture supernatant was harvested by high-speed centrifugation and concentration, and purified by loading onto HiTrap protein A HP column and eluting with Elution Buffer in one step to obtain the antibody and stored in PBS.

Figure 5:
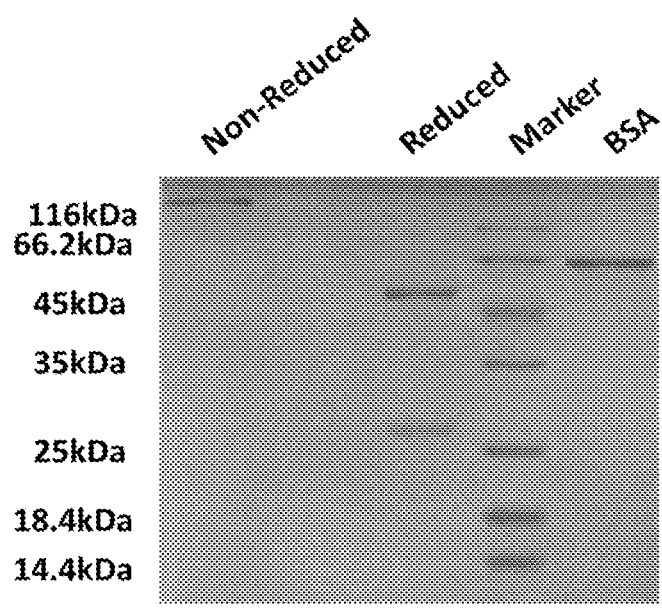
FIG. 5 SDS-PAGE Results of Bispecific Antibody BiAb001. From left to right: 5 μL Marker; 1 μg antibody in non-reduced loading buffer; 1 μg antibody in reduced loading buffer; 1 μg BSA.
Figure 6:
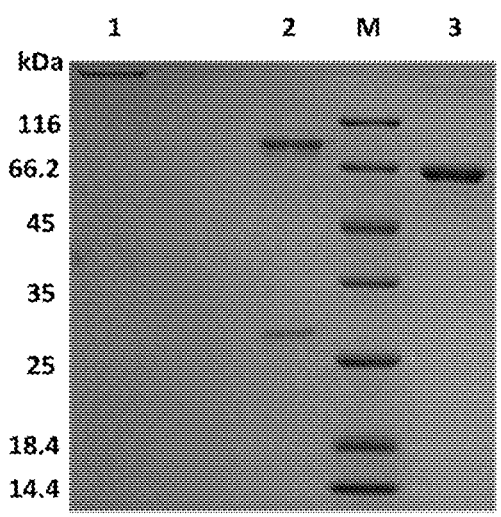
FIG. 6 SDS-PAGE Results of Bispecific Antibody BiAb002. From left to right: 5 μL Marker; 1 μg antibody in non-reduced loading buffer; 1 μg antibody in reduced loading buffer; 1 μg BSA.
Figure 7:
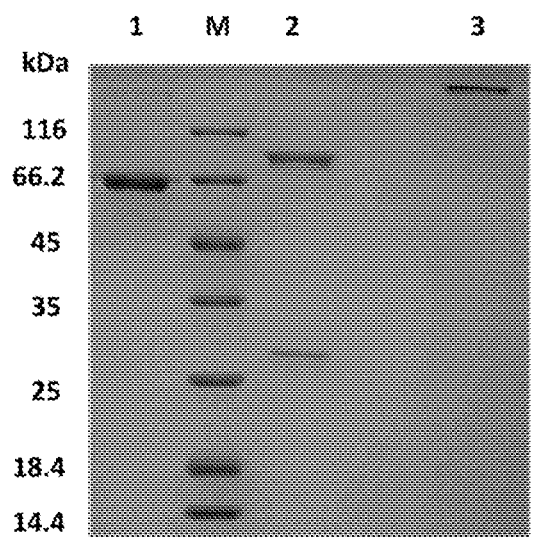
FIG. 7 SDS-PAGE Results of Bispecific Antibody BiAb003. From left to right: 5 μL Marker; 1 μg antibody in non-reduced loading buffer; 1 μg antibody in reduced loading buffer; 1 μg BSA.
Figure 8:
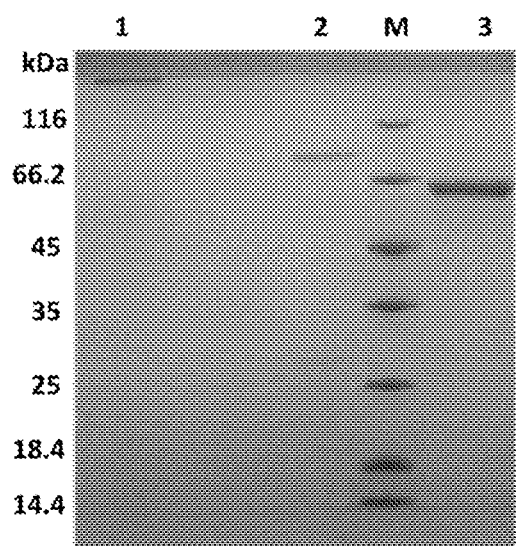
FIG. 8 SDS-PAGE Results of Bispecific Antibody BiAb004. From left to right: 5 μL Marker; 1 μg antibody in non-reduced loading buffer; 1 μg antibody in reduced loading buffer; 1 μg BSA.
Figure 9:
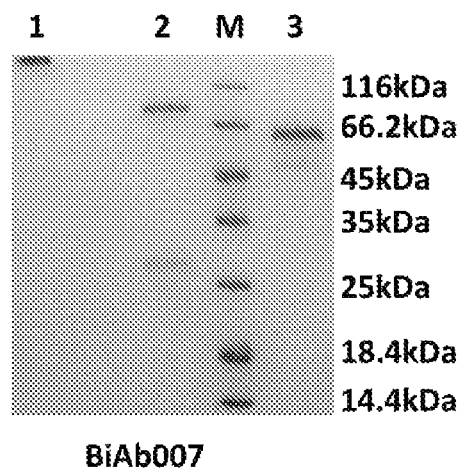
FIG. 9 SDS-PAGE Results of Bispecific Antibody BiAb007. From left to right: 5 μL Marker; 1 μg antibody in non-reduced loading buffer; 1 μg antibody in reduced loading buffer; 1 μg BSA.
Figure 10:
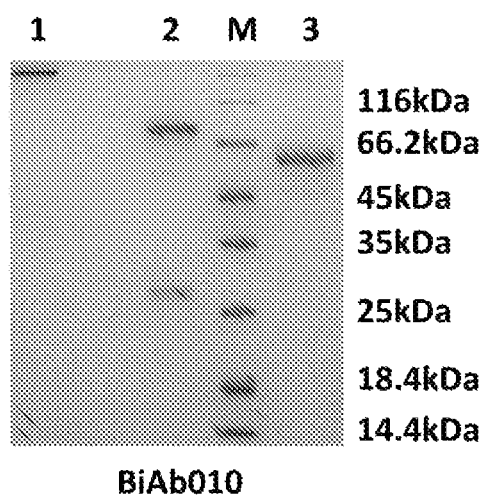
FIG. 10 SDS-PAGE Results of Bispecific Antibody BiAb010. From left to right: 5 μL Marker; 1 μg antibody in non-reduced loading buffer; 1 μg antibody in reduced loading buffer; 1 μg BSA.
Figure 11:
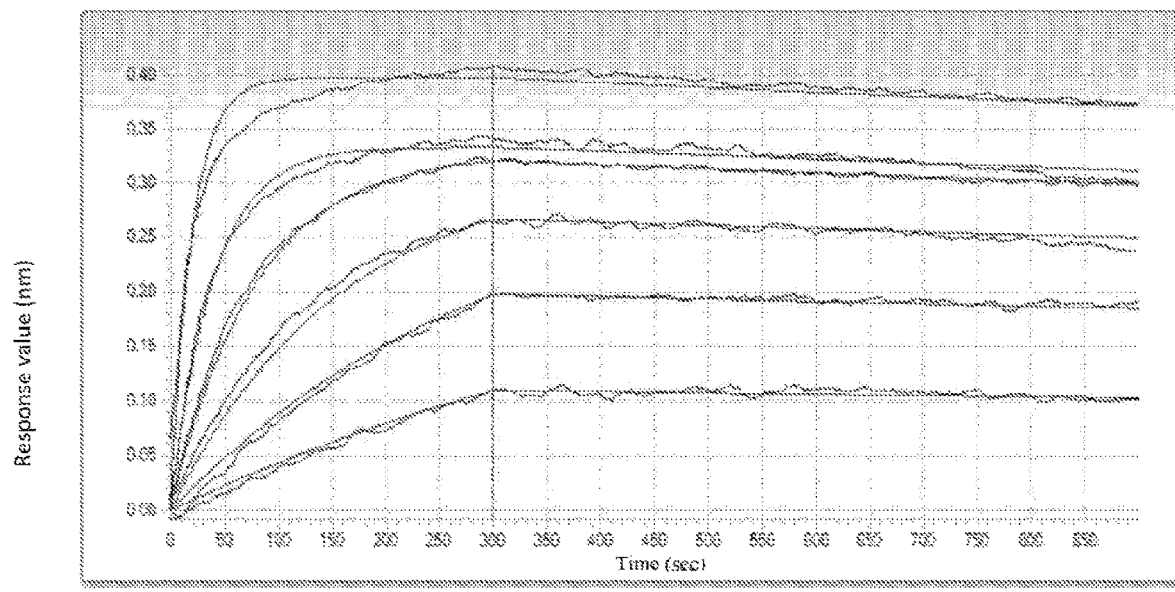
FIG. 11. Binding kinetics of antibody 4G10
FIG. 12. Binding kinetics of antibody 4G10 H1L1
FIG. 13. Binding kinetics of antibody 4G10H3L3
FIG. 14. Binding kinetics of antibody 4G10H4L3
FIG. 15. Binding kinetics of antibody 14C12
FIG. 16. Binding kinetics of antibody 14C12 H1L1
FIG. 17. Binding kinetics of CTLA4 and antibody BiAb001
FIG. 18. Binding kinetics of CTLA4 and antibody BiAb002
FIG. 19. Binding kinetics of CTLA4 and antibody BiAb003
FIG. 20. Binding kinetics of CTLA4 and antibody BiAb004
FIG. 21. Binding kinetics of CTLA4 and antibody BiAb007
FIG. 22. Binding kinetics of PD-1 and antibody BiAb001
FIG. 23. Binding kinetics of PD-1 and antibody BiAb002
FIG. 24. Binding kinetics of PD-1 and antibody BiAb003
FIG. 25. Binding kinetics of PD-1 and antibody BiAb004
FIG. 26. Binding kinetics of PD-1 and antibody BiAb007
FIG. 27. Binding kinetics of PD-1 and antibody BiAb010
Figure 12:
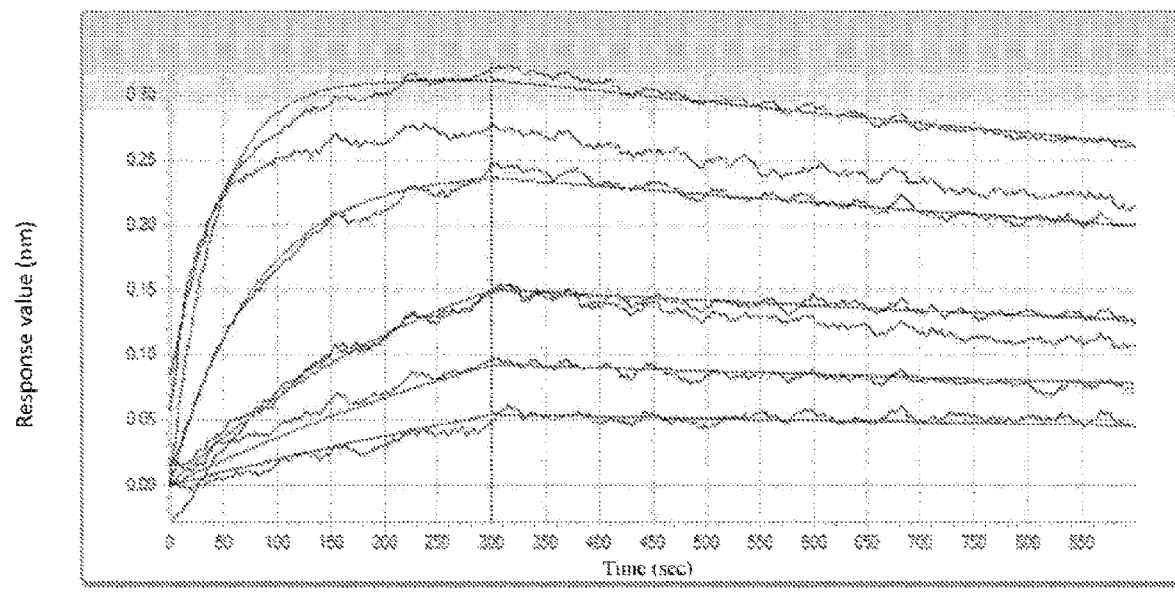
Figure 13:
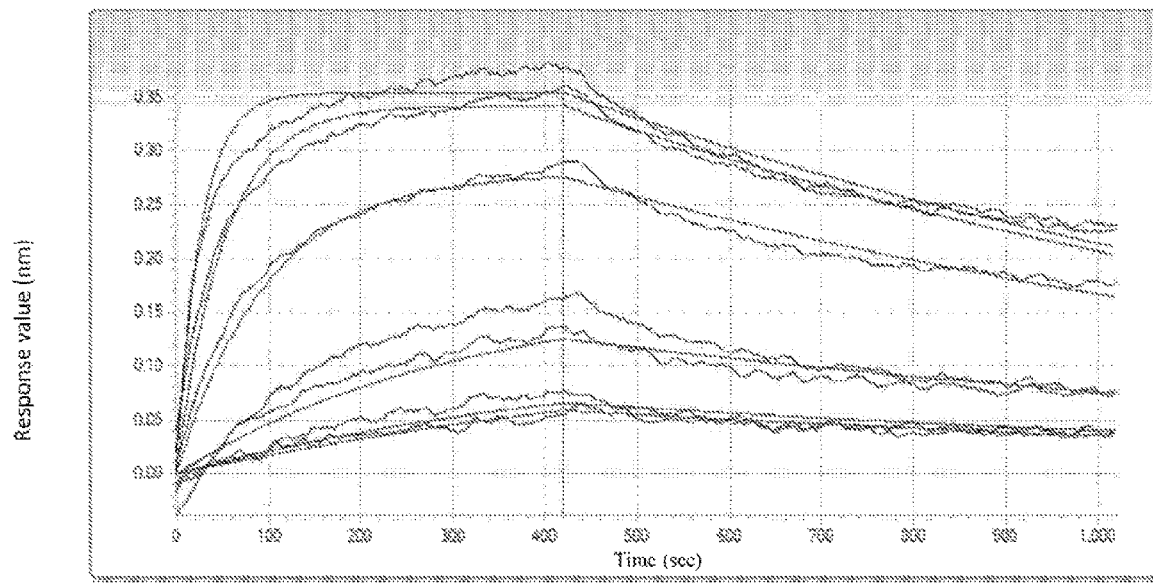
Figure 14:
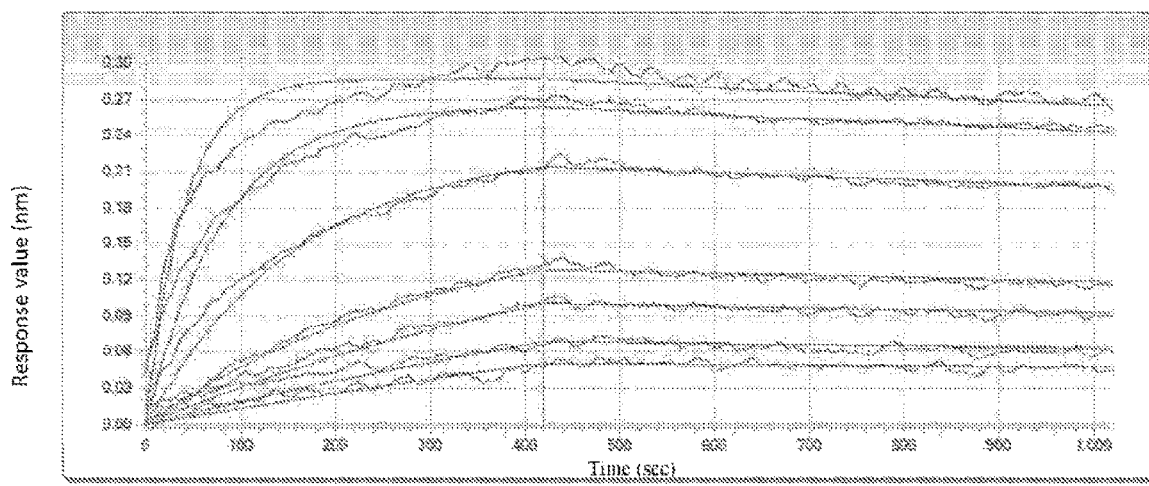

The purified antibody samples were added to reduced protein electrophoresis loading buffer and non-reduced protein electrophoresis loading buffer, respectively. After being boiled, the samples were examined on SDS-PAGE electrophoresis. The results of BiAb001 electrophoresis was shown in FIG. 5, in which the reduced protein sample appeared at 23.6 kD and 75.8 kD, and the non-reduced protein sample (individual antibody) appeared at 199 kD.

3. Expression and Purification of Antibody BiAb002, BiAb003, BiAb004, BiAb007 and BiAb010

Purified antibodies of BiAb002, BiAb003, BiAb004, BiAb007 and BiAb010 were obtained according to the aforementioned methods used for preparation of BiAb001.

The purified antibodies samples were added into of reduced protein electrophoresis loading buffer and non-reduced protein electrophoresis loading buffer, respectively. After being boiled, the samples were examined on SDS-PAGE electrophoresis. The results of BiAb002, BiAb003, BiAb004, BiAb007 and BiAb010 electrophoresis were shown in FIGS. 6, 7, 8, 9 and 10, respectively, in which the reduced protein sample appeared at 23.6 kD and 75.8 kD, and the non-reduced protein sample (individual antibody) appeared at 199 kD.

Example 8: Determination of Antibody Binding Kinetics

The binding kinetics of antigen and antibody were measured by Fortebio molecular interaction instrument.

1. Binding kinetics of antibody 4G10 and its humanized antibody 4G10H1L1, 4G10H3L3, and 4G10H4L3 to antigen CTLA4 were measured 1.1 CTLA4 antigen was obtained by digesting CTLA4-mFc with TEV protease and column purification 1.2 Antibody 4G10 was immobilized to AR2G Biosensors by amine coupling method, and then blocked with ethanolamine and equilibrating in PBST, and then bound to CTLA4. CTLA4 was double gradient diluted with PB ST to the concentrations of 268.1, 134.1, 67, 33.5, 16.8, 8.38, 4.19, and 0 nM. The dissociation was also in PBST. Humanized antibodies 4G10H1L1, 4G10H3L3 and 4G10H4L3 were measured with similar methods to that of 4G10, with antigen concentrations of 180, 90, 45, 22.5, 11.25, 5.625, 2.813 and 0 nM.

1.3 The binding kinetics of antibody 4G10 and its humanized antibodies 4G10H1L1, 4G10H3L3, and 4G10H4L3 to antigen CTLA4 are shown in Table 1 below, and in FIG. 11, FIG. 12, FIG. 13 and FIG. 14, respectively.

2. Binding kinetics of antibody 14C12 and its humanized antibody 14C12H1L1 to antigen PD-1

2.1 PD-1 antigen was obtained by digesting PD-1-mFc with TEV protease and column purification 2.2 The antigen PD-1 (antigen concentration of 1 μg/ml) was immobilized on the surface of SA sensor after being labeled with biotin, and after equilibrating in PBST it bind to antibodies 14C12 and 14C12H1L1, respectively. The antibodies were diluted with PBST from 200 nM down three fold each time, and the dissociation was also in PBST.

Figure 15:
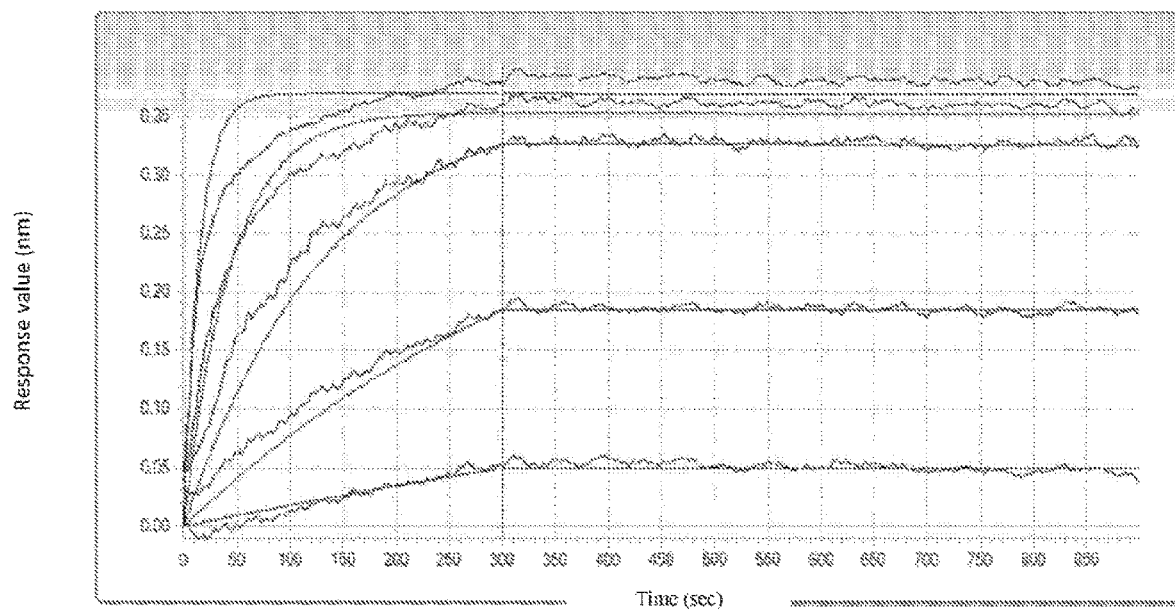
Figure 16:
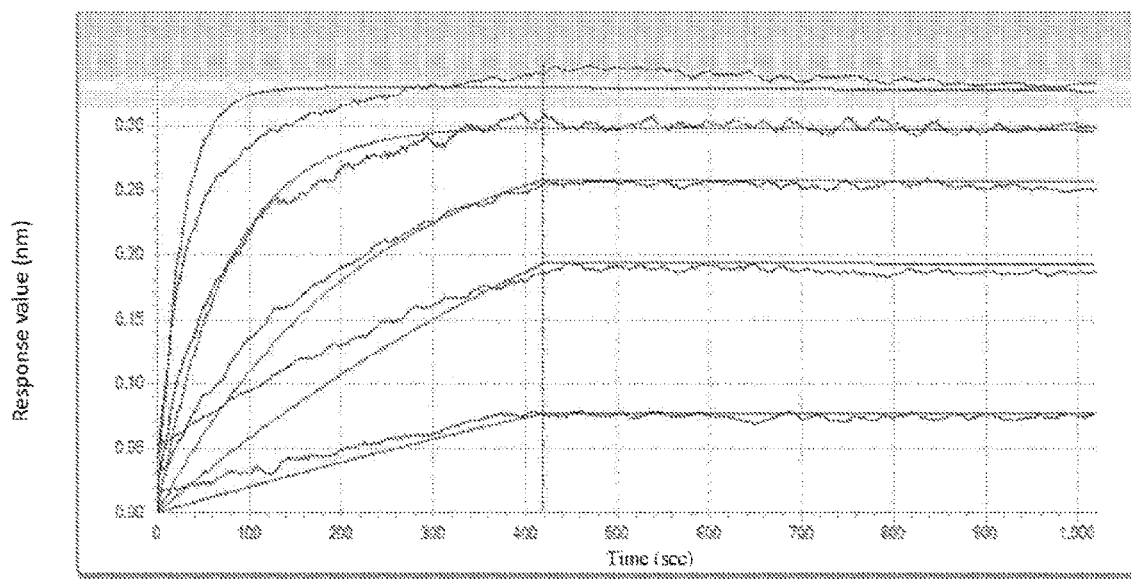
Figure 17:
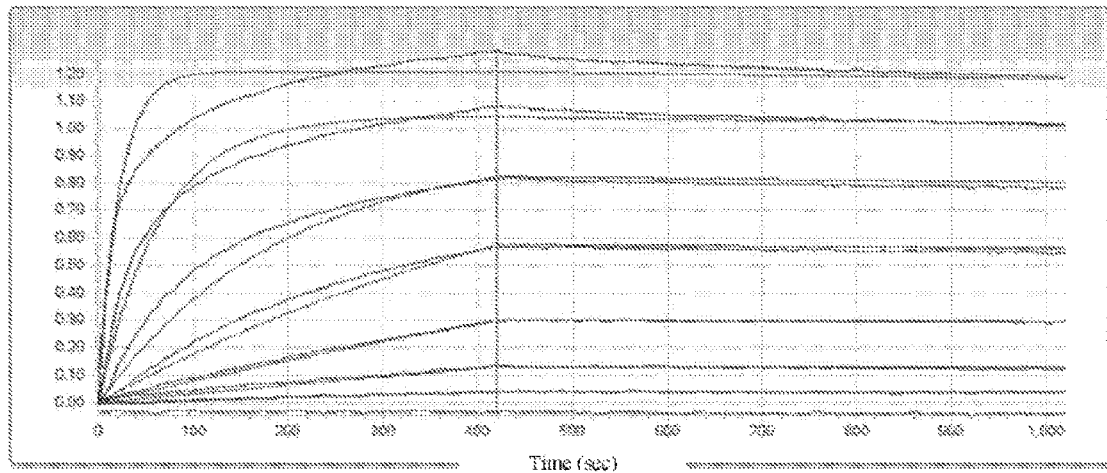
Figure 18:
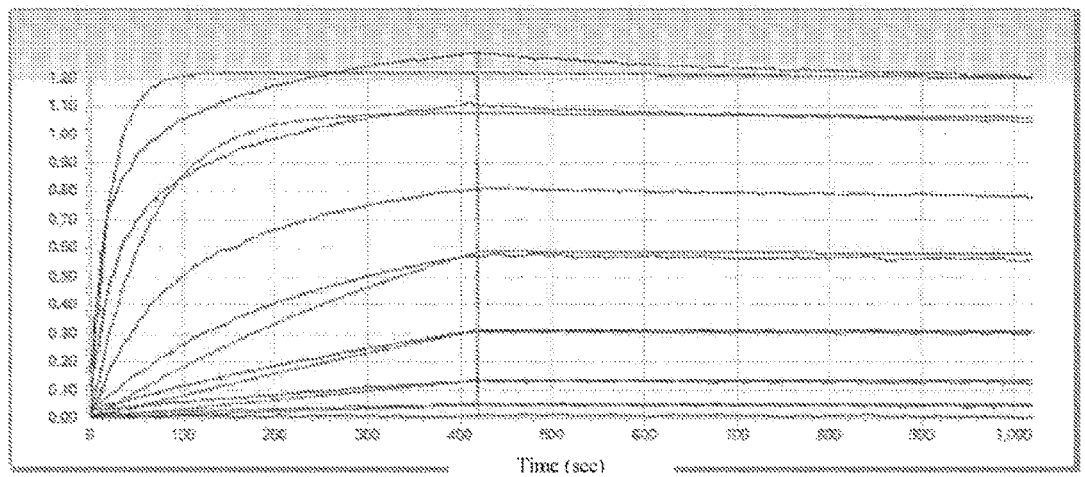
Figure 19:
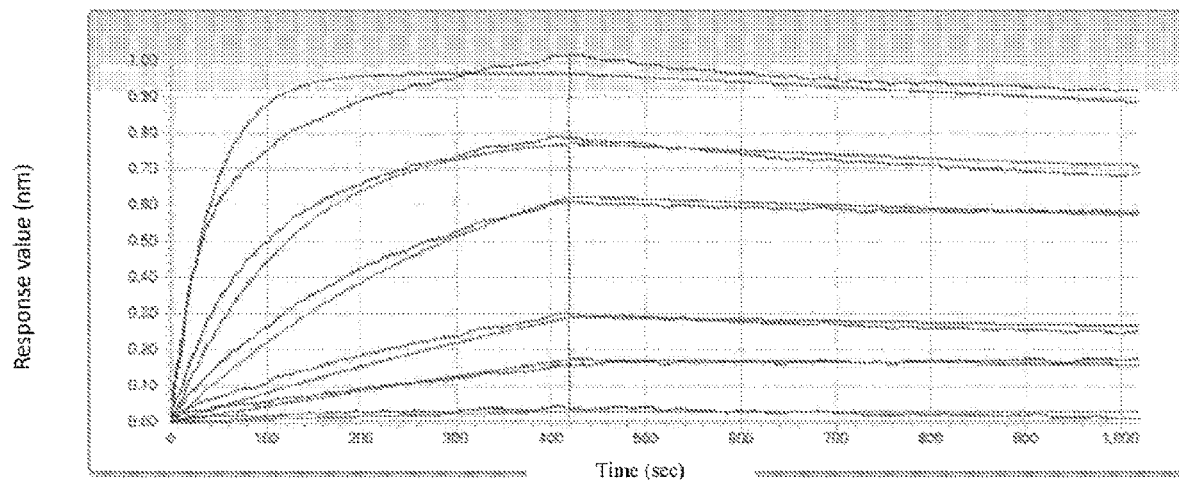
Figure 20:
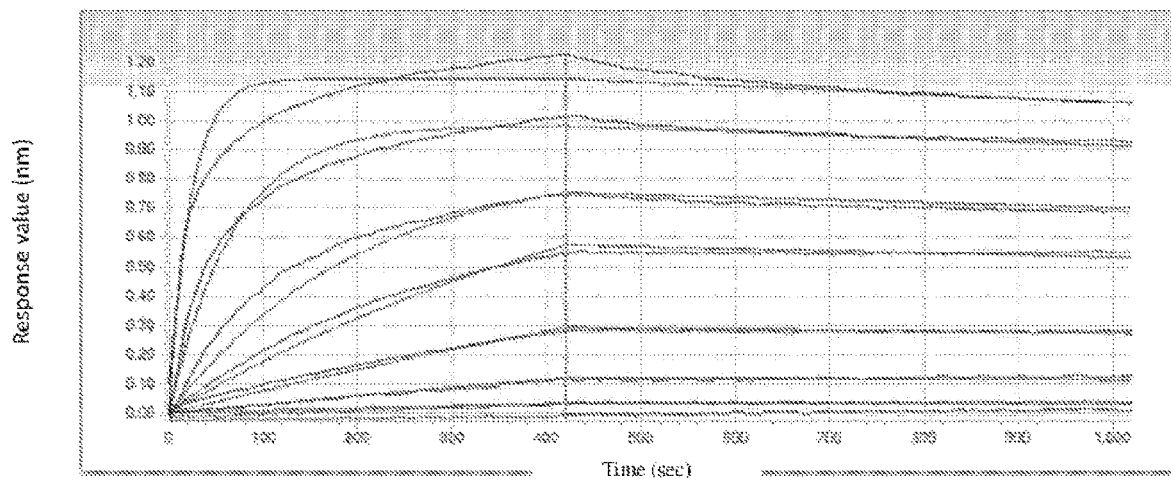
Figure 21:
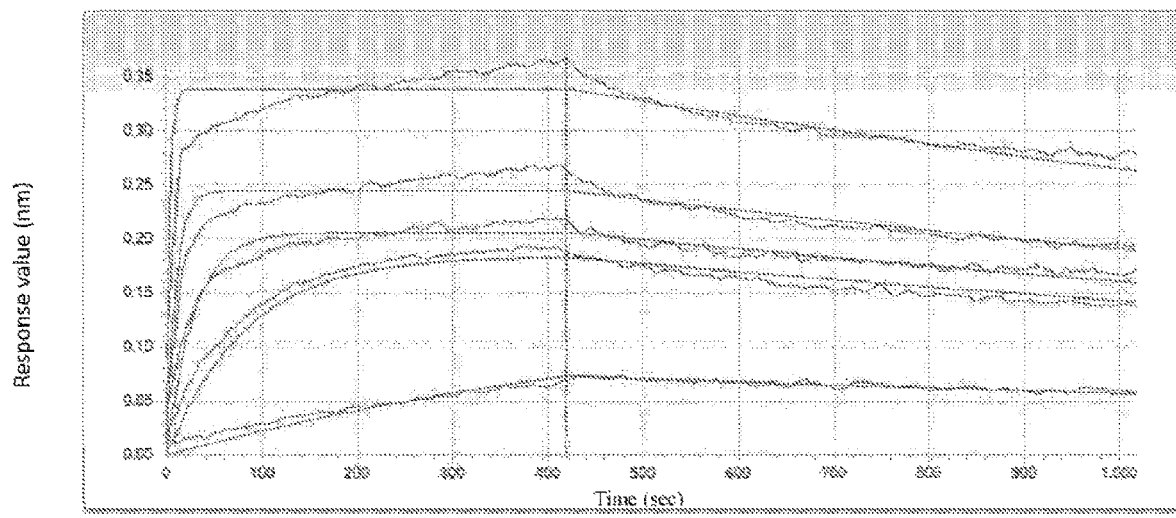
Figure 22:
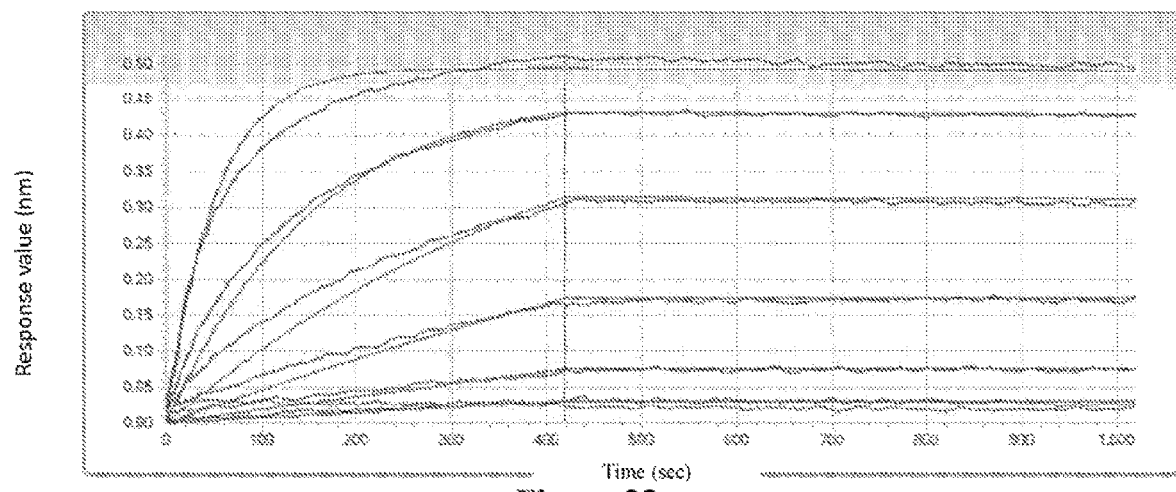
Figure 23:
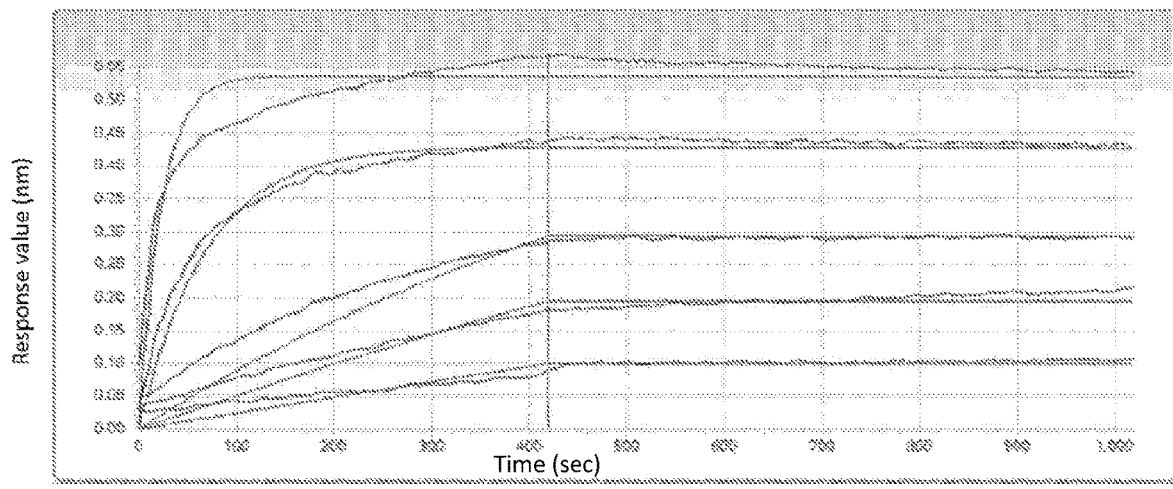
Figure 24:
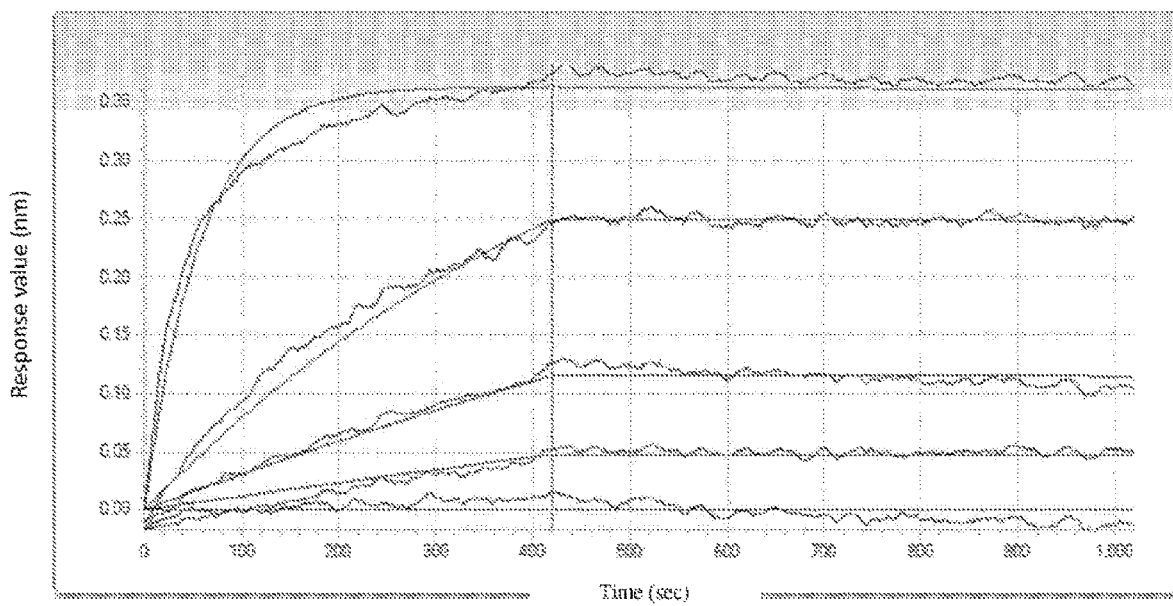
Figure 25:
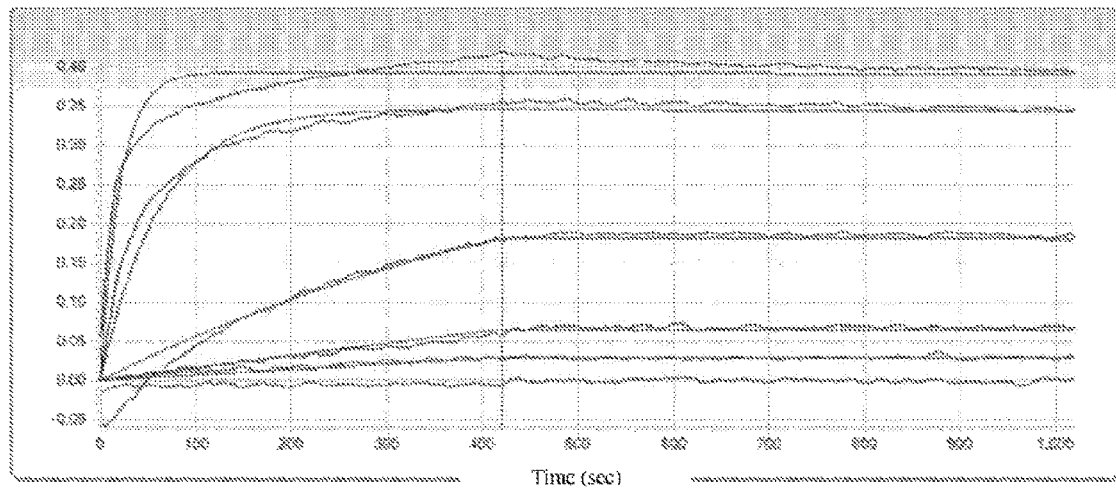
Figure 26:
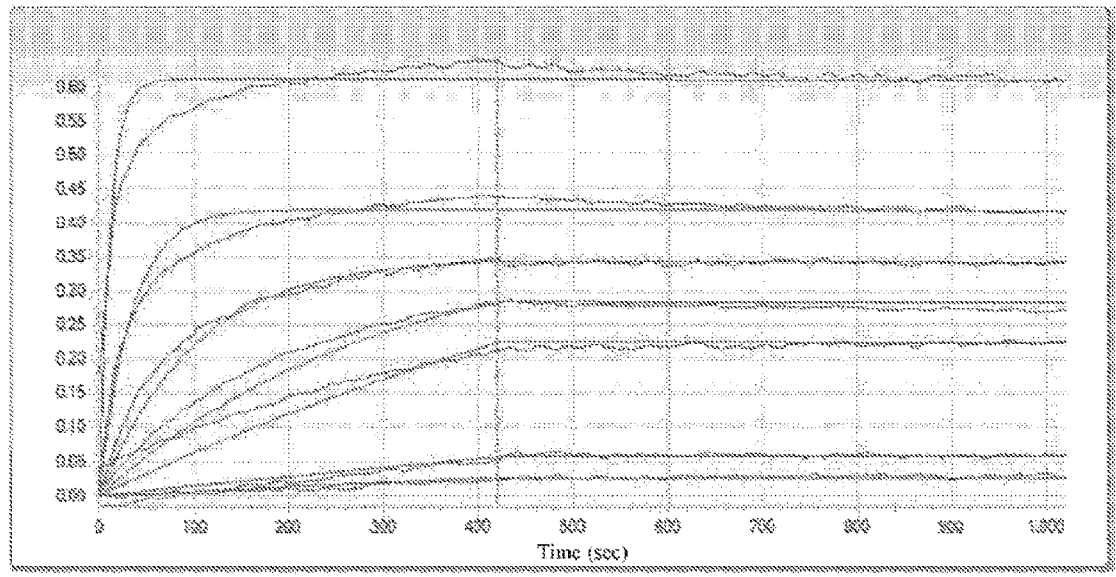
Figure 27:
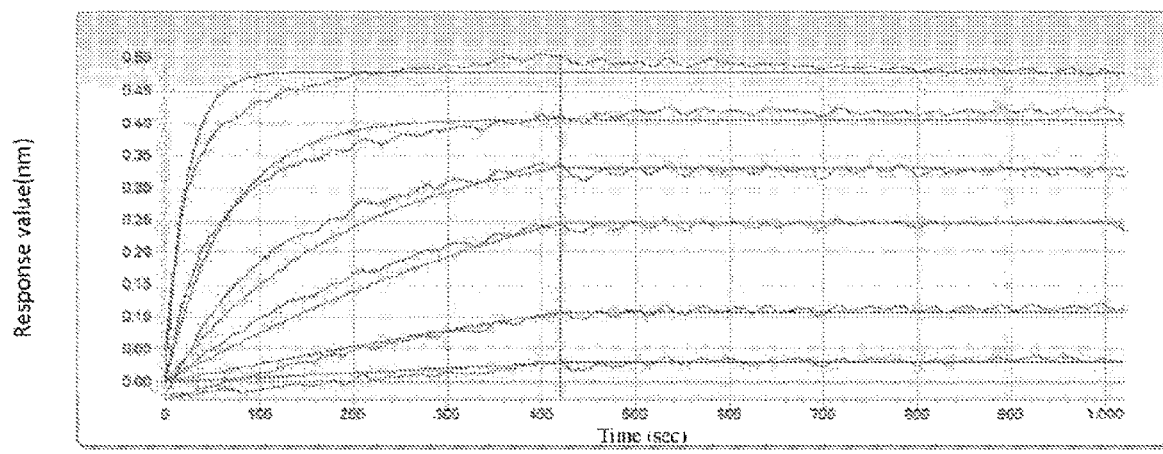

2.3 The binding kinetics of antibodies 14C12 and 14C12H1L1 to antigen are shown in Table 1 below and in FIGS. 15 and 16.

3. Binding kinetics of antibodies BiAb001, BiAb002, BiAb003, BiAb004, BiAb007 and BiAb010 to antigen CTLA4.

3.1 CTLA4 (antigen concentration of 1 μg/ml) was immobilized on the surface of SA sensor after being labeled with biotin, and after equilibrating in PBST, it binds to antibodies BiAb001, BiAb002, BiAb003, BiAb004, BiAb007 and BiAb010, respectively. The antibodies were diluted with PBST from 200 nM down three fold each time. The dissociation was also in PBST.

3.2 Binding kinetics of antibodies BiAb001, BiAb002, BiAb003, BiAb004, BiAb007 and BiAb010 to antigen CTLA4 are shown in Table 1 and in FIGS. 17-21, respectively.

4. Binding kinetics of antibodies BiAb001, BiAb002, BiAb003, BiAb004, BiAb007 and BiAb010 to antigen to antigen PD-1

4.1 The antigen PD-1 (antigen concentration of 1 μg/ml) was immobilized on the surface of SA sensor after being labeled with biotin, and after equilibrating in PBST, it binds to antibodies BiAb001, BiAb002, BiAb003, BiAb004, BiAb007 and BiAb010, respectively. The antibodies were diluted with PBST from 200 nM down three fold each time. The dissociation was also in PBST.

4.2 Binding kinetics of antibodies BiAb001, BiAb002, BiAb003, BiAb004, BiAb007 and BiAb010 to antigen PD-1 are shown in Table 2, and in FIG. 22-FIG. 27, respectively.

TABLE 2

Kinetic parameters of antibody binding to antigen

| Antibody | Antigen | $K_D$ (M) | Kon(1/Ms) | Kon Error | Kdis(1/s) | Kdis Error |
|---|---|---|---|---|---|---|
| 4G10 | CTLA4 | 3.01E−10 | 3.78E+05 | 4.36E+03 | 1.14E−04 | 5.33E−06 |
| 4G10 H1L1 | 1 μg/ml | 1.52E−09 | 1.86E+05 | 3.26E+03 | 2.82E−04 | 9.23E−06 |
| 4G10 H3L3 | | 4.14E−09 | 2.09E+05 | 3.81E+03 | 8.64E−04 | 1.11E−05 |
| 4G10H4L3 | | 9.67E−10 | 1.37E+05 | 2.22E+03 | 1.32E−04 | 8.69E−06 |
| 14C12 | PD-1 | 1.81E−11 | 3.38E+05 | 8.23E+03 | 6.12E−06 | 1.04E−05 |
| 14C12H1L1 | 1 μg/ml | 2.42E−11 | 3.17E+05 | 5.90E+03 | 7.66E−06 | 8.70E−06 |
| BIAb001 | CTLA4 | 1.67E−10 | 2.33E+05 | 4.45E+03 | 3.89E−05 | 8.75E−06 |
| BIAb002 | 1 μg/ml | 9.69E−11 | 2.37E+05 | 5.32E+03 | 2.30E−05 | 9.97E−06 |
| BIAb003 | | 3.95E−10 | 3.60E+05 | 7.10E+03 | 1.42E−04 | 9.99E−06 |
| BIAb004 | | 5.66E−10 | 2.20E+05 | 3.89E+03 | 1.24E−04 | 8.27E−06 |
| BiAb007 | | 2.72E−10 | 1.58E+06 | 5.17E+04 | 4.28E−04 | 1.12E−05 |
| BiAb010 | | 3.22E−10 | 1.08E+06 | 1.99E+04 | 3.47E−04 | 7.28E−06 |
| BIAb001 | PD-1 | 4.16E−11 | 2.97E+05 | 4.96E+03 | 1.24E−05 | 8.36E−06 |
| BIAb002 | 1 μg/ml | 3.33E−11 | 2.20E+05 | 5.93E+03 | 7.32E−06 | 1.15E−05 |
| BIAb003 | | 4.12E−11 | 2.64E+05 | 5.49E+03 | 1.09E−05 | 9.82E−06 |
| BIAb004 | | 4.82E−11 | 2.47E+05 | 5.45E+03 | 1.19E−05 | 9.61E−06 |
| BiAb007 | | 1.40E−11 | 4.52E+05 | 9.23E+03 | 6.30E−06 | 7.85E−06 |
| BiAb010 | | 2.97E−11 | 2.28E+05 | 4.40E+03 | 6.79E−06 | 8.70E−06 |

$K_D$ Is the affinity constant; $K_{on}$ is the association rate of antigen-antibody $K_{dis}$ is the dissociation rate of antigen-antibody; $K_D = K_{dis}/K_{on}$.

The results showed that:

the antibody 4G10 and its humanized antibodies have good affinity to the antigen CTLA4. Both antibodies 14C12 and 14C12H1L1 have good affinity to antigen PD-1.

Bispecific antibodies have good affinity to antigen CTLA4 and PD-1.

Example 9: The Binding Activity of Antibody to Antigen Measured by ELISA

1. The binding activity of humanized antibodies 4G10H1L1 and 4G10H3L3 to antigen CTLA4

1.1 The binding activity of humanized antibodies 4G10H1L1 and 4G10H3L3 to CTLA4 was determined by indirect ELISA.

After incubated with antigen at 4° C. overnight, the microplate was blocked with 1% BSA at 37° C. for 2 h, and then the antibodies were added and incubated at 37° C. for 30 min, and then HRP-labeled secondary antibody (goat anti-human IgG (H+L)) (Jackson, 109-035-088) was added and incubated at 37° C. for 30 min. TMB (Neogen, 308177) was added to react for 5 mins. The absorbance was read at the wavelength of 450 nm in a microplate reader.

Figure 28:
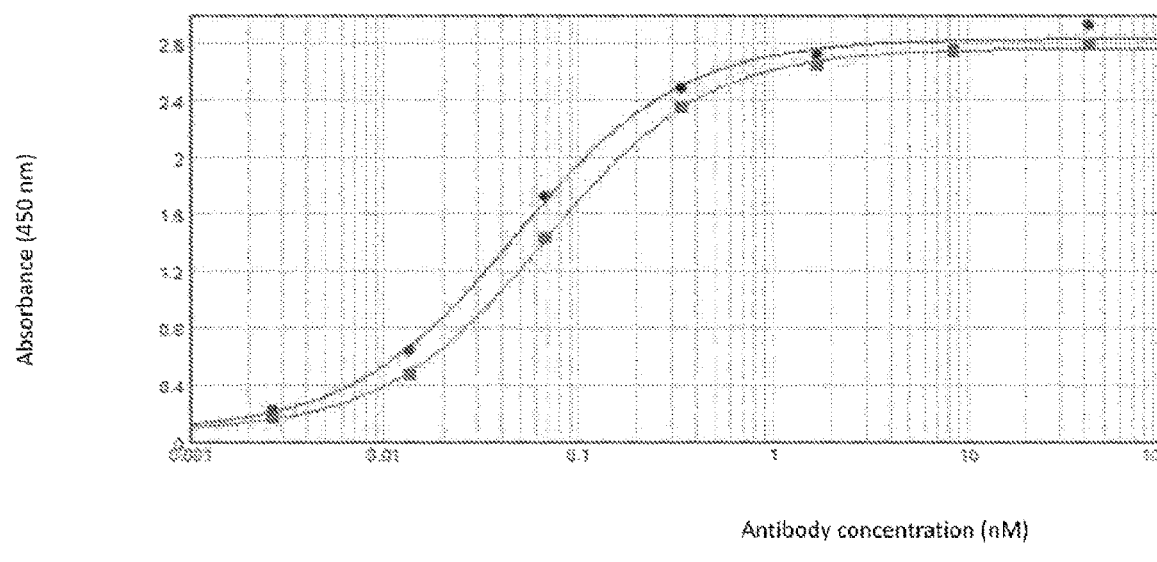
FIG. 28. Indirect ELISA results of 4G10H1L1 and 4G10H3L3 binding to CTLA4.

The binding results were shown in FIG. 28. As shown in the figure, both 4G10H1L1 and 4G10H3L3 can bind to CTLA4 protein effectively with dose-dependency. The absorbance intensities at different doses were shown in Table 3. Through Curve Simulation using quantitative analyses of absorbance values, EC50 of 4G10H1L1 and 4G10H3L3 were then determined to be 0.048 nM and 0.067 nM, respectively.

TABLE 3

The binding activity of 4G10H1L1 and 4G10H3L3 to CTLA4 was measured by indirect ELISA
Coating Antigen: CTLA4 0.5 μg/ml

| Serial dilution of antibody | 4G10 | | H1L1 | | 4G10 H3L3 | |
|---|---|---|---|---|---|---|
| 6 μg/ml | 2.926 | 2.946 | 2.809 | 2.764 | | |
| 1:5 | 2.784 | 2.732 | 2.729 | 2.739 | | |
| 1:25 | 2.729 | 2.688 | 2.668 | 2.617 | | |
| 1:125 | 2.490 | 2.469 | 2.367 | 2.309 | | |
| 1:625 | 1.736 | 1.709 | 1.498 | 1.357 | | |

TABLE 3-continued

The binding activity of 4G10H1L1 and 4G10H3L3 to CTLA4 was measured by indirect ELISA
Coating Antigen: CTLA4 0.5 μg/ml

| Serial dilution of antibody | 4G10 H1L1 | | 4G10 H3L3 | |
|---|---|---|---|---|
| 1:3126 | 0.607 | 0.663 | 0.513 | 0.432 |
| 1:16525 | 0.198 | 0.225 | 0.175 | 0.149 |
| 1:78125 | 0.096 | 0.115 | 0.089 | 0.087 |
| 1:390625 | 0.075 | 0.087 | 0.075 | 0.072 |
| 1:1953125 | 0.071 | 0.090 | 0.066 | 0.077 |
| 1:9765625 | 0.066 | 0.087 | 0.078 | 0.089 |
| 0 | 0.073 | 0.079 | 0.079 | 0.068 |
| Secondary antibody | Goat anti-Human IgG, HRP (1:5000) | | | |

1.2. The binding activity of humanized antibodies 4G10H1L1 and 4G10H3L3 to CTLA4 by competition ELISA against B7

Coating antigen to microplate with B7/1-hFc (B7/1 genbank ID: NP 005182.1) 4° C. overnight, and then after blocked with 1% BSA for 2 hours, mixtures of antibodies and CTLA4-mFc antibody were added (dilute concentrations are shown in table 4) and incubate for 30 min at 37° C.; and then secondary antibody labeled with enzyme was added and then incubated for 30 mins at 37° C. The absorption value of 450 nm was measured on the enzyme-labeled instrument (see table 4).

Figure 29:
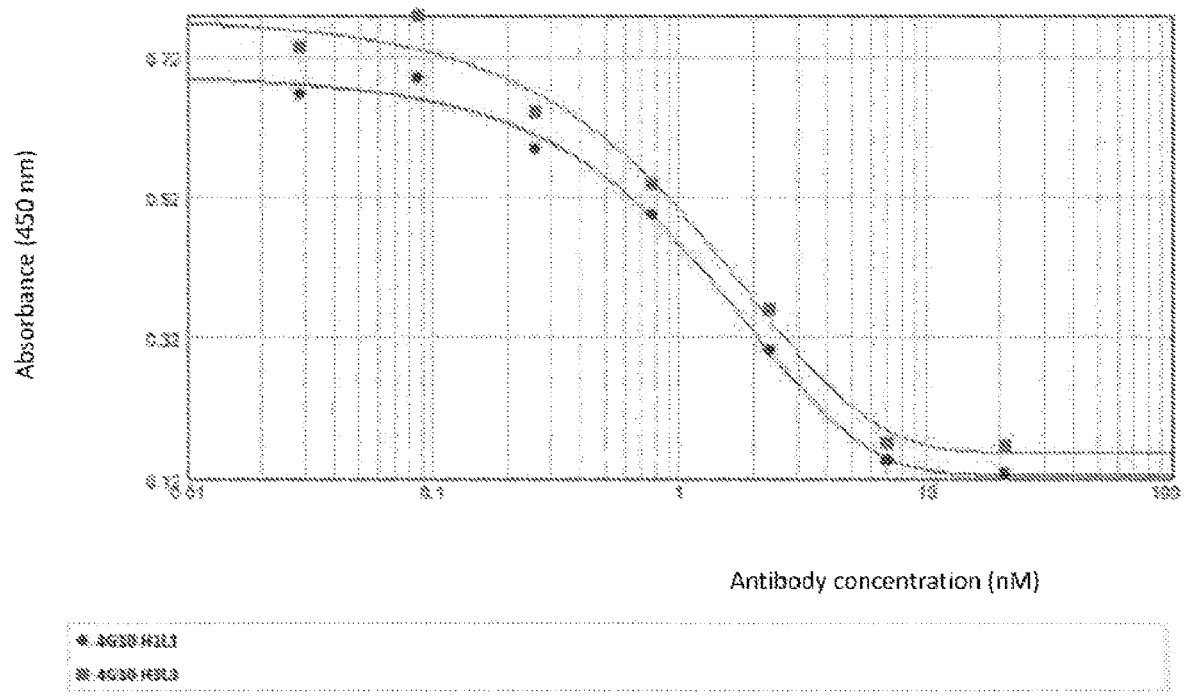
FIG. 29. Competition ELISA results of 4G10H1L1 and 4G10H3L3 binding to CTLA4 against B7.

The binding results of antibodies to CTLA4 competing against B7-1 were shown in FIG. 29. As shown in the figure, the antibodies 4G10H1L1 and 4G10H3L3 can compete against B7-1 and bind to CTLA4 protein effectively with dose-dependency. The absorbance at different doses were shown in Table 4. Through Curve Simulation using quantitative analyses of absorbance values, EC50 of 4G10H1L1 and 4G10H3L3 binding with CTLA4 were then determined to be 1.297 nm and 1.229 nm, respectively.

TABLE 4

The binding activity of humanized antibodies 4G10H1L1 and 4G10H3L3 to CTLA4 by competition ELISA against B7
Coating Antigen: B7/1-hFc 0.5 μg/ml

| Serial dilution of Antibody | 4G10H1L1 | | 4G10H3L3 | | receptor |
|---|---|---|---|---|---|
| 3 μg/ml | 0.132 | 0.121 | 0.146 | 0.185 | CTLA4-mFc |
| 1:3 | 0.120 | 0.170 | 0.159 | 0.182 | 0.3 μg/ml |
| 1:9 | 0.260 | 0.343 | 0.382 | 0.340 | |
| 1:27 | 0.399 | 0.593 | 0.570 | 0.507 | |
| 1:81 | 0.565 | 0.614 | 0.642 | 0.642 | |
| 1:243 | 0.628 | 0.753 | 0.784 | 0.773 | |
| 1:729 | 0.573 | 0.760 | 0.768 | 0.702 | |
| 1:2187 | 0.553 | 0.824 | 0.741 | 0.788 | |
| 1:6561 | 0.661 | 0.844 | 0.824 | 0.679 | |
| 1:19683 | 0.555 | 0.834 | 0.742 | 0.699 | |
| 1:59049 | 0.552 | 0.725 | 0.773 | 0.770 | |
| 0 | 0.610 | 0.665 | 0.822 | 0.717 | |
| Secondary antibody | Goat anti-Mouse IgG, HRP (1:5000) | | | | |

2. The binding activities of monoclonal antibody 14C12 and its humanized antibody 14C12H1L1 to antigen PD-1 measured by ELISA 2.1 The binding activity of monoclonal antibodies 14C12 and 14C12H1L1 to antigen PD-1 was determined by indirect ELISA as follows:

After incubated with PD-1-mFc at 4° C. overnight, the microplate was blocked with 1% BSA at 37° C. for 2 h, and the antibodies were added, incubated at 37° C. for 30 min, and HRP-labeled secondary antibody (goat anti-human IgG (H+L)) (Jackson, 109-035-088) was added and incubated at 37° C. for 30 min. TMB (Neogen, 308177) was added to react for 5 mins. The absorbance was read at the wavelength of 450 nm in a microplate reader.

Figure 30:
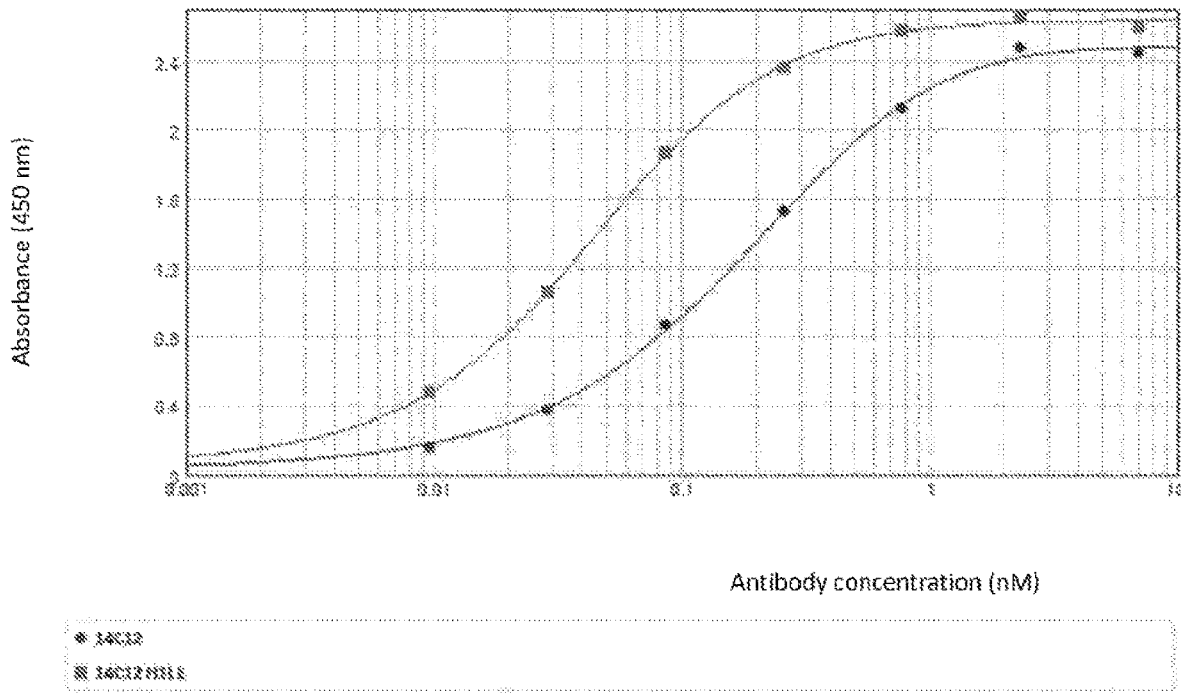
FIG. 30. Indirect ELISA results of 14C12 and 14C12H1L1 binding to PD-1.

The binding results of antibodies 14C12 and 14C12H1L1 to PD-1 were shown in FIG. 30. Evidently, both 14C12 and 14C12H1L1 can bind to PD-1 protein effectively with dose-dependency. The absorbance at different doses were shown in Table 5. Through Curve Simulation using quantitative analyses of absorbance values, EC50 of 14C12 and 14C12H1L1 binding to PD-1 were then determined to be 0.175 nM and 0.043 nM, respectively.

TABLE 5

The binding activities of antibodies 14C12 and 14C12H1L1 to PD-1, respectively
Coating Antigen: PD-1-mFc (0.5 μg/mL)

| Antibody concentration (μg/mL) | 14C12 | | 14C12H1L1 | |
|---|---|---|---|---|
| 1 | 2.463 | 2.439 | 2.643 | 2.557 |
| 0.3 | 2.572 | 2.380 | 2.734 | 2.586 |
| 0.1 | 2.118 | 2.126 | 2.633 | 2.535 |
| 0.03 | 1.607 | 1.438 | 2.384 | 2.335 |
| 0.01 | 0.930 | 0.809 | 1.892 | 1.839 |
| 0.003 | 0.407 | 0.346 | 1.115 | 1.011 |
| 0.001 | 0.167 | 0.150 | 0.503 | 0.455 |
| 0 | 0.062 | 0.047 | 0.068 | 0.064 |
| Secondary antibody | Goat anti-Mouse secondary antibody, HRP Conjugate | | | |

2.2. The binding activity of monoclonal antibody 14C12 produced by hybridoma and its humanized antibody 14C12H1L1 to antigen PD-1 by competition ELISA against PDL1 was measured as follows:

After incubated with PD-1-hFc or PD-1-mFc at 4° C. overnight, the microplate was blocked with 1% BSA at 37° C. for 2 h; and then mixtures of individual antibody, 14C12 or 14C12H1L1, at different concentrations (see Table 6 for dilution gradient) and PDL1-hFc or PDL-1-mFc were added into the microplate to react for 10 mins; and then HRP-labeled secondary antibody was added and incubated at 37° C. for 30 min. The absorbance was read at the wavelength of 450 nm in a microplate reader (see Table 6).

Figure 31:
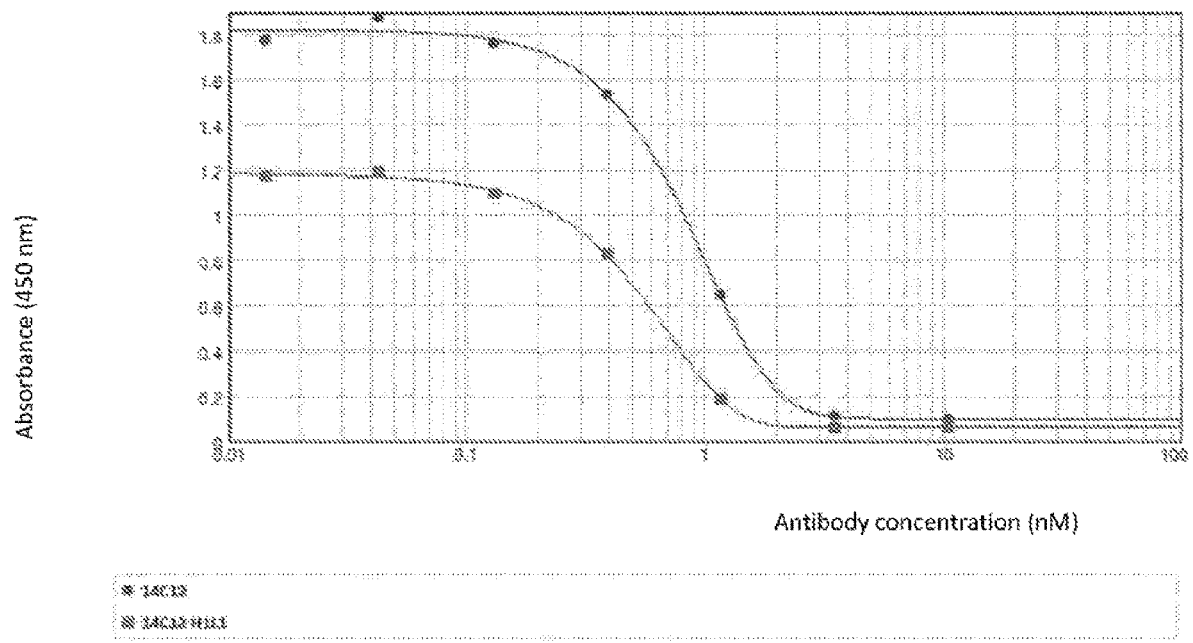
FIG. 31. Competition ELISA results of 14C12 and 14C12H1L1 binding to PD-1 against PDL1.

The binding results of antibodies to PD-1 competing against PDL1 were shown in FIG. 31. the antibody 14C12 and its humanized antibody 14C12H1L1 can compete against PDL1 to bind to PD-1 protein effectively with dose-dependency. The absorbance intensities at different doses were shown in Table 6. By using quantitative analyses of absorbance values, EC50 of 14C12 and 14C12H1L1 binding with PD-1 that were calculated via Curve Simulation were then determined to be 0.853 nM and 0.37 nM, respectively.

TABLE 6

The binding activity of 14C12 and 14C12H1L1 to PD-1 by competition ELISA against PDL1

| Antibody concentration (μg/mL) | Coating antigen: PD-1-mFc 0.2 μg/mL | | | |
|---|---|---|---|---|
| | 14C12 | | 14C12H1L1 | |
| 1.5 μg/ml | 0.111 | 0.088 | 0.135 | 0.113 |
| 1:3 | 0.100 | 0.116 | 0.130 | 0.131 |
| 1:9 | 0.645 | 0.643 | 0.260 | 0.185 |
| 1:27 | 1.463 | 1.614 | 0.257 | 0.218 |
| 1:81 | 1.841 | 1.686 | 0.355 | 0.350 |
| 1:243 | 1.983 | 1.769 | 0.399 | 0.364 |
| 1:729 | 1.789 | 1.770 | 0.417 | 0.411 |
| 0 | 1.791 | 1.790 | 0.430 | 0.402 |
| PDL1-hFc 2 μg/ml | | | | |
| Secondary antibody | Goat anti-Mouse secondary antibody HRP Conjugate | | | |

3. The binding activity of antibodies BiAb001, BiAb002, BiAb003 and BiAb004 to antigens measured by ELISA 3.1 The binding activity of antibodies BiAb001, BiAb002, BiAb003, and BiAb004 to antigen CTLA-4 was determined by indirect ELISA (Refer to methods described in 1.1 of the present Example)

Figure 32:
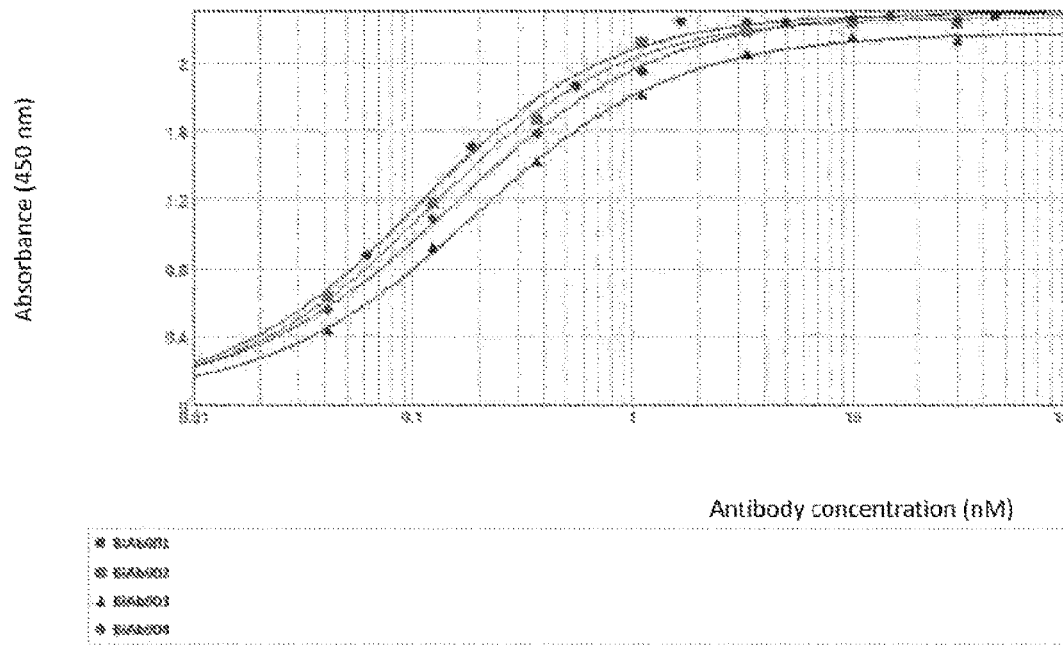
FIG. 32. Indirect ELISA results of BiAb001, BiAb002, BiAb003, and BiAb004 binding to CTLA4.

The binding results of antibodies BiAb001, BiAb002, BiAb003 and BiAb004 to antigen CTLA4 were shown in FIG. 32. Evidently, antibodies BiAb001, BiAb002, BiAb003 and BiAb004 can bind to CTLA4 protein effectively with dose-dependency. The absorbance at different doses were shown in Table 7. Through Curve Simulation using quantitative analyses of absorbance values, EC50 of antibodies BiAb001, BiAb002, BiAb003 and BiAb004 binding to CTLA4 were then determined as shown in Table 7 below.

TABLE 7

The binding activity of bispecific antibodies BiAb001, BiAb002, BiAb003, and BiAb004 to antigen CTLA4 (Indirect ELISA)

| Serial dilution of Antibody | Coating Antigen: CTLA4 0.5 μg/ml | | | | | | | |
|---|---|---|---|---|---|---|---|---|
| | BiAb001 | | BiAb002 | | BiAb003 | | BiAb004 | |
| 6 μg/ml | 2.425 | 2.098 | 2.334 | 2.120 | 2.179 | 2.076 | 2.243 | 2.251 |
| 1:3 | 2.299 | 2.234 | 2.204 | 2.257 | 2.141 | 2.138 | 2.198 | 2.319 |
| 1:9 | 2.265 | 2.188 | 2.168 | 2.186 | 2.012 | 2.086 | 2.207 | 2.254 |
| 1:27 | 2.245 | 2.215 | 2.174 | 2.043 | 1.814 | 1.811 | 1.982 | 1.907 |
| 1:81 | 1.859 | 1.856 | 1.717 | 1.609 | 1.438 | 1.410 | 1.534 | 1.640 |
| 1:243 | 1.494 | 1.511 | 1.221 | 1.136 | 0.933 | 0.899 | 1.070 | 1.108 |
| 1:729 | 0.818 | 0.922 | 0.644 | 0.610 | 0.451 | 0.414 | 0.567 | 0.548 |
| 0 | 0.048 | 0.048 | 0.048 | 0.047 | 0.047 | 0.045 | 0.049 | 0.050 |

TABLE 7-continued

The binding activity of bispecific antibodies BiAb001, BiAb002, BiAb003, and BiAb004 to antigen CTLA4 (Indirect ELISA)

| Serial dilution of Antibody | Coating Antigen: CTLA4 0.5 µg/ml | | | |
|---|---|---|---|---|
| | BiAb001 | BiAb002 | BiAb003 | BiAb004 |
| Secondary antibody: Goat anti-human IgG, HRP (1:5000) | | | | |
| EC50 (nM) | 0.105 | 0.12 | 0.189 | 0.154 |

3.2 The binding activity of antibodies BiAb001, BiAb002, BiAb003, and BiAb004 to antigen PD-1 was determined by indirect ELISA. (Refer to methods described in 2.1 of the present Example)

Figure 33:
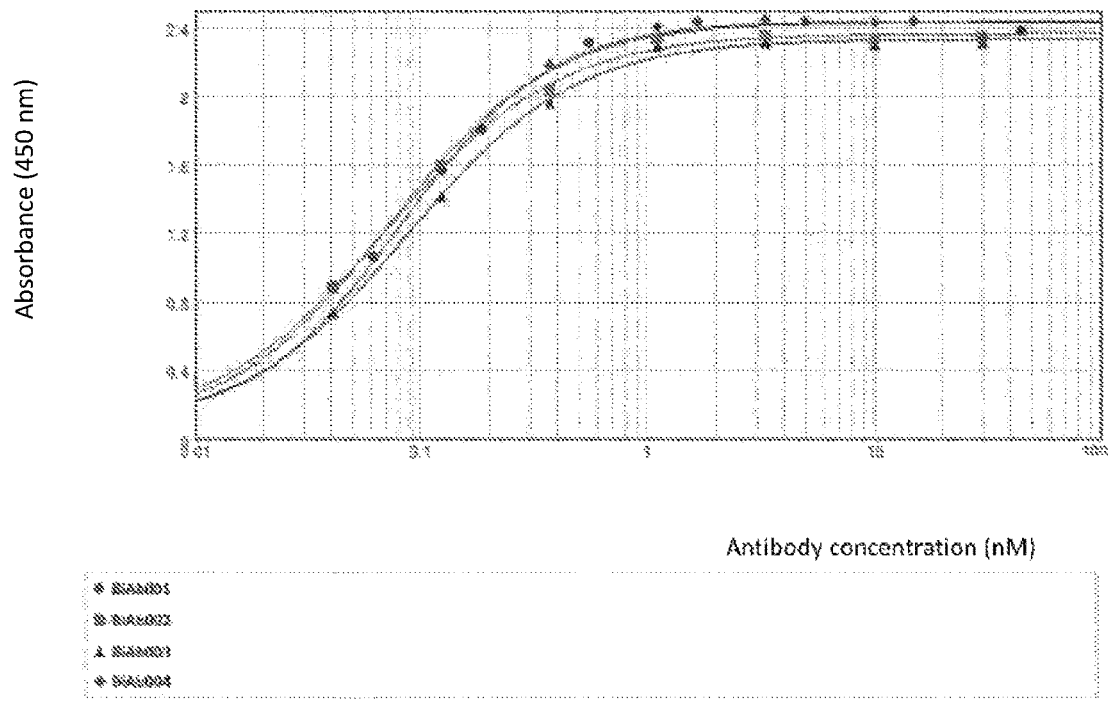
FIG. 33. Indirect ELISA results of BiAb001, BiAb002, BiAb003, and BiAb004 binding to PD-1.

The binding results of antibodies BiAb001, BiAb002, BiAb003, and BiAb004 to antigen PD-1 were shown in FIG. 33. Evidently, antibodies BiAb001, BiAb002, BiAb003, and BiAb004 can bind to PD-1 protein effectively with dose-dependency. The absorbance intensities at different doses were shown in Table 7. Through Curve Simulation using quantitative analyses of absorbance values, EC50 of antibodies BiAb001, BiAb002, BiAb003 and BiAb004 binding to PD-1 were then determined as shown in Table 8 below.

TABLE 8

The binding activity of bispecific antibodies to antigen CTLA4 (Indirect ELISA)

| Serial dilution of Antibody | Coating Antigen: PD-1-mFc 0.5 µg/ml | | | | | | | |
|---|---|---|---|---|---|---|---|---|
| | BiAb001 | | BiAb002 | | BiAb003 | | BiAb004 | |
| 6 µg/ml | 2.400 | 2.360 | 2.370 | 2.314 | 2.332 | 2.290 | 2.347 | 2.343 |
| 1:3 | 2.450 | 2.426 | 2.290 | 2.388 | 2.271 | 2.326 | 2.410 | 2.458 |
| 1:9 | 2.402 | 2.457 | 2.372 | 2.346 | 2.279 | 2.351 | 2.390 | 2.505 |
| 1:27 | 2.409 | 2.467 | 2.332 | 2.348 | 2.350 | 2.243 | 2.414 | 2.396 |
| 1:81 | 2.375 | 2.254 | 2.084 | 1.990 | 1.996 | 1.928 | 2.197 | 2.175 |
| 1:243 | 1.871 | 1.725 | 1.627 | 1.544 | 1.414 | 1.419 | 1.573 | 1.560 |
| 1:729 | 1.067 | 1.047 | 0.954 | 0.814 | 0.746 | 0.719 | 0.920 | 0.865 |
| 0 | 0.085 | 0.067 | 0.065 | 0.068 | 0.055 | 0.055 | 0.056 | 0.058 |
| Secondary antibody: Goat anti-human IgG, HRP (1:5000) | | | | | | | | |

3.3 The binding activity of the antibodies BiAb001, BiAb002, BiAb003, and BiAb004 to CTLA4 respectively by competition ELISA against B7/1-hFc (Refer to methods described in 1.2 of the present Example).

Figure 34:
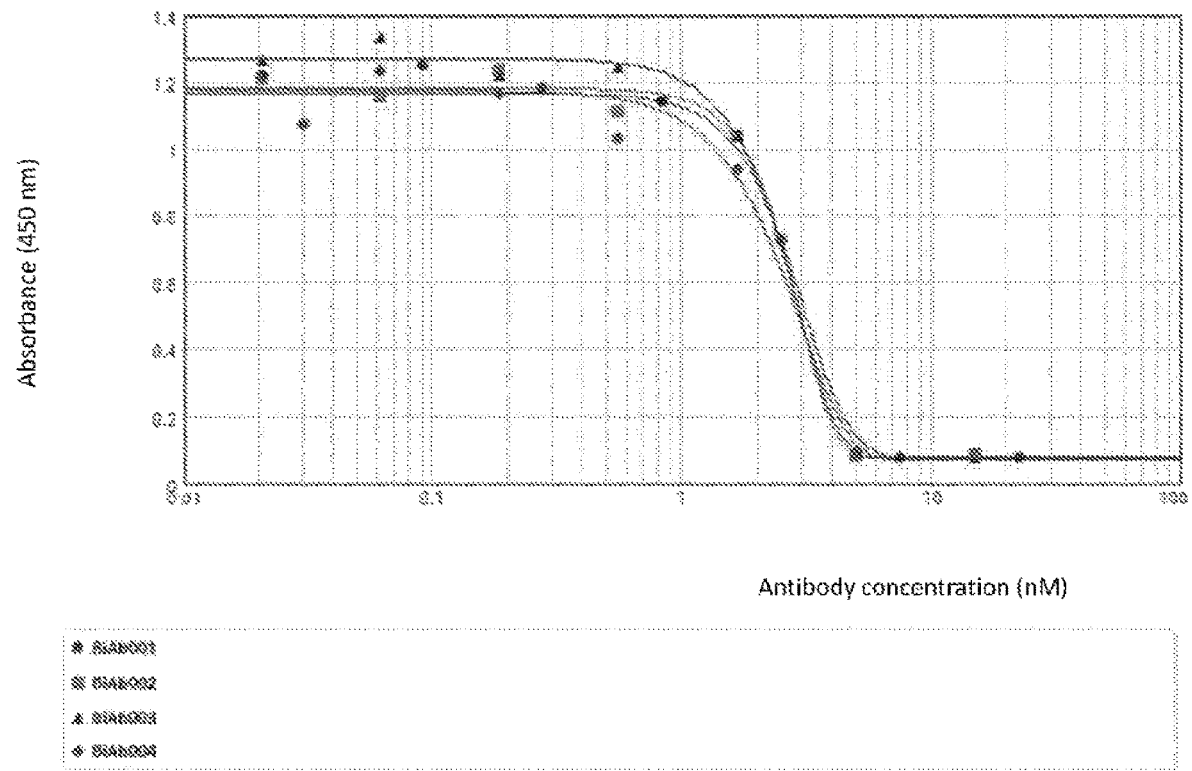
FIG. 34. Competition ELISA results of BiAb001, BiAb002, BiAb003, and BiAb004 binding to CTLA4 against B7.

The binding results were shown in FIG. 34. As shown in the figure, the antibodies BiAb001, BiAb002, BiAb003, and BiAb004 can effectively bind antigen CTLA4 and inhibit CTLA4 binding to B7/1 with dose-dependency. The absorbance intensities at different doses were shown in Table 9. Through Curve Simulation using quantitative analyses of absorbance values, EC50 of antibodies BiAb001, BiAb002, BiAb003 and BiAb004 were then determined as shown in Table 9 below.

TABLE 9

The binding activity of antibodies to CTLA4 by competition ELISA against B7/1-hFc

| Serial dilution of Antibody | Coating Antigen: B7/1-hFc 0.5 µg/ml | | | | | | | |
|---|---|---|---|---|---|---|---|---|
| | BiAb001 | | BiAb002 | | BiAb003 | | BiAb004 | |
| 3 µg/ml | 0.076 | 0.072 | 0.078 | 0.095 | 0.074 | 0.080 | 0.095 | 0.076 |
| 1:3 | 0.081 | 0.076 | 0.079 | 0.079 | 0.095 | 0.086 | 0.097 | 0.100 |
| 1:9 | 0.748 | 0.706 | 1.040 | 1.031 | 1.029 | 1.049 | 0.907 | 0.973 |
| 1:27 | 1.153 | 1.129 | 1.076 | 1.152 | 1.125 | 1.361 | 1.010 | 1.056 |
| 1:81 | 1.121 | 1.241 | 1.153 | 1.315 | 1.241 | 1.198 | 1.121 | 1.206 |
| 1:243 | 1.261 | 1.236 | 1.047 | 1.266 | 1.333 | 1.335 | 1.231 | 1.235 |
| 1:729 | 1.063 | 1.077 | 1.085 | 1.337 | 1.210 | 1.323 | 1.157 | 1.287 |
| 0 | 1.0476 | 0.9808 | 0.9131 | 1.0762 | 1.067 | 1.074 | 1.032 | 0.966 |
| Receptor: CTLA4-mFc 0.3 µg/ml | | | | | | | | |
| Secondary antibody: Goat anti-Mouse IgG, HRP Conjugate (1:5000) | | | | | | | | |
| EC50 (nM) | 2.758 | | 1.797 | | 2.197 | | 2.256 | |

3.4 The binding activity of antibodies BiAb001, BiAb002, BiAb003, and BiAb004 to antigen PD-1 by competition ELISA against PDL1 (Refer to methods described in 2.2 of the present Example)

Figure 35:
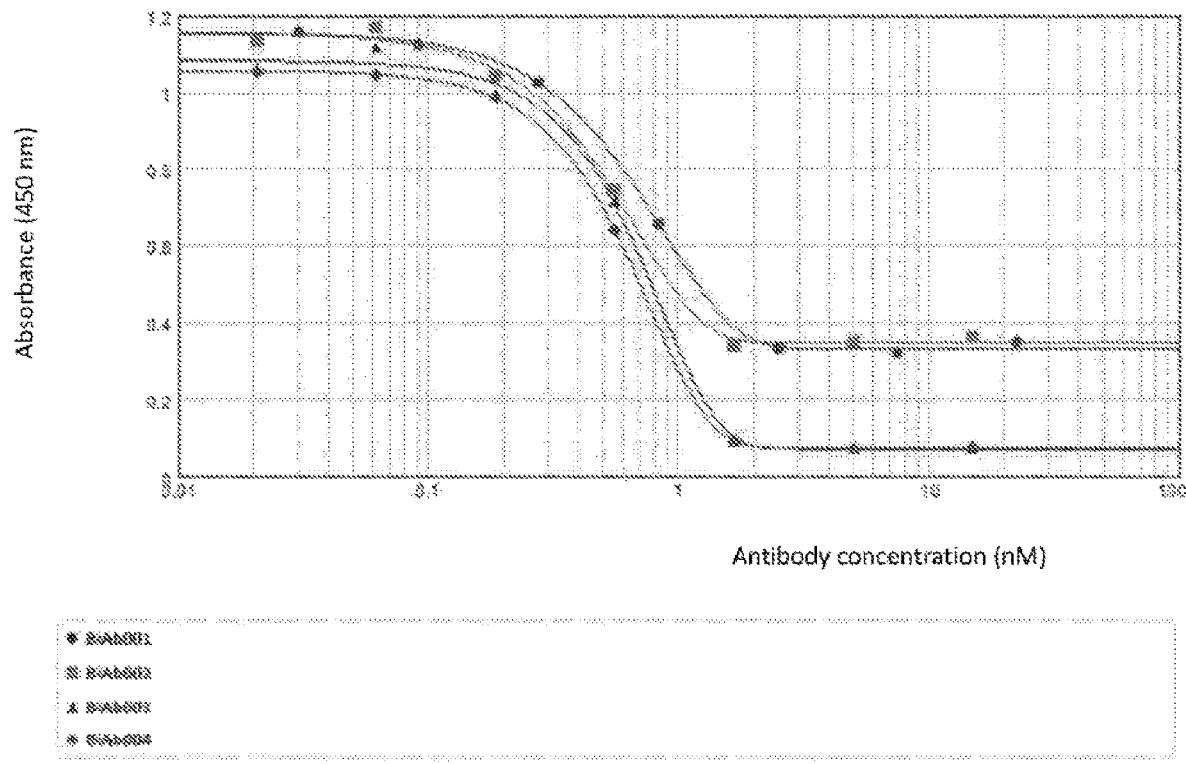
FIG. 35. Competition ELISA results of BiAb001, BiAb002, BiAb003, and BiAb004 binding to PD-1 against PDL1.

The binding results were shown in FIG. 35. Evidently, the antibodies BiAb001, BiAb002, BiAb003, and BiAb004 can effectively bind antigen PD-1 and inhibit PD-1 binding to PDL1 with dose-dependency. The absorbance intensities at different doses were shown in Table 10. Through Curve Simulation using quantitative analyses of absorbance values, EC50 of antibodies BiAb001, BiAb002, BiAb003 and BiAb004 to CTLA4 were then determined as shown in Table 10 below.

TABLE 10

The binding activity of antibodies to PD-1 by competition ELISA against PDL1.

| Antibody concentration | Coating antigen: PD-1-hFc 0.5 μg/ml | | | | | | | |
|---|---|---|---|---|---|---|---|---|
| | BiAb001 | | BiAb002 | | BiAb003 | | BiAb004 | |
| 3 μg/ml | 0.347 | 0.348 | 0.369 | 0.353 | 0.074 | 0.075 | 0.078 | 0.075 |
| 1:3 | 0.314 | 0.326 | 0.348 | 0.350 | 0.071 | 0.081 | 0.073 | 0.074 |
| 1:9 | 0.332 | 0.330 | 0.340 | 0.340 | 0.095 | 0.095 | 0.093 | 0.095 |
| 1:27 | 0.542 | 0.775 | 0.758 | 0.733 | 0.695 | 0.737 | 0.639 | 0.643 |
| 1:81 | 1.041 | 1.009 | 1.018 | 1.063 | 0.983 | 1.010 | 0.954 | 1.019 |
| 1:243 | 1.131 | 1.117 | 1.149 | 1.186 | 1.070 | 1.165 | 1.009 | 1.082 |
| 1:729 | 1.186 | 1.129 | 1.072 | 1.199 | 1.093 | 1.029 | 1.032 | 1.080 |
| 0 | 1.2345 | 1.1091 | 1.1243 | 1.1759 | 1.101 | 1.140 | 1.178 | 1.153 |
| Receptor: PDL1-mFc 0.3 μg/ml | | | | | | | | |
| Secondary antibody: Goat anti-human IgG, HRP (1:5000) | | | | | | | | |
| $EC_{50}$ (nM) | 0.685 | | 0.543 | | 0.665 | | 0.62 | |

Example 10: The Binding Activity of Antibodies to Cell Surface Antigen by Flow Cytometry Method Host cells 293T expressing CTLA4 or PD-1 antigens were constructed respectively, and labeled with the humanized antibodies prepared in the present invention. The ability of the antibodies to bind specifically to corresponding cell surface antigens in its native conformation was analyzed and validated by flow cytometry.

1. Construction of 293T Host Cell Expressing CTLA4 or PD-1

293T cells were transfected with the CTLA4 containing plasmid pLenti6.3-CTLA4 or PD-1-containing plasmid pLenti6.3-PD-1 (vector pLenti6.3 was purchased from Invitrogen Corporation) and screened to obtain the stable pools of 293T-CTLA4 or 293T-PD-1 expressing CTLA4 or PD-1, respectively.

2. Antibody Binding to Cell Surface Antigens

The host cells obtained above that express individual antigen were digested by using trypsin, and distributed into tubes each containing $2\times10^5$ cells. Antibodies were diluted in gradient using PBSA buffer (1% BSA) and incubated with 293T cells that express corresponding antigens on ice for 2 h. 100 μL of FITC-labeled goat anti-human IgG (1:500) was added into each tube and incubated on ice for 1 h. After being washed with PBS for 3 times, cells were re-suspended in 300 μL of PBS, and fluorescence signals were measured on the flow cytometer using the FITC channel.

2.1 Binding Activity of Antibodies to Cell Surface Antigens

Figure 36:
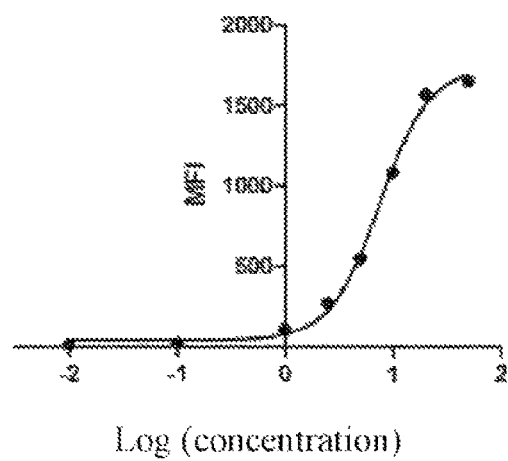
FIG. 36. EC50 of 4G10H1L1 binding to CTLA4 on the Surface of 293T-CTLA4 Cells.
Figure 37:
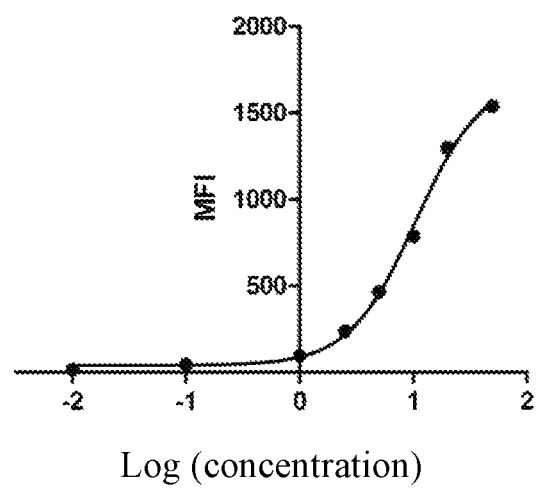
FIG. 37. EC50 of 4G10H3L3 binding to CTLA4 on the Surface of 293T-CTLA4 Cells.

The binding results of humanized antibodies 4G10H1L1 and 4G10H3L3 to 293T-CTLA4 cells were shown in FIG. 36 and FIG. 37. As shown in the figure, the antibodies 4G10H1L1 and 4G10H3L3 can effectively bind to target protein CTLA4 expressed on the surface of host cells 293T-CTLA4 with dose-dependency. The fluorescence intensities at different doses were shown in Table 11. Through Curve Simulation using quantitative analyses of absorbance values, $EC_{50}$ of 4G10H1L1 and 4G10H3L3 binding to CTLA4 were determined to be 7.58 nM and 10.54 nM, respectively.

TABLE 11

The fluorescence intensities of antibodies 4G10H1L1 and 4G10H3L3 binding to CTLA4 expressed on 293T-CTLA4 cell surface by Flow Cytometry

| Antibody concentration (nM) | 4G10H1L1 | 4G10H2L2 |
|---|---|---|
| | fluorescence intensity | |
| 0.01 | 14.93 | 15.13 |
| 0.1 | 24.79 | 47.05 |
| 1 | 106.77 | 97.27 |
| 2.5 | 272.24 | 236.66 |
| 5 | 547.76 | 465.54 |
| 10 | 1080.91 | 788 |
| 20 | 1568.19 | 1296.95 |
| 50 | 1652.26 | 1539.24 |

Figure 38:
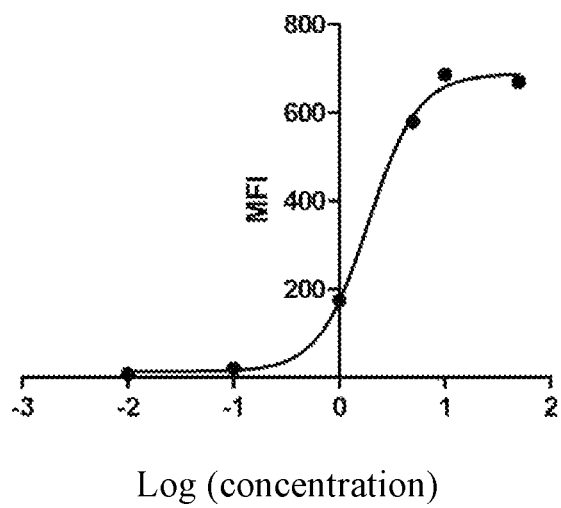
FIG. 38. EC50 of 14C12H1L1 binding to PD-1 on the Surface of 293T-PD-1 Cells.
Figure 39:
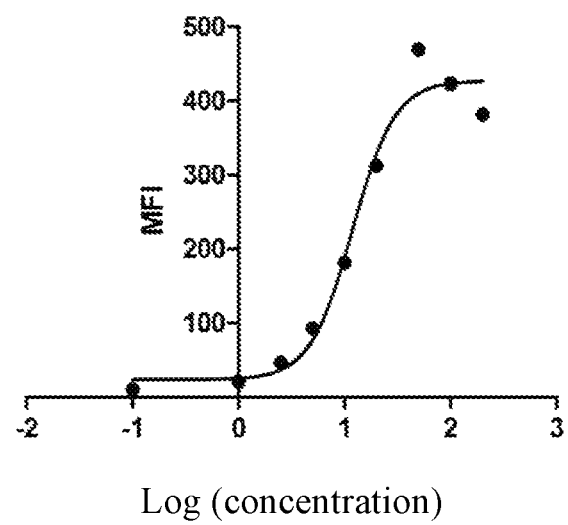
FIG. 39. EC50 of BiAb001 binding to CTLA4 on the Surface of 293T-CTLA4 Cells.
Figure 40:
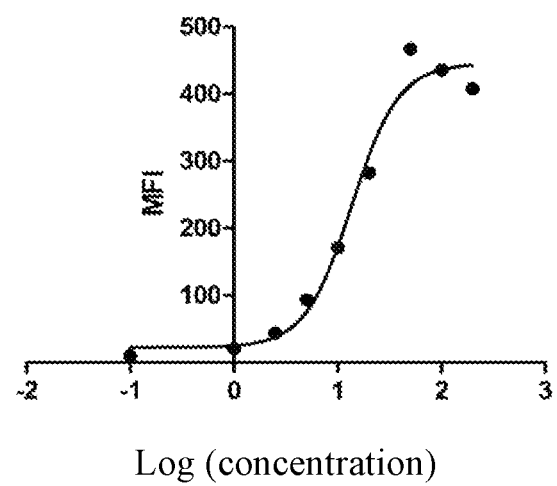
FIG. 40. EC50 of BiAb002 binding to CTLA4 on the Surface of 293T-CTLA4 Cells.
Figure 41:
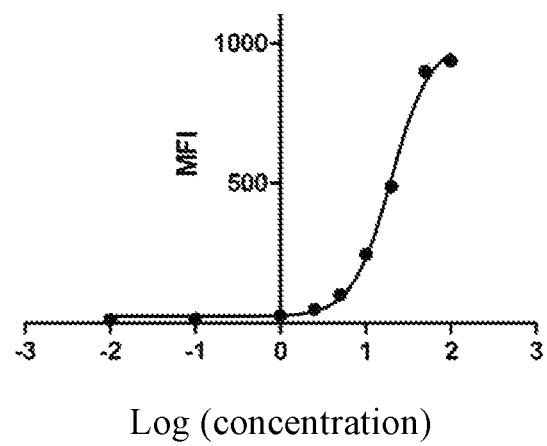
FIG. 41. EC50 of BiAb003 binding to CTLA4 on the Surface of 293T-CTLA4 Cells.
Figure 42:
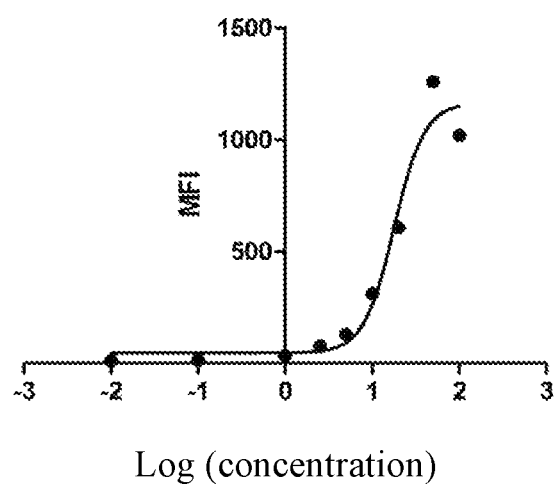
FIG. 42. EC50 of BiAb004 binding to CTLA4 on the Surface of 293T-CTLA4 Cells.
Figure 43:
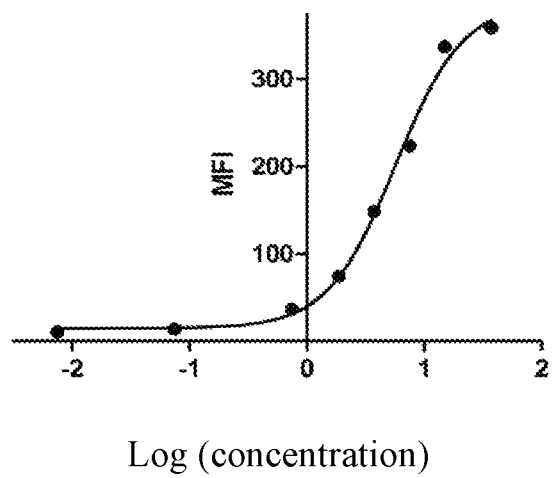
FIG. 43. EC50 of BiAb001 binding to PD-1 on the Surface of 293T-PD-1 Cells.
Figure 44:
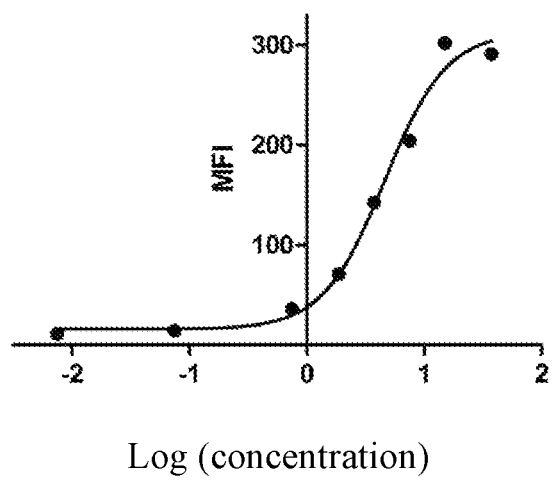
FIG. 44. EC50 of BiAb002 binding to PD-1 on the Surface of 293T-PD-1 Cells.
Figure 45:
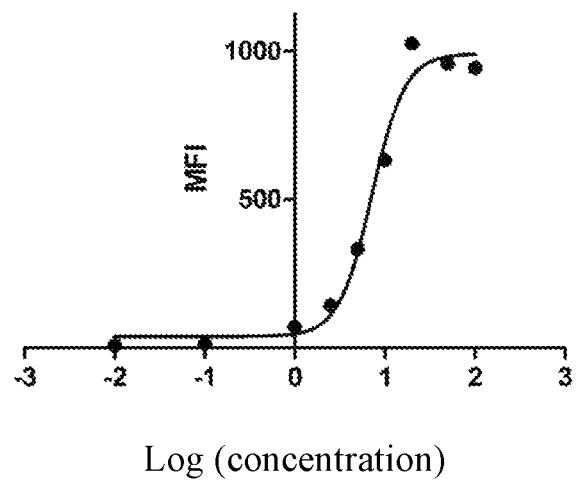
FIG. 45. EC50 of BiAb003 binding to PD-1 on the Surface of 293T-PD-1 Cells.
Figure 46:
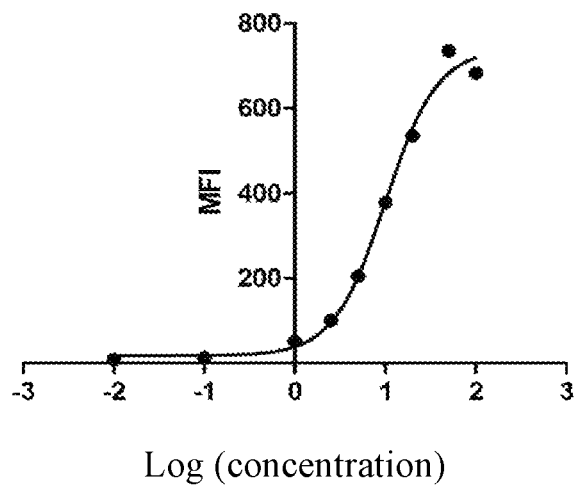
FIG. 46. EC50 of BiAb004 binding to PD-1 on the Surface of 293T-PD-1 Cells.

2.2 The binding results of humanized antibody 14C12H1L1 to 293T-PD-1 cells were shown in FIG. 38. As shown in the figure, the antibody 14C12H1L1 can effectively bind to target protein PD-1 expressed on the surface of host cells 293T-PD-1 with dose-dependency. The fluorescence intensities at different doses were shown in Table 12. Through Curve Simulation using quantitative analyses of fluorescence intensity, $EC_{50}$ of 14C12H1L1 binding to PD-1 was determined to be 1.89 nM.

TABLE 12

The fluorescence intensity of antibody 14C12H1L1 binding to PD-1 expressed on 293T-PD-1 cell surface by Flow Cytometry.

| | Antibody concentration (nM) | | | | | |
|---|---|---|---|---|---|---|
| | 0.01 | 0.1 | 1 | 5 | 10 | 50 |
| fluorescence intensity | 8.32 | 20.31 | 174.62 | 579.41 | 686.49 | 669.54 |

2.3 The binding results of the antibodies BiAb001, BiAb002, BiAb003, and BiAb004 to 293T-CTLA4 cells were shown in FIGS. 39-42. As shown in the figures, the antibodies BiAb001, BiAb002, BiAb003, and BiAb004 can effectively bind to target protein CTLA4 expressed on the surface of host cell 293T-CTLA4 with dose-dependency. The fluorescence intensities at different doses were shown in Table 13. Through Curve Simulation using quantitative analyses of fluorescence intensities, $EC_{50}$ of BiAb001, BiAb002, BiAb003, and BiAb004 were determined as shown in Table 13 below.

TABLE 13

The fluorescence intensities and $EC_{50}$ of the antibodies BiAb001, BiAb002, BiAb003, and BiAb004 binding to CTLA4 expressed on 293T-CTLA4 cell surface by Flow Cytometry

| Antibody concentration (nM) | BIAb001 | BIAb002 | BIAb003 | BIAb004 |
|---|---|---|---|---|
| | MFI (fluorescence intensity) | | | |
| 0.0 | — | — | 12.9 | 13.0 |
| 0.1 | 10.5 | 10.5 | 14.2 | 15.6 |
| 1.0 | 21.2 | 20.4 | 28.7 | 34.8 |
| 2.5 | 46.8 | 43.8 | 49.6 | 77.4 |
| 5.0 | 92.9 | 93.5 | 101.0 | 129.6 |
| 10.0 | 181.9 | 171.2 | 245.3 | 313.0 |
| 20.0 | 312.8 | 282.1 | 487.4 | 608.6 |
| 50.0 | 469.5 | 466.5 | 899.8 | 1260.8 |
| 100.0 | 423.0 | 435.3 | 937.5 | 1020.6 |
| 200.0 | 381.6 | 408.2 | — | — |
| EC50 (nM) | 11.9 | 13.7 | 19.9 | 17.8 |

2.4 The binding results of the antibodies BiAb001, BiAb002, BiAb003, and BiAb004 to 293T-PD-1 cells are shown in FIGS. 43-46. Evidently, the antibodies BiAb001, BiAb002, BiAb003, and BiAb004 can effectively bind to PD-1 expressed on the surface of host cell 293T-PD-1 with dose-dependency. The fluorescence intensities at different doses were shown in Table 14. Through Curve Simulation using quantitative analyses of absorbance values, $EC_{50}$ of BiAb001, BiAb002, BiAb003, and BiAb004 were determined as shown in Table 14 below.

TABLE 14

The fluorescence intensities of the antibodies BiAb001, BiAb002, BiAb003, and BiAb004 binding to PD-1 expressed on 293T-PD-1 cell surface by Flow Cytometry

| Antibody concentration/nM | BIAb001 | BIAb002 | Antibody concentration/nM | BIAb003 | BIAb004 |
|---|---|---|---|---|---|
| | MFI (fluorescence intensity) | | | MFI (fluorescence intensity) | |
| 0.01 | 10.18 | 11 | 0.01 | 8.56 | 8.89 |
| 0.08 | 13.92 | 14.09 | 0.1 | 14.57 | 13.46 |
| 0.75 | 36.44 | 36.11 | 1 | 70.76 | 50.8 |
| 1.88 | 74.27 | 70.97 | 2.5 | 143.24 | 100.83 |
| 3.75 | 148.28 | 142.37 | 5 | 332.5 | 204.83 |
| 7.5 | 223.29 | 204.22 | 10 | 632.57 | 378.31 |
| 15 | 337.03 | 302.05 | 20 | 1026.03 | 535.69 |
| 37.5 | 358.78 | 290.92 | 50 | 958.92 | 734.73 |
| | | | 100 | 943.77 | 682.25 |
| EC50 (nM) | 5.69 | 4.61 | | 7.18 | 10 |

3. The binding activity of antibodies to T cell surface antigens CTLA4 and PD-1 PBMC was isolated by Ficoll-Paque Plus (GE Healthcare LOT No.:171440-02), and further isolated to get CD4+ cells, and then cells were stimulated with PHA for three days and then cells were washed once with PBS and mixed with antibodies at different concentrations, and then incubated on ice for 1.5 h. The cells were then washed with PBS once after incubation, and the FITC-labeled anti-human IgG (Jackson immunoresearch lot. 102155). Then the cells were incubated on ice in the dark for 1 h, washed with PBS for once, and then the fluorescence signals were measured on the flow cytometer.

The control anti-PD-1 antibody Nivolumab is commercially available, and its information could also be found in http://www.drugbank.ca/drugs/DB09035;

The control anti-CTLA4 antibody Ipilimumab is commercially available, and its information can be found in http://www.drugbank.ca/drugs/DB06186.

Figure 47:
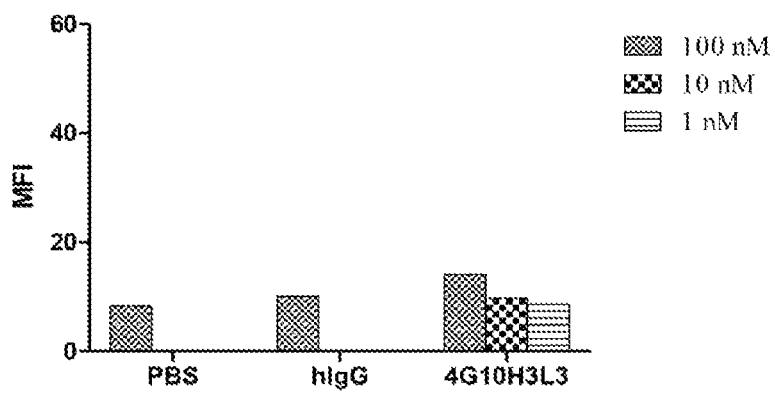
FIG. 47. Binding activity of 4G10H3L3 to T Cell Surface Antigen CTLA4.

3.1 The binding results of humanized antibody 4G10H3L3 to T cells were shown in FIG. 47. As shown in figure, the antibody 4G10H3L3 can effectively bind to the target protein CTLA4 expressed on the surface of T cells with dose-dependency.

Figure 48:
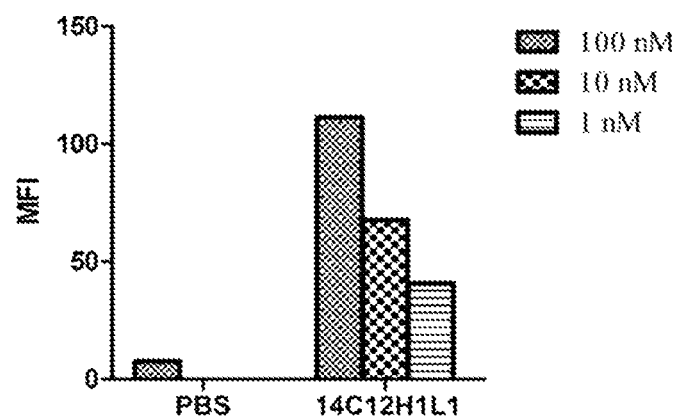
FIG. 48. Binding activity of 14C12H1L1 to T Cell Surface Antigen PD-1.

3.2 The binding results of humanized antibody 14C12H1L1 to T cells were shown in FIG. 48. As shown in figure, the antibody 14C12H1L1 can effectively bind to the target PD-1 expressed on the surface of T cells with dose-dependency.

Figure 49:
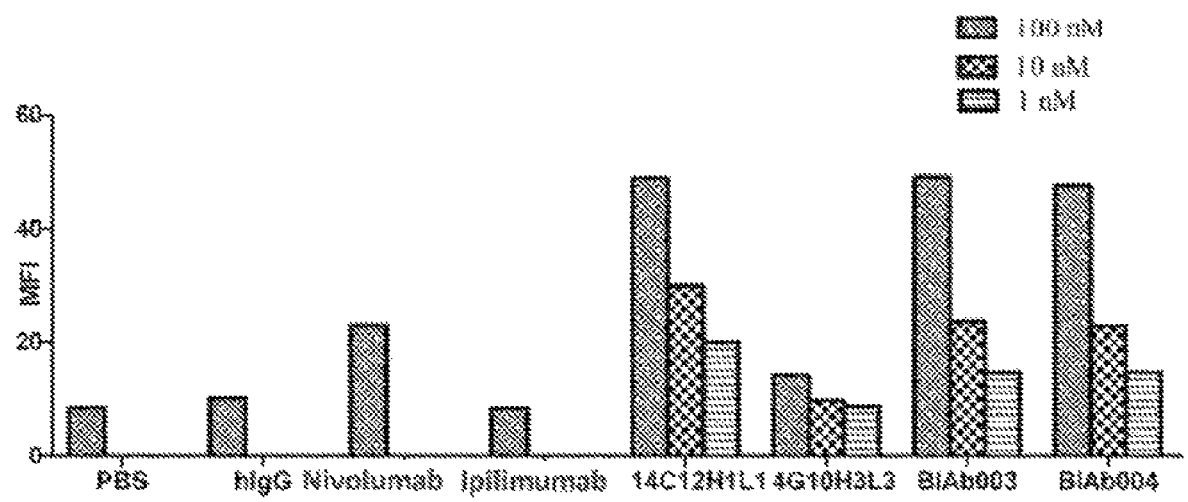
FIG. 49. Binding activity of BiAb003 and BiAb004 to T Cell Surface Antigens compared with those of 14C12H1L1 and 4G10H3L3.
Figure 50:
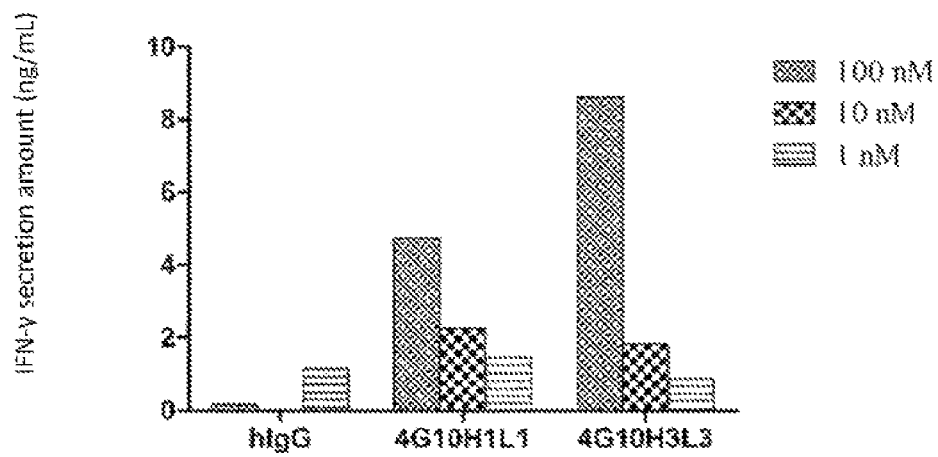
FIG. 50. Effects of 4G10H1L1 and 4G10H3L3 on IFN-γ Secretion of Mixed Lymphocytes.
Figure 51:
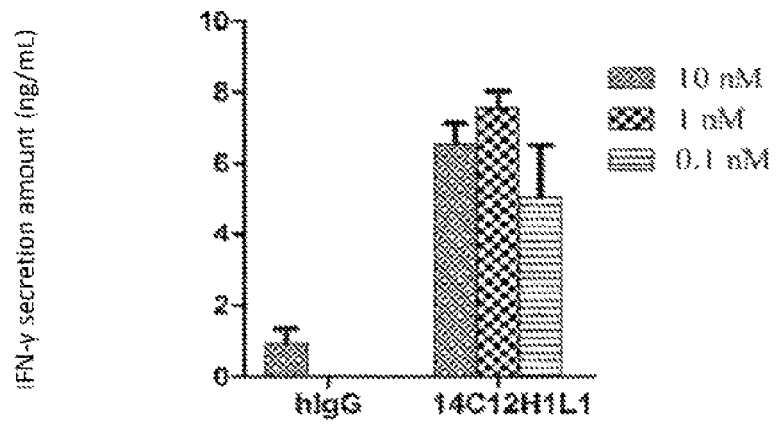
FIG. 51. Effect of 14C12H1L1 on IFN-γ Secretion of Mixed Lymphocytes.

3.3 The binding activity to T cells of the antibodies BiAb003 and BiAb004 compared with that of 14C12H1L1 and 4G10H3L3 were shown in FIG. 49. As shown in figure, the antibodies BiAb003, BiAb004, 14C12H1L1, and 4G10H3L3 can effectively bind to the target protein PD-1 expressed on the surface of T cells with dose-dependency. Furthermore, the binding activity of the antibodies BiAb003, BiAb004, and 14C12H1L1 to T cells were stronger than those of the antibodies 4G10H3L3, Nivolumab, and Ipilimumab. The fluorescence intensity was shown in Table 15.

TABLE 15

The fluorescence intensities of the antibodies 14C12H1L1, 4G10H3L3, BiAb003, and BiAb004 binding to T cells

| Name of antibody | Antibody concentration/nM | | |
|---|---|---|---|
| | 100 | 10 | 1 |
| | MFI (fluorescence intensity) | | |
| PBS | 8.39 | — | — |
| hIgG | 10.15 | — | — |
| Nivolumab | 22.88 | — | — |
| Ipilimumab | 8.35 | — | — |
| 14C12H1L1 | 48.94 | 29.93 | 19.97 |
| 4G10H3L3 | 14.11 | 9.78 | 8.62 |
| BIAb003 | 49.09 | 23.67 | 14.65 |
| BIAb004 | 47.54 | 22.85 | 14.66 |

Example 11: Mixed Lymphocyte Reaction: Secretion of Cytokine IFN-γ and IL-2

PBMC was isolated by Ficoll-Paque Plus (GE Healthcare LOT No.: 171440-02), then mixed with IL-4 (Peprotech K2513, 1000 U/ml) and GM-CSF (Peprotech H1513, 1000 U/ml) to induce for 6 days, and then TNF-α (Peprotech G1513, 200 U/ml) was added to induce for 3 days to obtain DC cells.

T cells were isolated from PBMC and mixed with the DC cells ousedbtained above in the ratio of 1:10 to culture together with each antibody (hIgG was control) in different ratios for 5-6 days. The secretions of IFN-γ or IL-2 were measured with ELISA reagent kits (both purchased from Dakewe), respectively.

Figure 54:
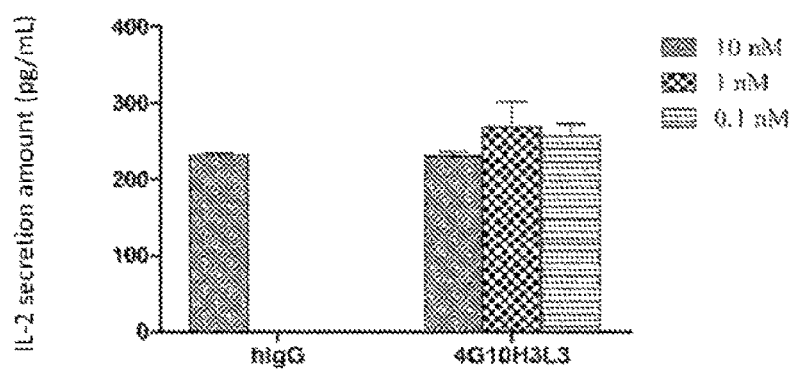
FIG. 54. Effect of 4G10H3L3 on IL-2 Secretion of Mixed Lymphocytes.
Figure 55:
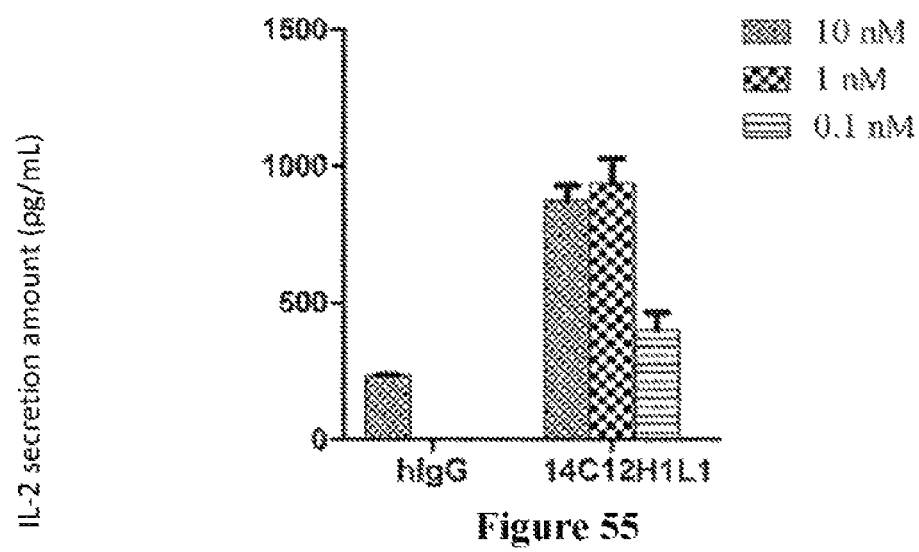
FIG. 55. Effect of 14C12H1L1 on IL-2 Secretion of Mixed Lymphocytes.
Figure 56:
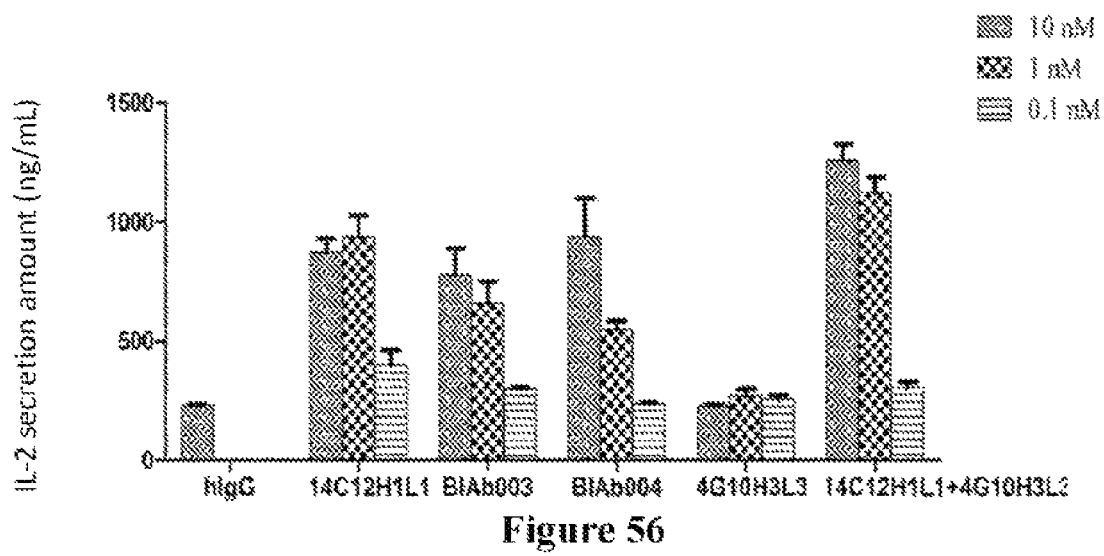
FIG. 56. Effects of BiAb003 and BiAb004 on IL-2 Secretion of Mixed Lymphocytes compared with those of 14C12H1L1 and 4G10H3L3.

The secretions of IFN-γ after mixed culture of DC cells and T cells were shown in FIG. 50-FIG. 53. The secretions of IL-2 after mixed culture of DC cells and T cells were shown in FIGS. 54-56.

Figure 52:
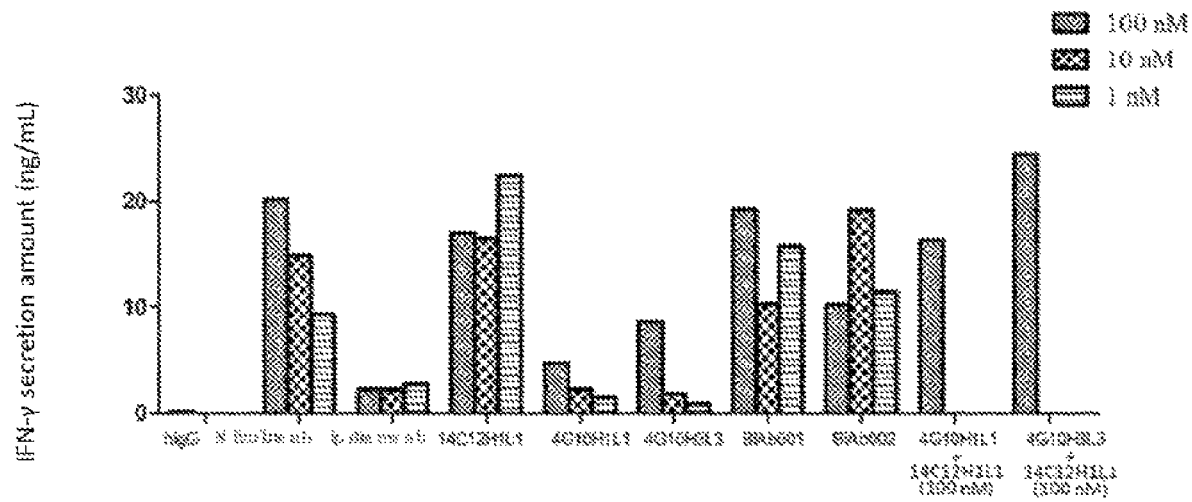
FIG. 52. Effects of BiAb001 and BiAb002 on IFN-γ Secretion of Mixed Lymphocytes compared with those of 14C12H1L1 and 4G10H1L1.
Figure 53:
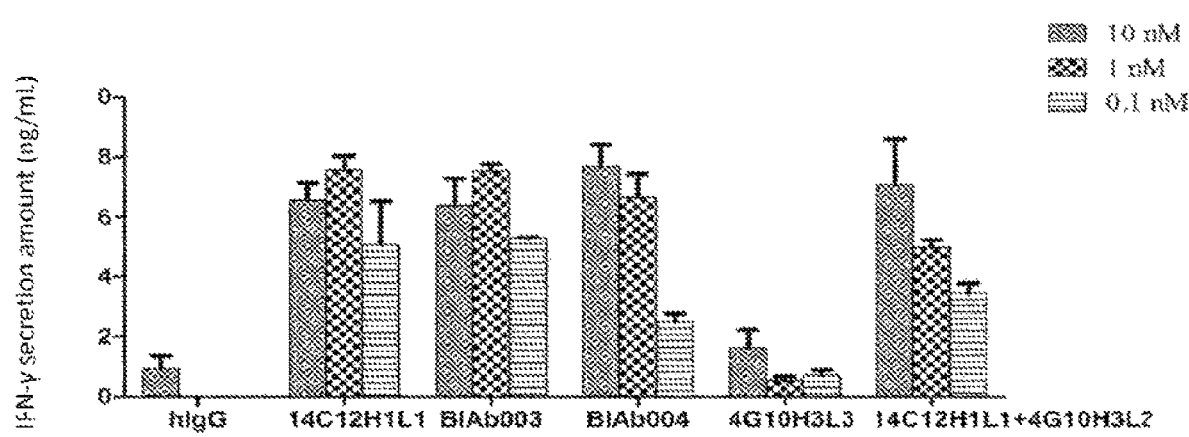
FIG. 53. Effects of BiAb003 and BiAb004 on IFN-γ Secretion of Mixed Lymphocytes compared with effects of 14C12H1L1 and 4G10H3L3.

As shown in figures, the antibodies 4G10H1L1, 4G10H3L3, and 14C12H1L1, as well as bispecific antibodies BiAb001, BiAb002, BiAb003, and BiAb004 all can effectively induce the secretion of IFN-γ and IL-2 in mixed lymphocytes. The IFN-γ secretion induced by 1 nM or 10 nM anti-PD-1 antibody 14C12H1L1 were comparable with that of 100 nM control antibody Nivolumab. The IFN-γ secretion induced by 100 nM anti-CTLA4 antibodies 4G10H1L1 and 4G10H3L3 were better than that of 100 nM control antibody Ipilimumab (FIG. 52).

Example 12: Induced IL-2 Secretion

The isolated PBMCs (the same method as in Example) was stimulated with PHA (Shanghai Shenqi Biotech Co., Ltd, 50 μl/ml) for 3 days, and then PBMCs (from volunteer blood donors, $5 \times 10^4$ cells/well) mixed with Raji cells (from ATCC, $5 \times 10^4$ cells/well) and MDA-MB-231 cells (from ATCC, $1 \times 10^4$ cells/well) in a 96-well plate. Antibodies (100 nM) were added and mixed and cultured together. After co-culture for 3 days, secretion of IL-2 was measured with ELISA reagent kit (purchased from Dakewe) according to the instructions.

Figure 57:
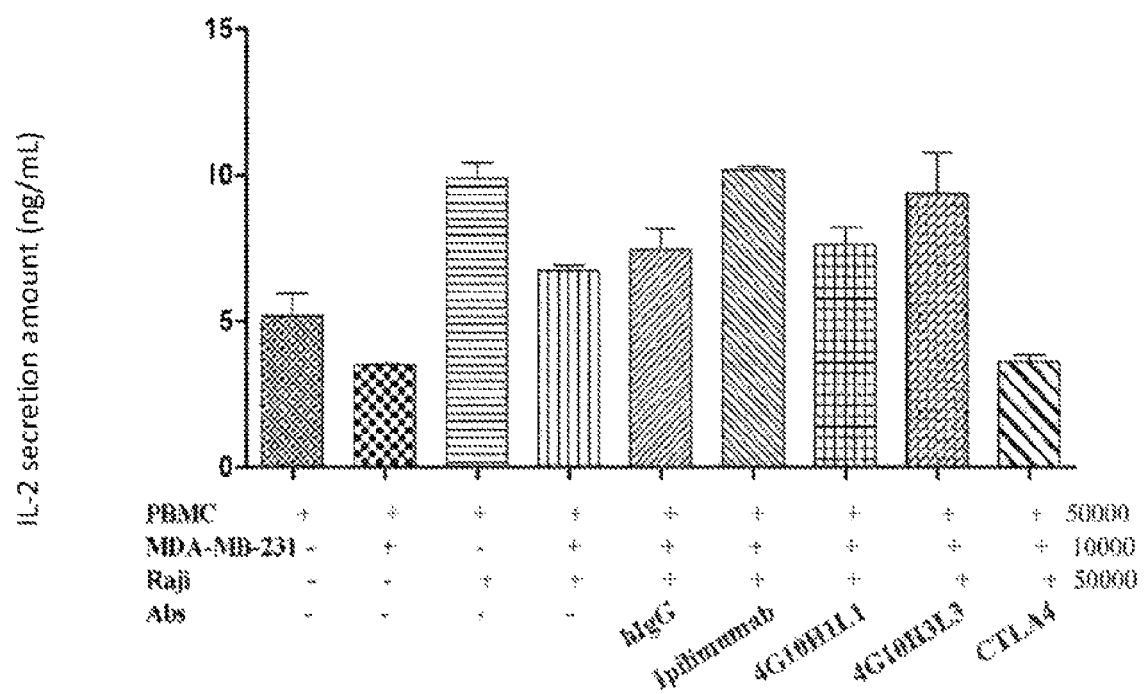
FIG. 57. Effects of 4G10H1L1 and 4G10H3L3 on IL-2 Secretion induced by co-culturing of PBMC, MDA-MB-231 and Raji cells.
Figure 58:
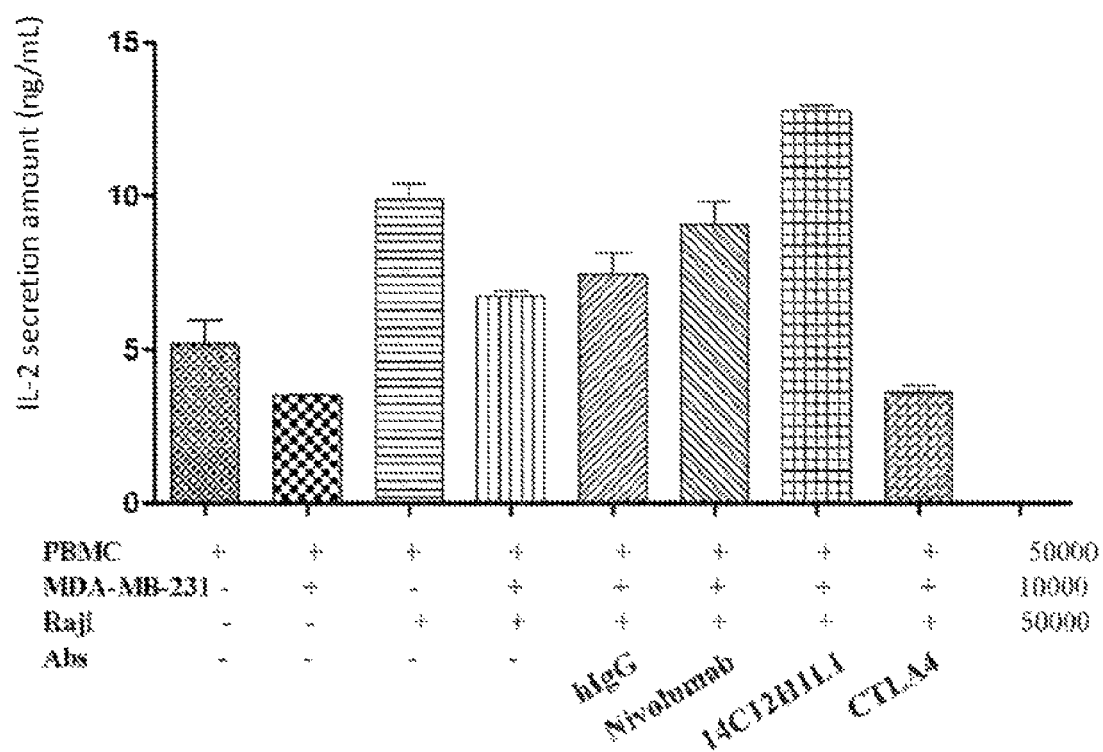
FIG. 58. Effect of 14C12H1L1 on IL-2 Secretion induced by co-culturing of PBMC, MDA-MB-231 and Raji cells.
Figures 59, 60:
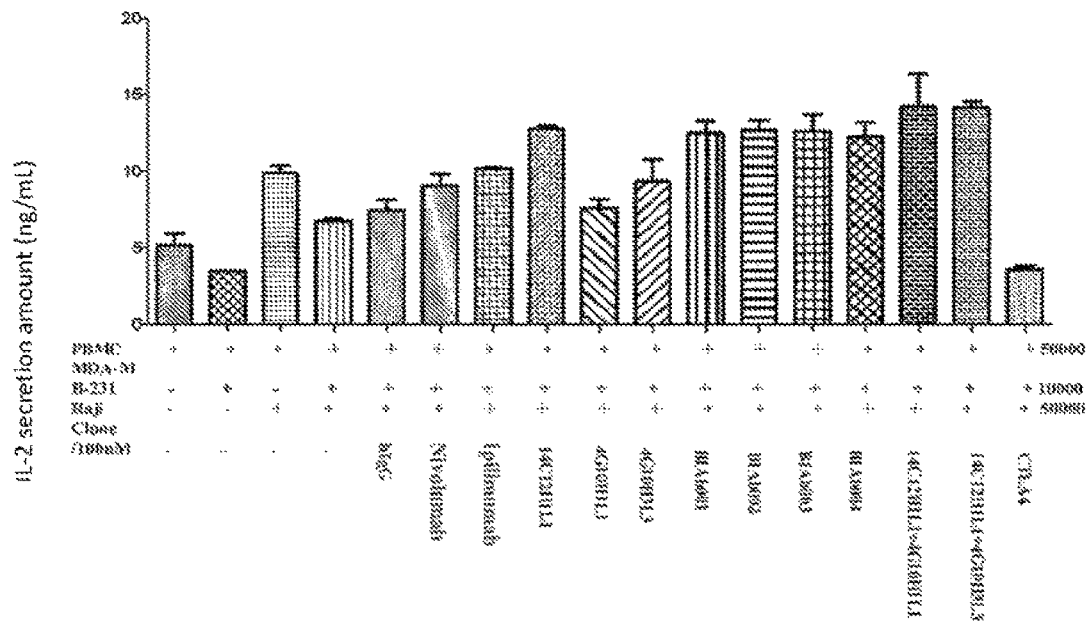
FIG. 59. Effect of BiAb001, BiAb002, BiAb003, and BiAb004 on IL-2 Secretion induced by co-culturing of PBMC, MDA-MB-231 and Raji cells, compared with those of 4G10H1L1, 4G10H3L3, and 14C12H1L1.
FIG. 60. Effect of BiAb004 on the Tumor Growth of MC38 Tumor Model in PD-1 HuGEMM Mice.

The IL-2 secretion after mixed cell culture was shown in FIG. 57, FIG. 58, and FIG. 59, respectively. As shown in the figures, the antibodies 4G10H1L1, 4G10H3L3, and 14C12H1L1, as well as bispecific antibodies BiAb001, BiAb002, BiAb003, and BiAb004 can effectively induce the secretion of IL-2 by PBMCs. The anti-PD-1 antibody 14C12H1L1 can induce a higher IL-2 secretion than the control antibody Nivolumab (FIG. 58), and bispecific antibodies BiAb001, BiAb002, BiAb003, and BiAb004 have the same effects on IL-2 secretion as 14C12H1L1+4G10H1L1 or 14C12H1L1+4G10H3L3 (FIG. 59).

Example 13: Impact of Antibody BiAb004 on the Tumor Growth of MC38 Tumor Model in PD-1 HuGEMM Mice MC38 tumor cells were inoculated subcutaneously on the right side of PD-1 HuGEMM mice ($1 \times 10^6$ cells/mouse, human PD-1 transgenic mice). When the mean tumor volume reached approximately 144 mm$^3$, the mice were randomly divided into 4 experimental groups per tumor volume with 8 mice in each group. Antibodies were given through abdominal administration, the specific grouping and dosages were as follows:

Isotype Control group (dose: 2.67 mg/kg),
BiAb004 high-dose group (dose: 2.67 mg/kg),
BiAb004 low-dose group (dose: 0.267 mg/kg), The above 3 groups were injected with antibodies twice weekly, 5 times in total. After injection, the tumor sizes were measured twice weekly.

The results were presented in FIG. 60.

Evidently:

The tumor sizes in the BiAb004 high-dose, and BiAb004 low-dose groups were all significantly smaller than those in the Isotype control group statistically (P<0.001, P<0.05, respectively). BiAb004 low-dose groups showed a statistically significant antitumor effect on the MC38 tumor model in the PD-1 HuGEMNI mice.

Although specific embodiments of the present invention have been described in detail, as will be appreciated by one skilled in the art, these details may incur various modifications and substitutions according to all the teachings we have disclosed. These changes are all covered by the scope of the present invention. The full scope of the present invention is given by the appended claims and any equivalents.

---

The invention claimed is:

1. A bispecific antibody, or an antigen-binding fragment thereof, comprising:
   (a) a first protein functional area that binds to PD-1 and comprises six CDRs with the amino acid sequences of SEQ ID NOs: 29-34, and
   (b) a second protein functional area that binds to CTLA-4 and comprises six CDRs with the amino acid sequences selected from the group consisting of: (i) SEQ ID NOs: 35-40, (ii) SEQ ID NOs: 35, 41 and 37-40, and (iii) SEQ ID NOs: 42-47.

2. The bispecific antibody, or the antigen-binding fragment thereof, of claim 1, wherein the first protein functional area and the second protein functional area are directly connected or connected by a connecting fragment.

3. The bispecific antibody, or the antigen-binding fragment thereof, of claim 1, wherein the first protein functional area and the second protein functional area are individually contained in immunoglobulins, half antibodies, Fab, F(ab')2, or single-chain antibodies.

4. The bispecific antibody, or the antigen-binding fragment thereof, of claim 3, wherein the immunoglobulin is IgG, IgA, IgD, IgE, or IgM.

5. The bispecific antibody, or the antigen-binding fragment thereof, of claim 4, wherein the immunoglobulin is IgG.

6. The bispecific antibody, or the antigen-binding fragment thereof, of claim 5, wherein the IgG is IgG1, IgG2, IgG3, or IgG4.

7. The bispecific antibody, or the antigen-binding fragment thereof, of claim 3, wherein the single-chain antibody is attached at the c-terminus of the heavy chain of the immunoglobulin.

8. The bispecific antibody, or the antigen-binding fragment thereof, of claim 3, wherein the immunoglobulin, or the antigen-binding fragment thereof, comprises non-CDR regions from species other than mouse.

9. The bispecific antibody, or the antigen-binding fragment thereof, of claim 1, comprising one, two, or more first protein functional areas and one, two, or more second protein functional areas.

10. The bispecific antibody, or the antigen-binding fragment thereof, of claim 1, wherein:
   the first protein functional area comprises a heavy chain variable region comprising CDRs with the amino acid sequences of SEQ ID NOs: 29-31, and a light chain variable region comprising CDRs with the amino acid sequences of SEQ ID NOs: 32-34; and/or, the second protein functional area comprises a heavy chain variable region comprising CDRs with the amino acid sequences of SEQ ID NOs: 35-37, or SEQ ID NOs: 35, 41, and 37, or SEQ ID NOs: 42-44; and a light chain variable region comprising CDRs with the amino acid sequences of SEQ ID NOs: 38-40 or SEQ ID NOs: 45-47.

11. The bispecific antibody, or the antigen-binding fragment thereof, of claim 1, wherein:
the first protein functional area comprises a heavy chain variable region with the amino acid sequence of SEQ ID NO: 16 or 20, and a light chain variable region with the amino acid sequence of SEQ ID NO: 18 or 22; and
the second protein functional area comprises a heavy chain variable region with the amino acid sequence of SEQ ID NO: 2, 6, 10, 14, or 25, and a light chain variable region with the amino acid sequence of SEQ ID NO: 4, 8, 12, or 27.

12. The bispecific antibody, or the antigen-binding fragment thereof, of claim 1, wherein the bispecific antibody, or the antigen-binding fragment thereof, binds to CTLA-4 protein and/or PD-1 protein with a binding affinity ($K_D$) that is less than $10^{-5}$M.

13. A composition comprising one or more isolated nucleic acid molecules, wherein the one or more isolated nucleic acid molecules comprises one or more nucleotide sequences encoding the first protein functional area and the second protein functional area of the bispecific antibody of claim 1.

14. A vector comprising one or more isolated nucleic acid molecules, wherein the one or more isolated nucleic acid molecules comprises one or more nucleotide sequences encoding the first protein functional area and the second protein functional area of the bispecific antibody of claim 1.

15. A host cell line comprising one or more isolated nucleic acid molecules, wherein the one or more isolated nucleic acid molecules comprises one or more nucleotide sequences encoding the first protein functional area and the second protein functional area of the bispecific antibody of claim 1.

16. A method for preparing a bispecific antibody, or an antigen-binding fragment thereof, comprising culturing the host cell line of claim 15 under appropriate conditions, and recovering a bispecific antibody, or an antigen-binding fragment thereof, from the cell culture.

17. A conjugate, comprising the bispecific antibody, or the antigen-binding fragment thereof, of claim 1 and a conjugating partner as a detectable marker.

18. A reagent kit, comprising the bispecific antibody, or the antigen-binding fragment thereof, of claim 1.

19. A method to detect the existence or the levels of CTLA-4 and/or PD-1 in a sample, comprising contacting the sample with the bispecific antibody, or the antigen-binding fragment thereof, of claim 1.

20. A pharmaceutical composition comprising the bispecific antibody, or the antigen-binding fragment thereof, of claim 1 and a pharmaceutically acceptable carrier or excipient.

21. A method for treating or diagnosing tumors in a subject, wherein the method comprises administering to the subject an effective dose of the bispecific antibody, or the antigen-binding fragment thereof, of claim 1, or a conjugate thereof.

22. The bispecific antibody, or the antigen-binding fragment thereof, of claim 1, wherein:
the first protein functional area comprises a heavy chain variable region comprising CDRs with the amino acid sequences of SEQ ID NOs: 29-31 and a light chain variable region comprising CDRs with the amino acid sequences of SEQ ID NOs: 32-34, and
the second protein functional area comprises a heavy chain variable region comprising CDRs with the amino acid sequences of SEQ ID NOs: 35-37 and a light chain variable region comprising CDRs with the amino acid sequences of SEQ ID NOs: 38-40.

23. The bispecific antibody, or the antigen-binding fragment thereof, of claim 1, wherein:
the first protein functional area comprises a heavy chain variable region comprising CDRs with the amino acid sequences of SEQ ID NOs: 29-31 and a light chain variable region comprising CDRs with the amino acid sequences of SEQ ID NOs: 32-34, and
the second protein functional area comprises a heavy chain variable region comprising CDRs with the amino acid sequences of SEQ ID NOs: 35, 41, and 37 and a light chain variable region comprising CDRs with the amino acid sequences of SEQ ID NOs: 38-40.

24. The bispecific antibody, or the antigen-binding fragment thereof, of claim 1, wherein:
the first protein functional area comprises a heavy chain variable region comprising CDRs with the amino acid sequences of SEQ ID NOs: 29-31 and a light chain variable region comprising CDRs with the amino acid sequences of SEQ ID NOs: 32-34, and
the second protein functional area comprises a heavy chain variable region comprising CDRs with the amino acid sequences of SEQ ID NOs: 42-44 and a light chain variable region comprising CDRs with the amino acid sequences of SEQ ID NOs: 45-47.

25. The bispecific antibody, or the antigen-binding fragment thereof, of claim 1, wherein the first protein functional area comprises a heavy chain variable region with the amino acid sequence of SEQ ID NO: 16 or SEQ ID NO: 20 and a light chain variable region with the amino acid sequence of SEQ ID NO: 18 or SEQ ID NO: 22.

26. The bispecific antibody, or the antigen-binding fragment thereof, of claim 1, wherein the second protein functional area comprises a heavy chain variable region with the amino acid sequence of SEQ ID NO: 2, SEQ ID NO: 6 or SEQ ID NO: 10 and a light chain variable region with the amino acid sequence of SEQ ID NO: 4, SEQ ID NO: 8, or SEQ ID NO: 12.

27. The bispecific antibody, or the antigen-binding fragment thereof, of claim 1, wherein the second protein functional area comprises a heavy chain variable region with the amino acid sequence of SEQ ID NO: 14 and a light chain variable region with the amino acid sequence of SEQ ID NO: 12.

28. The bispecific antibody, or the antigen-binding fragment thereof, of claim 1, wherein the second protein functional area comprises a heavy chain variable region with the amino acid sequence of SEQ ID NO: 25 and a light chain variable region with the amino acid sequence of SEQ ID NO: 27.

29. An isolated nucleic acid molecule comprising a nucleotide sequence encoding the bispecific antibody or the antigen-binding fragment thereof of claim 1.

* * * * *

SEQUENCE LISTING

```
<160> NUMBER OF SEQ ID NOS: 47

<210> SEQ ID NO 1
<211> LENGTH: 372
<212> TYPE: DNA
<213> ORGANISM: Artificial
<220> FEATURE:
<223> OTHER INFORMATION: Nucleic acid sequence of 4G10 heavy chain
      variable region

<400> SEQUENCE: 1
caggtcaagc tgcaggagtc tggacctgag ctggtgaagc ctggagcttc aatgaagata      60
tcctgcaagg cttctggtta ctcattcact ggctacacca tgaactgggt gaagcagagc     120
catggaaaga accttgaatg gattggactt attaatcctt acaataatat tactaactac     180
aaccagaagt tcatgggcaa ggccacattt actgtagaca gtcatccag cacagcctac     240 atggaactcc tcagactgac atctgaagac tctggagtct atttctgtgc aagactcgac     300
```

```
tataggtctt attggggcca agggactctg gtcactgtct ctgcagccaa aacgacaccc      360
ccatctgtct at                                                          372
```

<210> SEQ ID NO 2
<211> LENGTH: 124
<212> TYPE: PRT
<213> ORGANISM: Artificial
<220> FEATURE:
<223> OTHER INFORMATION: The amino acid sequence of 4G10 heavy chain
      variable region

<400> SEQUENCE: 2

```
Gln Val Lys Leu Gln Glu Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Asn Ile Thr Asn Tyr Asn Gln Lys Phe
    50                  55                  60

Met Gly Lys Ala Thr Phe Thr Val Asp Lys Ser Ser Thr Ala Tyr
65                  70                  75                  80

Met Glu Leu Leu Arg Leu Thr Ser Glu Asp Ser Gly Val Tyr Phe Cys
                85                  90                  95

Ala Arg Leu Asp Tyr Arg Ser Tyr Trp Gly Gln Gly Thr Leu Val Thr
            100                 105                 110

Val Ser Ala Ala Lys Thr Thr Pro Pro Ser Val Tyr
        115                 120
```

<210> SEQ ID NO 3
<211> LENGTH: 378
<212> TYPE: DNA
<213> ORGANISM: Artificial
<220> FEATURE:
<223> OTHER INFORMATION: Nucleic acid sequence of 4G10 light chain
      variable region

<400> SEQUENCE: 3

```
caggctgttg tgactcagga atctgcactc accacatcac ctggtgaaac agtcacactc      60
acttgtcgct caagtactgg ggctgttaca actagtaact tgccaactg ggtccaagaa       120 aaaccagatc atttattcac tagtctaata ggtggtacca caaccgagc tccaggtgtt      180 cctgccagat tctcaggctc cctgattgga gacaaggctg ccctcaccat cacaggggca      240
cagactgagg atgaggcaat atatttctgt gctctatggt acagcaacca ttgggtgttc      300
ggtggaggaa ccaaactgac tgtcctaggc cagcccaagt cttcgccatc agtcaccctg      360
tttcaagggc aattctgc                                                   378
```

<210> SEQ ID NO 4
<211> LENGTH: 126
<212> TYPE: PRT
<213> ORGANISM: Artificial
<220> FEATURE:
<223> OTHER INFORMATION: The amino acid sequence of 4G10 light chain
      variable region

<400> SEQUENCE: 4

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
```

```
                  20                  25                  30
Asn Phe Ala Asn Trp Val Gln Glu Lys Pro Asp His Leu Phe Thr Ser
            35                  40                  45

Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Gly Gln Pro
            100                 105                 110

Lys Ser Ser Pro Ser Val Thr Leu Phe Gln Gly Gln Phe Cys
        115                 120                 125
```

<210> SEQ ID NO 5
<211> LENGTH: 345
<212> TYPE: DNA
<213> ORGANISM: Artificial
<220> FEATURE:
<223> OTHER INFORMATION: Nucleic acid sequence of 4G10H1L1 heavy chain
      variable region

<400> SEQUENCE: 5

```
caggtgcagc tggtggagtc tggggccgag ctggtgaagc ccggcgcctc catgaagatc    60
tcttgcaagg ccagcggata cagtttcact ggctatacca tgaactgggt caaacaggct   120
ccaggacagg gactggagtg gatcgggctg attaatcctt acaacaacat caccaactac   180
aaccagaagt tcatgggaaa agcaaccttt acagtggaca gagcattttc cacagcctac   240
atggaactga gccggctgac ttcagacgat agcggggtct attttgtgc aaggctggat   300 tatcgctctt actgggggca gggaactctg gtcactgtct ccgct              345
```

<210> SEQ ID NO 6
<211> LENGTH: 115
<212> TYPE: PRT
<213> ORGANISM: Artificial
<220> FEATURE:
<223> OTHER INFORMATION: The amino acid sequence of 4G10H1L1 heavy chain
      variable region

<400> SEQUENCE: 6

```
Gln Val Gln Leu Val Glu Ser Gly Ala Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ala Pro Gly Gln Gly Leu Glu Trp Ile
        35                  40                  45

Gly Leu Ile Asn Pro Tyr Asn Asn Ile Thr Asn Tyr Asn Gln Lys Phe
    50                  55                  60

Met Gly Lys Ala Thr Phe Thr Val Asp Lys Ser Ile Thr Ala Tyr
65                  70                  75                  80

Met Glu Leu Ser Arg Leu Thr Ser Asp Asp Ser Gly Val Tyr Phe Cys
                85                  90                  95

Ala Arg Leu Asp Tyr Arg Ser Tyr Trp Gly Gln Gly Thr Leu Val Thr
            100                 105                 110

Val Ser Ala
        115
```

```
<210> SEQ ID NO 7
<211> LENGTH: 327
<212> TYPE: DNA
<213> ORGANISM: Artificial
<220> FEATURE:
<223> OTHER INFORMATION: Nucleic acid sequence of 4G10H1L1 light chain
      variable region

<400> SEQUENCE: 7
caggctgtcg tcactcagga accttcactg actgtgagcc caggaggaac tgtcaccctg      60
acatgcggaa gctccaccgg agcagtgacc acatccaact tcgccaattg ggtccaggaa     120
aagccaggcc aggcatttcg atccctgatc ggaggcacaa acaatcgggc ttcttgggtg     180
cccgcaagat tctcaggaag cctgctgggg ggaaaagccg ctctgaccat tagtggcgct     240
cagcctgagg acgaagccga gtacttctgc gctctgtggt atagcaacca ctgggtgttt     300
ggcgggggaa caaagctgac tgtgctg                                         327

<210> SEQ ID NO 8
<211> LENGTH: 109
<212> TYPE: PRT
<213> ORGANISM: Artificial
<220> FEATURE:
<223> OTHER INFORMATION: The amino acid sequence of 4G10H1L1 light chain
      variable region

<400> SEQUENCE: 8

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Phe Ala Asn Trp Val Gln Glu Lys Pro Gly Gln Ala Phe Arg Ser
        35                  40                  45

Leu Ile Gly Gly Thr Asn Asn Arg Ala Ser Trp Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 9
<211> LENGTH: 345
<212> TYPE: DNA
<213> ORGANISM: Artificial
<220> FEATURE:
<223> OTHER INFORMATION: Nucleic acid sequence of 4G10H3L3 heavy chain
      variable region

<400> SEQUENCE: 9
caggtgcagc tggtcgagtc tggggccgaa gtgaagaaac ccggcgcctc agtgaaggtc      60
agctgcaagg ccagcgggta cagtttcact ggatatacca tgaactgggt ccgacaggcc    120
cctggccagg gctggagtg gatcggcctg attaacccct acaacaacat cactaactac     180
gcacagaagt tccaggggag agtgaccttt acagtggaca ccagcatttc cacagcctac     240
atggaactgt cccggctgag atctgacgat acaggcgtgt acttctgcgc taggctggat     300
taccgcagct attggggaca gggcacactg gtgactgtca gcgca                    345

<210> SEQ ID NO 10
```

<211> LENGTH: 115
<212> TYPE: PRT
<213> ORGANISM: Artificial
<220> FEATURE:
<223> OTHER INFORMATION: The amino acid sequence of 4G10H3L3 heavy chain variable region

<400> SEQUENCE: 10

```
Gln Val Gln Leu Val Glu Ser Gly Ala Glu Val Lys Lys Pro Gly Ala
1               5                   10                  15
Ser Val Lys Val Ser Cys Lys Ala Ser Gly Tyr Ser Phe Thr Gly Tyr
            20                  25                  30
Thr Met Asn Trp Val Arg Gln Ala Pro Gly Gln Gly Leu Glu Trp Ile
        35                  40                  45
Gly Leu Ile Asn Pro Tyr Asn Asn Ile Thr Asn Tyr Ala Gln Lys Phe
    50                  55                  60
Gln Gly Arg Val Thr Phe Thr Val Asp Thr Ser Ile Ser Thr Ala Tyr
65                  70                  75                  80
Met Glu Leu Ser Arg Leu Arg Ser Asp Asp Thr Gly Val Tyr Phe Cys
                85                  90                  95
Ala Arg Leu Asp Tyr Arg Ser Tyr Trp Gly Gln Gly Thr Leu Val Thr
            100                 105                 110
Val Ser Ala
        115
```

<210> SEQ ID NO 11
<211> LENGTH: 327
<212> TYPE: DNA
<213> ORGANISM: Artificial
<220> FEATURE:
<223> OTHER INFORMATION: Nucleic acid sequence of 4G10H3L3 light chain variable region

<400> SEQUENCE: 11

```
caggctgtcg tcactcagga accttcactg accgtgtctc ctggcgggac tgtcaccctg      60
acatgcggca gctccacagg ggccgtgacc acaagtaact tcccaaattg ggtccagcag     120
aagccaggac aggctccccg gagtctgatc ggaggcacca caacaaggc cagctggaca     180
cccgcacggt tcagcggcag cctgctgggc ggcaaggccg ctctgacaat tagcggagcc    240
cagcctgagg acgaagccga gtactattgc gctctgtggt actccaacca ctgggtgttc    300
ggcggcggca ccaagctgac tgtgctg                                         327
```

<210> SEQ ID NO 12
<211> LENGTH: 109
<212> TYPE: PRT
<213> ORGANISM: Artificial
<220> FEATURE:
<223> OTHER INFORMATION: The amino acid sequence of 4G10H3L3 light chain variable region

<400> SEQUENCE: 12

```
Gln Ala Val Val Thr Gln Glu Pro Ser Leu Thr Val Ser Pro Gly Gly
1               5                   10                  15
Thr Val Thr Leu Thr Cys Gly Ser Ser Thr Gly Ala Val Thr Thr Ser
            20                  25                  30
Asn Phe Pro Asn Trp Val Gln Gln Lys Pro Gly Gln Ala Pro Arg Ser
        35                  40                  45
Leu Ile Gly Gly Thr Asn Asn Lys Ala Ser Trp Thr Pro Ala Arg Phe
    50                  55                  60
```

```
Ser Gly Ser Leu Leu Gly Gly Lys Ala Ala Leu Thr Ile Ser Gly Ala
 65                  70                  75                  80

Gln Pro Glu Asp Glu Ala Glu Tyr Tyr Cys Ala Leu Trp Tyr Ser Asn
                 85                  90                  95

His Trp Val Phe Gly Gly Gly Thr Lys Leu Thr Val Leu
            100                 105

<210> SEQ ID NO 13
<211> LENGTH: 345
<212> TYPE: DNA
<213> ORGANISM: Artificial
<220> FEATURE:
<223> OTHER INFORMATION: Nucleic acid sequence of 4G10H4L3 heavy chain
      variable region

<400> SEQUENCE: 13
caggtgcagc tggtcgagtc tggggccgaa gtgaagaaac ccggcgcctc agtgaaggtc      60
agctgcaagg ccagcgggta cagtttcact ggatatacca tgaactgggt ccgacaggcc    120
cctggccagg ggctggagtg gatcggcctg attaacccct acaacgacat cactaactac    180
gcacagaagt tccaggggag agtgaccttt acagtggaca ccagcatttc cacagcctac    240
atggaactgt cccggctgag atctgacgat acaggcgtgt acttctgcgc taggctggat    300
taccgcagct attggggaca gggcacactg gtgactgtca gcgca                    345

<210> SEQ ID NO 14
<211> LENGTH: 115
<212> TYPE: PRT
<213> ORGANISM: Artificial
<220> FEATURE:
<223> OTHER INFORMATION: The amino acid sequence of 4G10H4L3 heavy chain
      variable region

<400> SEQUENCE: 14

Gln Val Gln Leu Val Glu Ser Gly Ala Glu Val Lys Lys Pro Gly Ala
  1               5                  10                  15

Ser Val Lys Val Ser Cys Lys Ala Ser Gly Tyr Ser Phe Thr Gly Tyr
                 20                  25                  30

Thr Met Asn Trp Val Arg Gln Ala Pro Gly Gln Gly Leu Glu Trp Ile
             35                  40                  45

Gly Leu Ile Asn Pro Tyr Asn Asp Ile Thr Asn Tyr Ala Gln Lys Phe
 50                  55                  60

Gln Gly Arg Val Thr Phe Thr Val Asp Thr Ser Ile Ser Thr Ala Tyr
 65                  70                  75                  80

Met Glu Leu Ser Arg Leu Arg Ser Asp Asp Thr Gly Val Tyr Phe Cys
                 85                  90                  95

Ala Arg Leu Asp Tyr Arg Ser Tyr Trp Gly Gln Gly Thr Leu Val Thr
            100                 105                 110

Val Ser Ala
       115

<210> SEQ ID NO 15
<211> LENGTH: 354
<212> TYPE: DNA
<213> ORGANISM: Artificial
<220> FEATURE:
<223> OTHER INFORMATION: Nucleic acid sequence of 14C12 heavy chain
      variable region

<400> SEQUENCE: 15
gaggtcaaac tggtggagag cggcggcggg ctggtgaagc ccggcgggtc actgaaactg      60
```

```
agctgcgccg cttccggctt cgcctttagc tcctacgaca tgtcatgggt gaggcagacc    120
cctgagaagc gcctggaatg ggtcgctact atcagcggag gcgggcgata cacctactat    180
cctgactctg tcaaagggag attcacaatt agtcgggata cgccagaaa tactctgtat     240 ctgcagatgt ctagtctgcg gtccgaggat acagctctgt actattgtgc aaaccggtac    300
ggcgaagcat ggtttgccta ttggggacag ggcaccctgg tgacagtctc tgcc          354
```

<210> SEQ ID NO 16
<211> LENGTH: 118
<212> TYPE: PRT
<213> ORGANISM: Artificial
<220> FEATURE:
<223> OTHER INFORMATION: The amino acid sequence of 14C12 heavy chain
      variable region

<400> SEQUENCE: 16

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ala
        115
```

<210> SEQ ID NO 17
<211> LENGTH: 318
<212> TYPE: DNA
<213> ORGANISM: Artificial
<220> FEATURE:
<223> OTHER INFORMATION: Nucleic acid sequence of 14C12 light chain
      variable region

<400> SEQUENCE: 17

```
gacattaaga tgacacagtc cccttcctca atgtacgcta gcctgggcga gcgagtgacc    60
ttcacatgca aagcatccca ggacatcaac acatacctgt cttggtttca gcagaagcca    120
ggcaaaagcc ccaagaccct gatctaccgg gccaatagac tggtgacgg ggtccccagc     180 agattctccg gatctggcag tgggcaggat tactccctga ccatcagctc cctggagtat    240
gaagacatgg gcatctacta ttgcctgcag tatgatgagt ccctctgac ctttggagca     300 ggcacaaaac tggaactg                                                  318
```

<210> SEQ ID NO 18
<211> LENGTH: 106
<212> TYPE: PRT
<213> ORGANISM: Artificial
<220> FEATURE:
<223> OTHER INFORMATION: The amino acid sequence of 14C12 light chain
      variable region

<400> SEQUENCE: 18

```
Asp Ile Lys Met Thr Gln Ser Pro Ser Ser Met Tyr Ala Ser Leu Gly
1               5                   10                  15

Glu Arg Val Thr Phe Thr Cys Lys Ala Ser Gln Asp Ile Asn Thr Tyr
            20                  25                  30

Leu Ser Trp Phe Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu
            100                 105
```

<210> SEQ ID NO 19
<211> LENGTH: 354
<212> TYPE: DNA
<213> ORGANISM: Artificial
<220> FEATURE:
<223> OTHER INFORMATION: Nucleic acid sequence of 14C12H1L1 heavy chain variable region

<400> SEQUENCE: 19

```
gaagtgcagc tggtcgagtc tgggggaggg ctggtgcagc ccggcgggtc actgcgactg     60
agctgcgcag cttccggatt cgcctttagc tcctacgaca tgtcctgggt gcgacaggca    120
ccaggaaagg gactggattg ggtcgctact atctcaggag gcgggagata cacctactat    180
cctgacagcg tcaagggccg gttcacaatc tctagagata caagtaagaa caatctgtat    240
ctgcagatga acagcctgag ggctgaggac accgcactgt actattgtgc caaccgctac    300
ggggaagcat ggtttgccta ttgggggcag ggaaccctgg tgacagtctc tagt          354
```

<210> SEQ ID NO 20
<211> LENGTH: 118
<212> TYPE: PRT
<213> ORGANISM: Artificial
<220> FEATURE:
<223> OTHER INFORMATION: The amino acid sequence of 14C12H1L1 heavy chain variable region

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Asp Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ser
            115
```

<210> SEQ ID NO 21
<211> LENGTH: 321
<212> TYPE: DNA
<213> ORGANISM: Artificial
<220> FEATURE:
<223> OTHER INFORMATION: Nucleic acid sequence of 14C12H1L1 light chain
      variable region

<400> SEQUENCE: 21

```
gacattcaga tgactcagag cccctcctcc atgtccgcct ctgtgggcga cagggtcacc      60
ttcacatgcc gcgctagtca ggatatcaac acctacctga ctggtttca gcagaagcca     120 gggaaaagcc ccaagacact gatctaccgg gctaatagac tggtgtctgg agtcccaagt    180
cggttcagtg gctcagggag cggacaggac tacactctga ccatcagctc cctgcagcct    240
gaggacatgg caacctacta ttgcctgcag tatgatgagt tcccactgac ctttggcgcc    300
gggacaaaac tggagctgaa g                                              321
```

<210> SEQ ID NO 22
<211> LENGTH: 107
<212> TYPE: PRT
<213> ORGANISM: Artificial
<220> FEATURE:
<223> OTHER INFORMATION: The amino acid sequence of 14C12H1L1 light
      chain variable region

<400> SEQUENCE: 22

Asp Ile Gln Met Thr Gln Ser Pro Ser Ser Met Ser Ala Ser Val Gly
1               5                   10                  15

Asp Arg Val Thr Phe Thr Cys Arg Ala Ser Gln Asp Ile Asn Thr Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Ser Gly Val Pro Ser Arg Phe Ser Gly
        50                  55                  60

Ser Gly Ser Gly Gln Asp Tyr Thr Leu Thr Ile Ser Ser Leu Gln Pro
65                  70                  75                  80

Glu Asp Met Ala Thr Tyr Tyr Cys Leu Gln Tyr Asp Glu Phe Pro Leu
                85                  90                  95

Thr Phe Gly Ala Gly Thr Lys Leu Glu Leu Lys
            100                 105

<210> SEQ ID NO 23
<211> LENGTH: 15
<212> TYPE: PRT
<213> ORGANISM: Artificial
<220> FEATURE:
<223> OTHER INFORMATION: Linker 1

<400> SEQUENCE: 23

Gly Gly Gly Gly Ser Gly Gly Gly Ser Gly Gly Gly Gly Ser
1               5                   10                  15

<210> SEQ ID NO 24
<211> LENGTH: 20
<212> TYPE: PRT
<213> ORGANISM: Artificial
<220> FEATURE:
<223> OTHER INFORMATION: Linker 2

<400> SEQUENCE: 24

Gly Gly Gly Gly Ser Gly Gly Gly Ser Gly Gly Gly Ser Gly
1               5                   10                  15

Gly Gly Gly Ser
        20

<210> SEQ ID NO 25
<211> LENGTH: 115
<212> TYPE: PRT
<213> ORGANISM: Artificial
<220> FEATURE:
<223> OTHER INFORMATION: The amino acid sequence of 8D2H14L2 heavy chain
      variable region

<400> SEQUENCE: 25

Glu Val Gln Leu Val Glu Ser Gly Gly Gly Leu Val Gln Pro Gly Gly
1               5                   10                  15

Ser Ser Arg Leu Ser Cys Ala Ala Ser Gly Phe Thr Phe Ser Asp Asn
            20                  25                  30

Trp Met Asn Trp Val Arg Gln Ala Pro Gly Lys Gly Leu Glu Trp Leu
        35                  40                  45

Ala Gln Ile Arg Asn Lys Pro Tyr Asn Tyr Glu Thr Tyr Tyr Ser Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Gly Val Tyr
                85                  90                  95

Tyr Cys Thr Ala Gln Phe Ala Tyr Trp Gly Gln Gly Thr Leu Val Thr
            100                 105                 110

Val Ser Ser
        115

<210> SEQ ID NO 26
<211> LENGTH: 345
<212> TYPE: DNA
<213> ORGANISM: Artificial
<220> FEATURE:
<223> OTHER INFORMATION: Nucleic acid sequence of 8D2H14L2 heavy chain
      variable region

<400> SEQUENCE: 26
gaggtgcagc tggtcgaatc tggaggagga ctggtgcagc ctggaggaag ctcccggctg      60
tcatgtgccg ctagcggctt cacctttttcc gacaactgga tgaattgggt gcgacaggca    120 ccagg caaag gactggagtg gctggctcag atccggaaca agccctacaa ttatgaaaca    180
tactatagcg cctccgtgaa aggccggttc actattagta gagacgattc taagaacagc    240
gtgtacctgc agatgaatag cctgaagaca gaggatactg gcgtctacta ttgcacagca    300
cagtttgcct attggggaca gggcaccctg gtgacagtct ctagt                    345

<210> SEQ ID NO 27
<211> LENGTH: 107
<212> TYPE: PRT
<213> ORGANISM: Artificial
<220> FEATURE:
<223> OTHER INFORMATION: The amino acid sequence of 8D2H14L2 light chain
      variable region

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Gly Gly

```
                 20                  25                  30

Leu Asn Trp Tyr Gln Arg Lys Pro Gly Lys Ser Pro Lys Leu Leu Ile
            35                  40                  45

Tyr Gly Ala Thr Asn Leu Ala Ser Gly Val Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Asn Val Leu Arg Ser Pro Phe
                85                  90                  95

Thr Phe Gly Ser Gly Thr Lys Leu Glu Ile Lys
            100                 105

<210> SEQ ID NO 28
<211> LENGTH: 321
<212> TYPE: DNA
<213> ORGANISM: Artificial
<220> FEATURE:
<223> OTHER INFORMATION: Nucleic acid sequence of 8D2H14L2 light chain
      variable region

<400> SEQUENCE: 28
gacatccaga tgactcagag cccctcaagc ctgtctgcaa gtgtgggcga tagggtcacc       60
atcacatgtc gcacctccga aaacatctac ggggactga attggtatca gcgcaagccc      120
ggcaaatccc ctaagctgct gatctacggc gctaccaacc tggcatctgg ggtgtcctct     180 cgatttcag ggagcggcag cggcaccgac tatactctga ccattagttc actgcagcct     240
gaggatgtgg ccacatacta ttgccagaat gtcctgagat caccattcac ttttgggagc    300
ggaaccaaac tggaaattaa g                                               321

<210> SEQ ID NO 29
<211> LENGTH: 8
<212> TYPE: PRT
<213> ORGANISM: Artificial
<220> FEATURE:
<223> OTHER INFORMATION: 14C12HCDR1

<400> SEQUENCE: 29

Gly Phe Ala Phe Ser Ser Tyr Asp
1               5

<210> SEQ ID NO 30
<211> LENGTH: 8
<212> TYPE: PRT
<213> ORGANISM: Artificial
<220> FEATURE:
<223> OTHER INFORMATION: 14C12HCDR2

<400> SEQUENCE: 30

Ile Ser Gly Gly Gly Arg Tyr Thr
1               5

<210> SEQ ID NO 31
<211> LENGTH: 11
<212> TYPE: PRT
<213> ORGANISM: Artificial
<220> FEATURE:
<223> OTHER INFORMATION: 14C12HCDR3

<400> SEQUENCE: 31

Ala Asn Arg Tyr Gly Glu Ala Trp Phe Ala Tyr
1               5                   10
```

<210> SEQ ID NO 32
<211> LENGTH: 6
<212> TYPE: PRT
<213> ORGANISM: Artificial
<220> FEATURE:
<223> OTHER INFORMATION: 14C12LCDR1

<400> SEQUENCE: 32

Gln Asp Ile Asn Thr Tyr
1               5

<210> SEQ ID NO 33
<211> LENGTH: 3
<212> TYPE: PRT
<213> ORGANISM: Artificial
<220> FEATURE:
<223> OTHER INFORMATION: 14C12LCDR2

<400> SEQUENCE: 33

Arg Ala Asn
1

<210> SEQ ID NO 34
<211> LENGTH: 9
<212> TYPE: PRT
<213> ORGANISM: Artificial
<220> FEATURE:
<223> OTHER INFORMATION: 14C12LCDR3

<400> SEQUENCE: 34

Leu Gln Tyr Asp Glu Phe Pro Leu Thr
1               5

<210> SEQ ID NO 35
<211> LENGTH: 8
<212> TYPE: PRT
<213> ORGANISM: Artificial
<220> FEATURE:
<223> OTHER INFORMATION: 4G10HCDR1

<400> SEQUENCE: 35

Gly Tyr Ser Phe Thr Gly Tyr Thr
1               5

<210> SEQ ID NO 36
<211> LENGTH: 8
<212> TYPE: PRT
<213> ORGANISM: Artificial
<220> FEATURE:
<223> OTHER INFORMATION: 4G10HCR2

<400> SEQUENCE: 36

Ile Asn Pro Tyr Asn Asn Ile Thr
1               5

<210> SEQ ID NO 37
<211> LENGTH: 8
<212> TYPE: PRT
<213> ORGANISM: Artificial
<220> FEATURE:
<223> OTHER INFORMATION: 4G10HCDR3

<400> SEQUENCE: 37

Ala Arg Leu Asp Tyr Arg Ser Tyr
1               5

```
<210> SEQ ID NO 38
<211> LENGTH: 9
<212> TYPE: PRT
<213> ORGANISM: Artificial
<220> FEATURE:
<223> OTHER INFORMATION: 4G10LCDR1

<400> SEQUENCE: 38

Thr Gly Ala Val Thr Thr Ser Asn Phe
1               5

<210> SEQ ID NO 39
<211> LENGTH: 3
<212> TYPE: PRT
<213> ORGANISM: Artificial
<220> FEATURE:
<223> OTHER INFORMATION: 4G10LCDR2

<400> SEQUENCE: 39

Gly Thr Asn
1

<210> SEQ ID NO 40
<211> LENGTH: 9
<212> TYPE: PRT
<213> ORGANISM: Artificial
<220> FEATURE:
<223> OTHER INFORMATION: 4G10LCDR3

<400> SEQUENCE: 40

Ala Leu Trp Tyr Ser Asn His Trp Val
1               5

<210> SEQ ID NO 41
<211> LENGTH: 8
<212> TYPE: PRT
<213> ORGANISM: Artificial
<220> FEATURE:
<223> OTHER INFORMATION: 4G10H4L3HCDR2

<400> SEQUENCE: 41

Ile Asn Pro Tyr Asn Asp Ile Thr
1               5

<210> SEQ ID NO 42
<211> LENGTH: 8
<212> TYPE: PRT
<213> ORGANISM: Artificial
<220> FEATURE:
<223> OTHER INFORMATION: 8D2H14L2HCDR1

<400> SEQUENCE: 42

Gly Phe Thr Phe Ser Asp Asn Trp
1               5

<210> SEQ ID NO 43
<211> LENGTH: 10
<212> TYPE: PRT
<213> ORGANISM: Artificial
<220> FEATURE:
<223> OTHER INFORMATION: 8D2H14L2HCDR2

<400> SEQUENCE: 43

Ile Arg Asn Lys Pro Tyr Asn Tyr Glu Thr
1               5                   10

<210> SEQ ID NO 44
```

```
<211> LENGTH: 6
<212> TYPE: PRT
<213> ORGANISM: Artificial
<220> FEATURE:
<223> OTHER INFORMATION: 8D2H14L2HCDR3

<400> SEQUENCE: 44

Thr Ala Gln Phe Ala Tyr
1               5

<210> SEQ ID NO 45
<211> LENGTH: 6
<212> TYPE: PRT
<213> ORGANISM: Artificial
<220> FEATURE:
<223> OTHER INFORMATION: 8D2H14L2LCDR1

<400> SEQUENCE: 45

Glu Asn Ile Tyr Gly Gly
1               5

<210> SEQ ID NO 46
<211> LENGTH: 3
<212> TYPE: PRT
<213> ORGANISM: Artificial
<220> FEATURE:
<223> OTHER INFORMATION: 8D2H14L2LCDR2

<400> SEQUENCE: 46

Gly Ala Thr
1

<210> SEQ ID NO 47
<211> LENGTH: 10
<212> TYPE: PRT
<213> ORGANISM: Artificial
<220> FEATURE:
<223> OTHER INFORMATION: 8D2H14L2LCDR3

<400> SEQUENCE: 47

Gln Asn Val Leu Arg Ser Pro Phe Thr Phe
1               5                   10
```